US012678460B2

(12) United States Patent
Dunham et al.

(10) Patent No.: US 12,678,460 B2
(45) Date of Patent: Jul. 14, 2026

(54) METHODS FOR MANAGING ADVERSE EVENTS IN PATIENTS WITH INFLAMMATION

(71) Applicant: Hemanext Inc., Lexington, MA (US)

(72) Inventors: Andrew Dunham, Tower Lakes, IL (US); Tatsuro Yoshida, West Newton, MA (US); Samuel O. Sowemimo-Coker, Dix Hills, NY (US)

(73) Assignee: Hemanext Inc., Lexington, MA (US)

( * ) Notice: Subject to any disclaimer, the term of this patent is extended or adjusted under 35 U.S.C. 154(b) by 192 days.

(21) Appl. No.: 18/157,652

(22) Filed: Jan. 20, 2023

(65) Prior Publication Data

US 2023/0248767 A1    Aug. 10, 2023

Related U.S. Application Data

(63) Continuation of application No. 17/292,597, filed as application No. PCT/US2019/061565 on Nov. 14, 2019, now Pat. No. 12,447,177.

(60) Provisional application No. 62/768,667, filed on Nov. 16, 2018.

(51) Int. Cl.
*A61K 35/14*        (2015.01)
*A61P 7/06*        (2006.01)

(52) U.S. Cl.
CPC ............... *A61K 35/14* (2013.01); *A61P 7/06* (2018.01)

(58) Field of Classification Search
None
See application file for complete search history.

(56) References Cited

U.S. PATENT DOCUMENTS

| | | | |
|---|---|---|---|
| 4,769,318 A | 9/1988 | Hamasaki et al. | |
| 4,880,786 A | 11/1989 | Sasakawa et al. | |
| 5,476,764 A | 12/1995 | Bitensky | |
| 5,624,794 A | 4/1997 | Bitensky et al. | |
| 5,789,151 A | 8/1998 | Bitensky et al. | |
| 6,162,396 A | 12/2000 | Bitensky et al. | |
| 6,413,713 B1 | 7/2002 | Serebrennikov | |
| 6,447,987 B1 | 9/2002 | Hess et al. | |
| 10,603,417 B2 * | 3/2020 | Yoshida | A61M 1/0209 |
| 11,013,771 B2 | 5/2021 | Yoshida et al. | |
| 11,090,331 B2 | 8/2021 | D'Alessandro et al. | |
| 11,433,164 B2 * | 9/2022 | Yoshida | A01N 1/126 |
| 11,576,931 B2 | 2/2023 | Dunham et al. | |
| 2012/0129149 A1 * | 5/2012 | Federspiel | B01D 63/0221 422/44 |
| 2013/0004937 A1 | 1/2013 | Yoshida et al. | |
| 2021/0401883 A1 | 12/2021 | Dunham et al. | |

FOREIGN PATENT DOCUMENTS

| | | |
|---|---|---|
| CN | 103037869 A | 4/2013 |
| CN | 103732056 A | 4/2014 |
| CN | 107735095 A | 2/2018 |
| WO | WO 2016/187353 A1 | 11/2016 |
| WO | WO 2017/223377 A1 | 12/2017 |
| WO | WO 2020/102602 | 5/2020 |

OTHER PUBLICATIONS

Brown et al., "Length of red cell unit storage and risk for delirium after cardiac surgery," *Anesthesia & Analgesia*, 119(2):242-250 (2014).

Chaplin et al., "The proper use of previously frozen red blood cells for transfusion," *Blood*, 59(6): 1118-1120 (1982).

Ciccia et al., "Pediatric acute kidney injury: prevalence, impact and management challenges," *Int. J. Nephrol. Renovasc. Dis.*, 10:77-84 (2017).

D'Alessandro et al., "An update on red blood cell storage lesions, as gleaned through biochemistry and omics technologies," *Transfusion*, 55(1):205-19 (2015).

D'Alessandro et al., "Citrate metabolism in red blood cells stored in additive solution-3," *Transfusion*, 57(2):325-336 (2017).

D'Alessandro et al., "Metabolomics of AS-5 RBC supernatants following routine storage," *Vox Sanguinis*, 108(2):131-140 (2014).

D'Alessandro et al., "Omics markers of the red cell storage lesion and metabolic linkage," *Blood Transfusion*, 15:137-144 (2017).

D'Alessandro et al., "Red blood cell storage in additive solution-7 preserves energy and redox metabolism: a metabolomics approach," *Transfusion*, 55(12):2955-2966 (2015).

D'Alessandro et al., "Routine storage of red blood cell (RBC) units in additive solution-3: a comprehensive investigation of the RBC metabolome," *Transfusion*, 55(6):1155-1168 (2015).

Flegel et al., "Does prolonged storage of red blood cells cause harm?" *British Journal of Haematology*, 165(1):3-16 (2014).

Fox et al., "Earlier Endpoints Are Required for Hemorrhagic Shock Trials among Severely Injured Patients," *Shock*, 47(5):567-573 (2017).

Gowda, et al., "Markers of renal function tests," *North American Journal of Medical Sciences*, 2(4): 170-173(2010).

Hashmi et al., "Predictors of mortality in geriatric trauma patients: A systematic review and meta-analysis," *The Journal of Trauma and Acute Care Surgery*, 76(3):894-901 (2014).

Hod et al., "Transfusion of human volunteers with older, stored red blood cells produces extravascular hemolysis and circulating non-transferrin-bound iron," *Blood*, 118(25):6675-6682 (2011).

International Search Report dated Jan. 31, 2020 in Int'l Appln. PCT/US2019/061565.

Jy et al., "Microparticles in stored red blood cells as potential mediators of transfusion complications," *Transfusion*, 51(4):886-893 (2011).

Kim-Shapiro et al., "Storage lesion: role of red blood cell breakdown," *Transfusion*, 51(4):844-851 (2011).

Kleiner., et al., "Cytokine Levels in the Serum of Healthy Subjects," *Mediators of Inflammation*, 2013(434010):1-6 (2013).

Kreutziger et al., "Admission blood glucose predicted haemorrhagic shock in multiple trauma patients," *Injury*, 46(1):15-20 (2015).

(Continued)

*Primary Examiner* — Susan Hoffman

(74) *Attorney, Agent, or Firm* — Arnold & Porter Kaye Scholer LLP

(57) ABSTRACT

Methods for prevention and reversal of inflammation.

9 Claims, 36 Drawing Sheets

(56) References Cited

OTHER PUBLICATIONS

Laird et al., "Relationship of Early Hyperglycemia to Mortality in Trauma Patients," *The Journal of Trauma and Acute Care Surgery*, 56(5):1058-1062 (2004).

Liu et al., "Mechanism of faster NO scavenging by older stored red blood cells," *Redox Biology*, 2:211-219 (2014).

Norton, et al., "Injuries," *The New England Journal of Medicine*, 368:1723-1730 (2013).

Platt, "Sickle cell anemia as an inflammatory disease," *The Journal of Clinical Investigation*, 106(3): 337-338 (2000).

Prestia et al., "Transfusion of stored blood impairs host defenses against Gram-negative pathogens in mice," *Transfusion*, 54(11):2842-2851 (2014).

Redlin et al., "Red Blood Cell Storage Duration Is Associated with Various Clinical Outcomes in Pediatric Cardiac Surgery," *Transfusion Medicine and Hemotherapy*, 41:146-151 (2014).

Régnier et al., "Prognostic Significance of Blood Lactate and Lactate Clearance in Trauma Patients," *Anesthesiology*, 117(6):1276-1288 (2012).

Reisz et al., "Oxidative modifications of glyceraldehyde 3-phosphate dehydrogenase regulate metabolic reprogramming of stored red blood cells e-blood," Blood, 128(12):e32-e42 (2016).

Reynolds et al., "The transfusion problem: role of aberrant S-nitrosylation," *Transfusion*, 51(4):852-858 (2011).

Roback et al., "Insufficient nitric oxide bioavailability: a hypothesis to explain adverse effects of red blood cell transfusion," *Transfusion*, 51(4):859-866 (2011).

Roback et al., "Metabolomics of ADSOL (AS-1) Red Blood Cell Storage," *Transfusion Medicine Reviews*, 28(2):41-55 (2014).

Rogers et al., "Storage Duration of Red Blood Cell Transfusion and *Clostridium difficile* Infection: A Within Person Comparison," *PLOS ONE*, 9(2):e89332 (2014).

Spinella et al., "Does the storage duration of blood products affect outcomes in critically ill patients?" *Transfusion*, 51(8):1644-1650 (2011).

Spinella et al., "Properties of stored RBCs: Understanding immune and vascular reactivity," *Transfusion*, 51(4):894-900 (2011).

Treeprasertsuk et al., "Urine neutrophil gelatinase-associated lipocalin: a diagnostic and prognostic marker for acute kidney injury (AKI) in hospitalized cirrhotic patients with AKI-prone conditions," *BMC Gastroenterology*, 15:140 (2015).

Valeri et al., "The survival, function, and hemolysis of human RBCs stored at 4°C in additive solution (AS-1, AS-3, or AS-5) for 42 days and then biochemically modified, frozen, thawed, washed, and stored at 4° in sodium chloride and glucose solution for 24 hours," *Transfusion*, 40(11):1341-1345 (2000).

Wang et al., "Transfusion of older stored blood worsens outcomes in canines depending on the presence and severity of pneumonia," *Transfusion*, 54(7):1712-2417 (2014).

Weinberg et al., "Red blood cell age and potentiation of transfusion-related pathology in trauma patients," *Transfusion*, 51(4):867-873 (2011).

Wither et al., "Hemoglobin oxidation at functional amino acid residues during routine storage of red blood cells," *Transfusion*, 56(2)421-426 (2015).

Yoshida et al., "Extended storage of red blood cells under anaerobic conditions," *Vox Sanguinis*, 92(1):22-31 (2007).

Yoshida et al., "The effects of additive solution pH and metabolic rejuvenation on anaerobic storage of red cells," *Transfusion*, 48(10):2096-2105 (2008).

Yoshida et al. "Reduction of microparticle generation during anaerobic storage of red blood cells," *Transfusion*, 52:83A (2012).

Zhang et al., "Lactate clearance is a useful biomarker for the prediction of all- cause mortality in critically ill patients: a systematic review and meta-analysis," *Critical Care Medicine*, 42(9):2118-2125 (2014).

Zhu et al., "Impaired adenosine-5' triphosphate release from red blood cells promotes their adhesion to endothelial cells: a mechanism of hypoxemia after transfusion," *Critical Care Medicine*, 39(11):2478-2486 (2011).

Zimring, "Established and theoretical factors to consider in assessing the red cell storage lesion," *Blood*, 125(14):2185-2190 (2015).

Search Report dated Dec. 4, 2023 issued in Chinese Appln. 201980079192.0.

He et al., "24. Effect of Active Oxygen on the Rheological Properties of Red Aluminum, Its Mechanism and Its Electrochemical Significance," *Clinical Cytorheology*, 1st Edition, p. 346 (Aug. 1997) (Chongqing, China) (with machine translation).

Hu et al., "18. Pleural Effusion and ascites," *SIFIC Guide to Clinical Practices in Infection Prevention and Control*, 1st Edition, p. 135 (May 2013) (Shanghai, China) (with machine translation).

*Journal of the Japanese Society of Internal Medicine* 100(12), pp. 3522-3526 (Dec. 2011).

* cited by examiner

Week 3 - recovery

*P<0.05 vs control
+P<0.05 vs Sham

FIG. 11A

Liver CXCL1

Urinary neutrophil gelatinase-associated lipocalin (u-NGAL)

IL-6

METHODS FOR MANAGING ADVERSE EVENTS IN PATIENTS WITH INFLAMMATION

CROSS REFERENCE TO RELATED APPLICATION

This application is a continuation of U.S. application Ser. No. 17/272,597, filed May 10, 2021, now U.S. Pat. No. 12,447,177, which is a U.S. National Stage of International Application No. PCT/US2019/061565, filed Nov. 14, 2019, which claims priority from U.S. Provisional Patent Application Ser. No. 62/768,667, filed Nov. 16, 2018, each of which are incorporated by reference herein in their entireties.

GOVERNMENT RIGHTS

This invention was made with the United States government support under R44HL132172 awarded by the National Heart, Lung, and Blood Institute. The government has certain rights in the invention.

FIELD OF THE INVENTION

The present disclosure relates to treatment of inflammation, sickle cell disease, trauma, and hemorrhagic shock.

BACKGROUND OF THE INVENTION

Sickle cell disease (SCD), a group of inherited red blood cell disorders, affects millions of people throughout the world. It is estimated that SCD affects approximately 100,000 Americans.

Sickle cell disease is divided into 6 types, sickle cell anemia (HbSS), sickle-hemoglobin C disease (HbSC), hemoglobin S-beta-thalassemia ((HbSβ0 and Hbβ+ thalassemia), hemoglobin-SD disease (HbSD), hemoglobin-SE disease (HbSE), and hemoglobin-SO Arab disease (HbSO). The most severe form, HbSS, is characterized by the inheritance of two sickle cell genes. In HbSC, a single sickle cell gene is inherited from one parent and an abnormal gene for hemoglobin C from the other parent. HbSC is a milder form of the disease. People with HbS beta thalassemia inherit one sickle gene and a gene for beta thalassemia. HbS beta thalassemia is further divided into beta thalassemia O and beta thalassemia +, with beta thalassemia O being the more severe form of the two. HbSD, HbSE, and HbSO are rare types of sickle cell disease. In the rare types, a sickle cell gene and one gene from an abnormal type of hemoglobin (D, E, or O) are inherited.

Some of the most common complications of SCD includes vaso-occlusion. Studies have shown that sickle RBCs (SS-RBCs) initiate vaso-occlusive episodes by adhesive interactions with the endothelium. Vaso-occlusion episodes cause various degrees of pain dependent on the person. This pain can begin suddenly and remain for any period of time. Patients are also more likely to experience infections including flu, meningitis, and hepatitis. Patients can also experience hand-foot syndrome, eye disease, acute chest syndrome, and stroke. Further, studies have shown that sickle cell disease promotes an inflammatory response. See Plat, O., "Sickle cell anemia as an inflammatory disease," *J. Clin. Invest.,* 106(3): 337-338 (2000). Over a lifetime, SCD can harm a patient's brain, eyes, heart, lung, liver, spleen, kidneys, skin, joints, and bones.

Treatments for sickle cell disease include blood transfusions, bone marrow transplant, stem cell transplant, and medications to reduce the number of painful episodes of crisis (e.g., hydroxyurea).

In 2010, there were 5.1 million deaths from injuries, surpassing the number of deaths due to HIV, tuberculosis, and malaria combined (3.8 million). See Norton, et al., "Global Health Injuries" in *The NEJM,* 368:1723-30 (2013) ("Norton 2013") (hereby incorporated by reference in its entirety). Injuries include unintentional injuries (e.g., road-traffic incidents, falls, and burns) and intentional injuries (e.g., self-harm, interpersonal violence, war and conflict). See Norton 2013. The number of deaths from injuries increased by 24% between 1990 and 2010, worldwide, and increased 23% between 2000 and 2010, in the United States. See Norton 2013. Additionally, at least 20% of all trauma deaths are the result of survivable injuries and are therefore preventable with optimal care. Fox et al., "Earlier Endpoints are Required for Hemorrhagic Shock Trials Among Severely Injured Patients." *Shock,* 47:567-73 (2017) (hereby incorporated by reference in its entirety). The percentage of preventable deaths make it imperative to develop therapy for avoidable complications which lead to mortality.

Penetrating wounds (e.g., gunshot or stabbing) and blunt trauma (e.g., fall or automobile accident) are major causes of hemorrhagic trauma. The resulting shock is a condition of inadequate oxygen supply to tissues from massive hemorrhage causing oxygen debt, anaerobic metabolism and raise of plasma lactate level. Failure to reverse shock by restoring circulation and oxygen delivery can result in permanent tissue damage, multiple organ failure and mortality.

Clinical sequelae of hemorrhagic trauma and shock include mortality from exsanguination within several hours of trauma, as well as after 24 hours from morbidity from trauma and massive transfusion. Such morbidity includes multiple organ failure including lung, kidney, liver from acute traumatic coagulopathy or inflammation, and infection/sepsis from transfusion related immune modulation; both morbidities are heightened by lower quality of transfused blood products as well as higher volume of transfused pRBC.

One approach for treating hemorrhage shock is the use of crystalloids for resuscitation. However, the use of crystalloids result in increased morbidity and mortality by causing trauma induced coagulopathy. For at least this reason, early administration of blood components is advocated for reversing shock caused by hemorrhagic trauma. Packed red blood cells (pRBCs) are transfused into a hemorrhagic trauma patient to restore lost blood volume, restore oxygen carrying capacity in patients and restore oxidative metabolism in tissue from anaerobic metabolism. However, the use of pRBCs is not without risk of complications, including antigen mismatch, pathogen transmission, circulatory overload, and degradation of pRBCs during ex vivo storage.

When stored conventionally, stored blood undergoes a steady deterioration which is associated with various storage lesions including, among others, hemolysis, hemoglobin degradation, and reduced ATP and 2,3-DPG concentrations. When transfused into a patient, the effects of the steady deterioration during storage manifest, for example, as a reduction in the 24-hour in vivo recovery. The rapid decrease in the hematocrit that results from reduced 24-hour recovery, when severe, can result in delayed hemolytic transfusion reaction (DHTR). Other complications, for example systemic inflammatory response syndrome (SIRS), transfusion related acute lung injury (TRALI), and transfusion related immunomodulation (TRIM) are associated with transfusion of stored blood, though identification of the underlying causes has remained unclear.

Even when transfused within the current 6-week limit, stored RBCs tend to exhibit lower quality (e.g. increased fraction of RBCs removed; compromised oxygen exchange capacity; reduced deformability) and increased toxicity, often manifested as the clinical sequelae of transfusion therapy. A large and growing number of articles in the literature supports this view. See Zimring, "Established and theoretical factors to consider in assessing the red cell storage lesion," *Blood*, 125:2185-90 (2015); Zhu et al., "Impaired adenosine-5'-triphosphate release from red blood cells promotes their adhesion to endothelial cells: a mechanism of hypoxemia after transfusion," *Critical care medicine*, 39:2478-86 (2011); Weinberg et al., "Red blood cell age and potentiation of transfusion-related pathology in trauma patients," *Transfusion*, 51:867-73 (2011); Spinella et al., "Does the storage duration of blood products affect outcomes in critically ill patients?" *Transfusion* 51:1644-50 (2011); Roback et al., "Insufficient nitric oxide bioavailability: a hypothesis to explain adverse effects of red blood cell transfusion," *Transfusion*, 51:859-66 (2011); Reynolds et al., "The transfusion problem: role of aberrant S-nitrosylation," *Transfusion*, 51:852-8 (2011); Kim-Shapiro et al., "Storage lesion: role of red blood cell breakdown," *Transfusion*, 51:844-51 (2011); Jy et al., "Microparticles in stored red blood cells as potential mediators of transfusion complications," *Transfusion*, 51:886-93 (2011); Hod et al., "Transfusion of human volunteers with older, stored red blood cells produces extravascular hemolysis and circulating non-transferrin-bound iron," *Blood*, 118:6675-82 (2011); Flegel et al., "Does prolonged storage of red blood cells cause harm?" *British journal of haematology* 165:3-16 (2014); Redlin et al., "Red blood cell storage duration is associated with various clinical outcomes in pediatric cardiac surgery," *Transfusion medicine and hemotherapy: offizielles* Organ der Deutschen Gesellschaft fur Transfusionsmedizin and Immunhamatologie 41:146-51 (2014); Rogers et al., "Storage duration of red blood cell transfusion and *Clostridium difficile* infection: a within person comparison," *PLoS One* 9:e89332 (2014); Spinella et al., "Properties of stored red blood cells: understanding immune and vascular reactivity," *Transfusion* 51:894-900 (2011); Brown et al., "Length of red cell unit storage and risk for delirium after cardiac surgery," *Anesth Analg*, 119:242-50 (2014); Wang et al., "Transfusion of older stored blood worsens outcomes in canines depending on the presence and severity of pneumonia," *Transfusion*, 54:1712-24 (2014); Liu et al., "Mechanism of faster NO scavenging by older stored red blood cells," *Redox biology*, 2:211-9 (2014); Prestia et al., "Transfusion of stored blood impairs host defenses against Gramnegative pathogens in mice," *Transfusion* 54:2842-51 (2014); D'Alessandro et al., "An update on red blood cell storage lesions, as gleaned through biochemistry and omics technologies," *Transfusion*, 55:205-19 (2015) (hereby incorporated by reference in their entireties). An extensive body of in vitro studies unequivocally shows the degradation of RBCs (storage lesions) during conventional storage. A body of emerging metabolomic studies show the development of storage lesions at the molecular level. See Roback et al., "Metabolomics of AS-1 RBCs Storage," *Transfusion medicine reviews* (2014); D'Alessandro et al., "Metabolomics of AS-5 RBCs supernatants following routine storage," *Vox sanguinis* (2014); D'Alessandro et al., "Routine storage of red blood cell (RBC) units in additive solution-3: a comprehensive investigation of the RBC metabolome," *Transfusion* 55:1155-68 (2015); D'Alessandro et al., "Red blood cell storage in additive solution-7 preserves energy and redox metabolism: a metabolomics approach," *Transfusion* (2015); Wither et al., "Hemoglobin oxidation at functional amino acid residues during routine storage of red blood cells," *Transfusion* (2015); D'Alessandro et al., "Citrate metabolism in red blood cells stored in additive solution-3," *Transfusion* (2016); D'Alessandro et al., "Omics markers of the red cell storage lesion and metabolic linkage," *Blood Transfus*, 15:137-44 (2017) (hereby incorporated by reference in their entireties). There is a need for reducing or preventing this degradation to increase the efficacy of transfusions (more $O_2$ delivery to peripheral tissues immediately after transfusion) and to reduce mortality due to inflammation, sickle cell disease, or hemorrhagic trauma.

Oxidative damage initiates many RBC storage lesions in conventionally stored blood and their downstream consequences; thus, methods to reduce the extent of oxidative stress are required to reduce the RBC storage lesions. A number of approaches have been developed aimed at minimizing storage lesions and improving transfusion outcomes. Approaches include additive solutions (for example, U.S. Pat. No. 4,769,318 to Hamasaki et al. and U.S. Pat. No. 4,880,786 to Sasakawa et al. U.S. Pat. No. 6,447,987 to Hess et al.), frozen storage (see U.S. Pat. No. 6,413,713 to Serebrennikov Chaplin et al., "Blood Cells for Transfusion," *Blood*, 59: 1118-20 (1982), and Valeri et al., "The survival, function, and hemolysis of human RBCs stored at 4 degrees C. in additive solution (AS-1, AS-3, or AS-5) for 42 days and then biochemically modified, frozen, thawed, washed, and stored at 4 degrees C. in sodium chloride and glucose solution for 24 hours," *Transfusion*, 40:1341-5 (2000)) (hereby incorporated by reference in their entireties).

One approach that has proven successful in improving blood quality and extending its utility is through the depletion of oxygen and storage under anaerobic conditions. Among the benefits of storing blood under oxygen depleted conditions are improved levels of ATP and 2,3-DPG, and reduced hemolysis. U.S. Pat. No. 5,624,794 to Bitensky et al., U.S. Pat. No. 6,162,396 to Bitensky et al., and U.S. Pat. No. 5,476,764 to Bitensky (hereby incorporated by reference in their entireties) are directed to the storage of red blood cells under oxygen-depleted conditions. U.S. Pat. No. 5,789,151 to Bitensky et al. is directed to blood storage additive solutions (hereby incorporated by reference in its entirety). U.S. Pat. No. 6,162,396 to Bitensky et al. (the '396 patent) (hereby incorporated by reference in its entirety) discloses anaerobic storage bags for blood storage that comprise an oxygen impermeable outer layer, a red blood cell (RBCs) compatible inner layer that is permeable to oxygen, and having an oxygen scrubber placed between the inner and outer layers.

Storing blood under oxygen depleted conditions can also result in reduced microparticle levels, reductions in the loss of deformability, reduced lipid and protein oxidation and higher post transfusion survival when compared to blood stored under conventional conditions. See Yoshida et al., "The effects of additive solution pH and metabolic rejuvenation on anaerobic storage of red cells," Transfusion 48:2096-2105 (2008) and Yoshida, T., et al. "Reduction of microparticle generation during anaerobic storage of red blood cells. Transfusion", 52, 83A (2012) (hereby incorporated by reference in their entireties). Anaerobically stored RBCs further provide higher 24-hour in vivo recovery after autologous transfusion, higher 2,3-DPG and ATP levels, lower hemolysis, and beneficial remodeling of metabolic pathway. See Reisz et al. "Oxidative modifications of glyceraldehyde 3-phosphate dehydrogenase regulate metabolic reprogramming of stored red blood cells," *Blood,* 128:e32-42 (2016); and Yoshida et al., "Extended storage of red blood cells under anaerobic conditions," *Vox sanguinis* 92:22-31 (2007) (hereby incorporated by reference in their entireties).

In the present disclosure, we demonstrate that oxygen reduced (OR) or oxygen and carbon dioxide reduced (OCR) red blood cells can reduce blood vessel blockage in SCD patients by reducing adhesion to thrombospondin. We also demonstrate that OR and OCR red blood cells have reduced hemolysis in the presence of plasma from SCD patients compared to conventionally stored blood.

In the present disclosure, we demonstrate that OR or OCR blood from rats provides improved ATP and 2,3-DPG during storage compared to conventionally stored blood, as has been previously demonstrated using human blood. Thus, OR or OCR rat RBCs are expected to have similar reductions in microparticles, improved deformability, reduced lipid and protein oxidation and higher post transfusion survival.

Here we demonstrate for the first time that OR and OCR blood in rats provides for surprising improvements in clinical outcomes when transfused to treat hemorrhagic trauma. Using a rat hemorrhagic shock resuscitation model, we show that OR or OCR RBCs provide for reduced organ damage relative to conventionally stored blood. In addition, OR or OCR RBCs provide for reversal of the shock state using smaller pRBC volumes. Finally, OR or OCR RBCs, when transfused to treat hemorrhagic shock more rapidly stabilized hemodynamics compared to conventionally stored pRBC of same storage duration.

OR and OCR RBCs provide for improved methods for treatment of trauma resulting in exsanguination to reduce mortality and morbidity over conventionally stored blood. OR and OCR RBCs provide for reduced organ failure, including reductions in levels of markers of lung and liver damage. OR and OCR RBCs further provide reductions in the amounts of blood necessary to restore and stabilize hemodynamic function. Thus, OR and OCR RBCs can provide for reducing the volume of RBCs required for transfusion therapy when treating hemorrhagic trauma. The improved quality of OR and OCR, in addition to the previously demonstrated improvements to the ability of stored RBCs to deliver oxygen, also provides for unexpected reductions in organ damage, morbidity, and mortality associated with trauma.

SUMMARY OF THE INVENTION

The present disclosure provides for, and includes, a method of treating a patient in need thereof with stored oxygen reduced blood having an oxygen saturation of 20% or less during storage, wherein the patient in need thereof has inflammation.

The present disclosure provides for, and includes, a method of improving transfusion in a sickle cell patient in need thereof comprising providing stored oxygen reduced blood to a patient having sickle cell disease, wherein the oxygen reduced blood has an oxygen saturation of 20% or less during storage.

The present disclosure provides for, and includes, a method of decreasing the number of vaso-occlusion episodes in a patient in need thereof comprising providing stored oxygen reduced blood to a patient in need thereof, wherein the oxygen reduced blood has an oxygen saturation of 20% or less during storage and the decreasing vaso-occlusion episodes comprises decreasing adhesion of red blood cells to endothelial cells.

The present disclosure provides for, and includes, a method of decreasing red blood cell adhesion to endothelial cells in a patient in need thereof comprising providing stored oxygen reduced blood to a patient having sickle cell disease, wherein the oxygen reduced blood has an oxygen saturation of 20% or less during storage.

BRIEF DESCRIPTION OF THE DRAWINGS

The present disclosure is provided with reference to the accompanying drawings, wherein:

FIGS. 11A and 11B are graphs presenting the results of an exemplary embodiment according to the present disclosure, providing a comparison of the amount of serum creatinine in animals resuscitated with control, OR-RBCs, and OCR-RBCs stored for 1 week (FIG. 11A) or 3 weeks (FIG. 11B).

Figure 1:
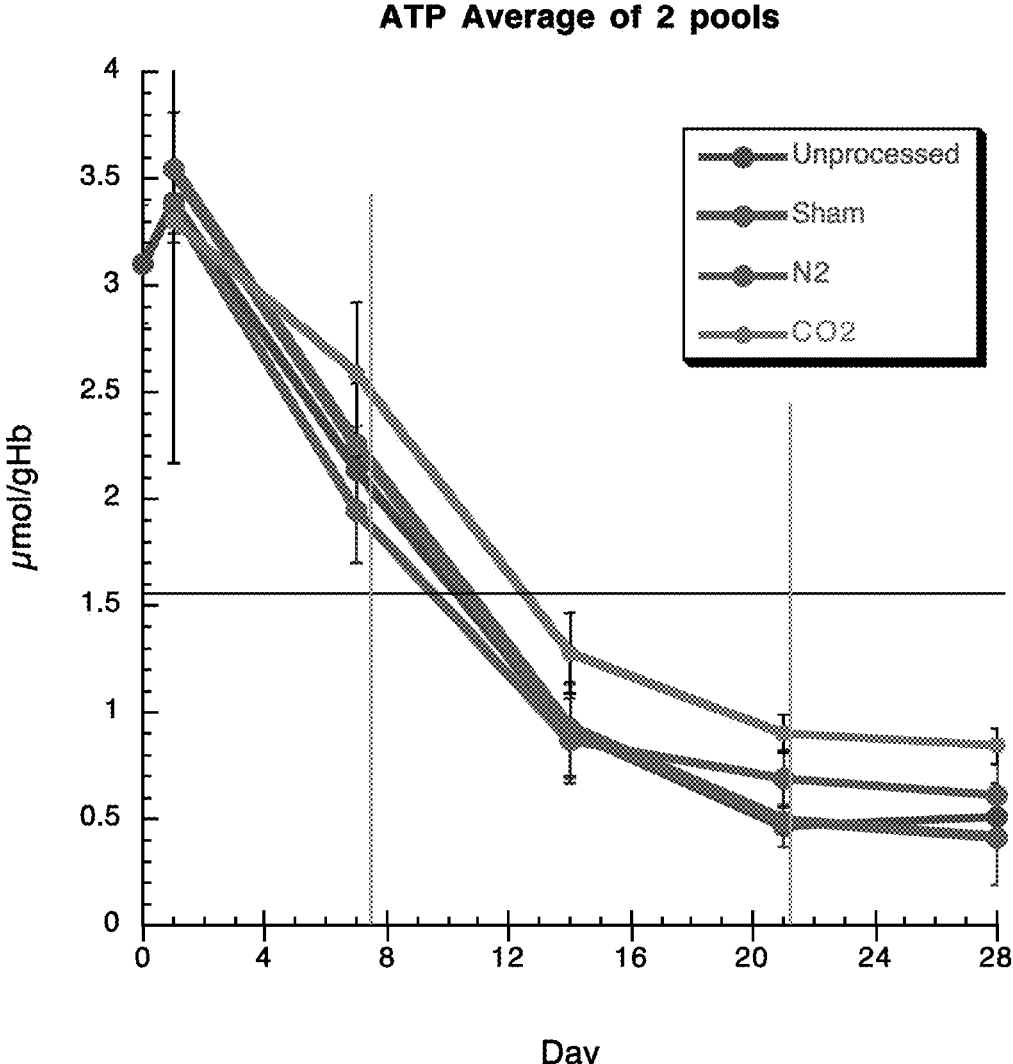
FIG. 1 is a graph presenting the results of an exemplary embodiment according to the present disclosure, comparing ATP levels in conventionally stored RBCs (unprocessed; control), sham control (SC), oxygen reduced RBCs ($N_2$; OR), and oxygen and carbon dioxide reduced RBCs ($CO_2$; OCR).

The examples set out herein illustrate(s) several embodiment(s) of the present disclosure but should not be construed as limiting the scope of the present disclosure in any manner.

DETAILED DESCRIPTION

Methods of the present disclosure provide for, and include, providing a hemorrhagic patient with oxygen reduced stored blood that has an oxygen saturation of 20% or less prior to and during storage. Methods also provide for providing a hemorrhagic patient with oxygen reduced stored blood that has an oxygen saturation of between 15 and 20% prior to and during storage. Methods also provide for providing a hemorrhagic patient with oxygen reduced stored blood that has an oxygen saturation of between 10 and 15% prior to and during storage. Methods also provide for providing a hemorrhagic patient with oxygen reduced stored blood that has an oxygen saturation of between 5 and 10% prior to and during storage. Methods also provide for providing a hemorrhagic patient with oxygen reduced stored blood that has an oxygen saturation of between 3 and 5% prior to and during storage.

Methods also provide for providing oxygen reduced stored blood that has an oxygen saturation of 20% or less prior to and during storage for transfusion to a person having hemorrhagic shock. Methods also provide for providing oxygen reduced stored blood that has an oxygen saturation of 20% or less prior to and during storage for transfusion to a person having hemorrhagic trauma. Also included are methods comprising transfusing oxygen reduced stored blood that has an oxygen saturation of 20% or less prior to and during storage to a patient having an increased risk of trauma due to surgery. Methods providing oxygen reduced stored blood having an initial oxygen saturation of 20% or less include providing oxygen reduced stored blood having an initial oxygen saturation of 10% or less. Methods of providing oxygen reduced stored blood having an initial oxygen saturation of 20% or less further include providing oxygen reduced stored blood having an initial oxygen saturation of 5% or less. Methods of providing oxygen reduced stored blood having an initial oxygen saturation of 20% or less further include providing oxygen reduced stored blood having an initial oxygen saturation of 3% or less.

Methods of the present disclosure provide for, and include, providing oxygen reduced stored blood for the treatment of trauma having an oxygen saturation of 20% or less prior to and during storage for a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of 15% or less after a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of 10% or less after a storage period of at least one week, at least two weeks, at least 3 weeks, at least 4 weeks, at least 5 weeks, or at least 6 weeks. Methods further provide for providing oxygen reduced stored blood for the treatment of trauma having an oxygen saturation of 5% or less after a storage period of at least one week, at least two weeks, at least 3 weeks, at least 4 weeks, at least 5 weeks, or at least 6 weeks. Methods further provide for providing oxygen reduced stored blood for the treatment of trauma having an oxygen saturation of 3% or less after a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of between 3 and 5% after a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of between 5 and 10% after a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of between 10 and 15% after a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of between 15 and 20% after a storage period of at least one week, at least two weeks, at least 3 weeks, at least 4 weeks, at least 5 weeks, or at least 6 weeks.

Methods of the present disclosure provide for, and include, providing a trauma patient with oxygen reduced stored blood that has an oxygen saturation of 20% or less prior to and during storage. In an aspect, a trauma patient suffers from a head trauma, a penetrating wound, blunt force trauma, injury due to a fall, or injury due to a car accident. In another aspect, a trauma patient is a hemorrhagic trauma patient. In yet another aspect, a trauma patient is hemorrhagic due to surgery, a penetrating wound, blunt force trauma, an injury due to a fall, or an injury due to a car accident.

In an aspect of the present disclosure, a trauma patient or hemorrhagic trauma patient is a subject in need of OR and OCR stored blood. In aspects of the present disclosure, a trauma patient is a hemorrhagic trauma patient in need of one or more units of blood as transfusion therapy. In aspects of the present disclosure, a trauma patient is a hemorrhagic trauma patient in need of two or more units of blood as transfusion therapy. In aspects of the present disclosure, a trauma patient is a hemorrhagic trauma patient in need of three or more units of blood as transfusion therapy.

In an aspect of the present disclosure, a trauma patient is a patient in hemorrhagic shock. In an aspect, a trauma patient is in hemorrhagic shock due to a head trauma, a penetrating wound, blunt force trauma, injury from a fall, or injury from a car accident. In aspects of the present disclosure, a hemorrhagic trauma patient is a patient with a class I hemorrhage. In another aspect, a hemorrhagic trauma patient is a patient with a class II hemorrhage. In another aspect, a hemorrhagic trauma patient is a patient with a class III hemorrhage. In another aspect, a hemorrhagic trauma patient is a patient with a class IV hemorrhage. In an aspect of the present disclosure, a hemorrhagic trauma patient loses up to 15% of blood volume. In another aspect, a hemorrhagic trauma patient loses between 15 and 30% of blood volume. In another aspect, a hemorrhagic trauma patient loses between 30 and 40% of blood volume. In a further, a hemorrhagic trauma patient loses greater than 40% of blood volume.

The present disclosure provides for, and includes, a patient in need of transfusion therapy with OR or OCR RBCs exhibits one or more signs selected from the group consisting of decreased mean arterial pressure, a decreased hematocrit, increased lactate, increased glucose, increased aspartate aminotransferase (AST), increased alanine amino-transferase (ALT), increased urine neutrophil gelatinase-associated lipocalin (u-NGAL), increased serum creatinine, and increased blood urea nitrogen. In an aspect of the present disclosure, a patient in need of transfusion therapy with OR or OCR RBCs is a hemorrhagic trauma patient having a decreased mean arterial pressure. The present disclosure provides for, and includes, a patient in need of transfusion therapy with OR or OCR RBCs exhibits increased aspartate aminotransferase (AST) and increased alanine aminotransferase (ALT). The present disclosure provides for, and includes, a patient in need of transfusion therapy with OR or OCR RBCs exhibits decreased mean arterial pressure and increased lactate. The present disclosure provides for, and includes, a patient in need of transfusion therapy with OR or OCR RBCs exhibits increased aspartate aminotransferase (AST), increased alanine amino-transferase (ALT), and increased blood urea nitrogen. The present disclosure provides for, and includes, a patient in need of transfusion therapy with OR or OCR RBCs exhibits increased aspartate aminotransferase (AST), increased ala-nine aminotransferase (ALT), increased serum creatinine, and increased blood urea nitrogen. The present disclosure provides for, and includes, a patient in need of transfusion therapy with OR or OCR RBCs exhibits increased lactate and increased glucose. The present disclosure provides for, and includes, a patient in need of transfusion therapy with OR or OCR RBCs exhibiting increased urine neutrophil gelatinase-associated lipocalin (u-NGAL), increased serum creatinine, and increased blood urea nitrogen.

In another aspect, a patient in need of transfusion therapy with OR or OCR RBCs is a hemorrhagic trauma patient having a decreased hematocrit. In another aspect, a patient in need of transfusion therapy with OR or OCR RBCs is a hemorrhagic trauma patient having increased lactate. In yet another aspect, a patient in need of transfusion therapy with OR or OCR RBCs is a hemorrhagic trauma patient having increased glucose. In a further aspect, a hemorrhagic trauma patient having increased in aspartate aminotransferase (AST). In another aspect, a patient in need of transfusion therapy with OR or OCR RBCs is a hemorrhagic trauma patient having increased alanine aminotransferase (ALT). In another aspect, a patient in need of transfusion therapy with OR or OCR RBCs is a hemorrhagic trauma patient having increased urine neutrophil gelatinase-associated lipocalin (u-NGAL). In another aspect, a patient in need of transfusion therapy with OR or OCR RBCs is a hemorrhagic trauma patient having increased serum creatinine. In another aspect, a patient in need of transfusion therapy with OR or OCR RBCs is a hemorrhagic trauma patient having increased blood urea nitrogen.

In an aspect of the present disclosure, the OR and OCR stored blood for use in transfusion therapy of a patient in need thereof has an initial oxygen saturation of 20% or less. In another aspect, OR and OCR stored blood has an initial oxygen saturation of 10% or less. In another aspect, OR and OCR stored blood has an initial oxygen saturation of 5% or less. In another aspect, OR and OCR stored blood has an initial oxygen saturation of 3% or less.

In an aspect of the present disclosure, the OCR stored blood for use in transfusion therapy of a patient in need thereof has an initial $pCO_2$ (at 37° C.) of between 10 and 40 mmHg. In another aspect, OCR stored blood has an initial $pCO_2$ of between 10 and 30 mmHg. In another aspect, OCR stored blood has an initial $pCO_2$ of between 10 and 20 mmHg. In another aspect, OCR stored blood has an initial $pCO_2$ of between 10 and 15 mmHg. In yet another aspect, OCR stored blood has an initial $pCO_2$ of less than 10 mmHg.

In an aspect of the present disclosure, OR and OCR stored blood for use in transfusion therapy of a patient in need thereof has an initial oxygen saturation of 20% or less and is stored for less than 2 days. In an aspect, OR and OCR stored blood has an initial oxygen saturation of 20% or less is stored for less than 7 days. In another aspect, OR and OCR stored blood having an initial oxygen saturation of 20% or less is stored for less than 14 days. In another aspect, oxygen reduced stored blood has an initial oxygen saturation of 20% or less and is stored for less than 21 days. In another aspect, oxygen reduced stored blood for use in transfusion therapy of a patient in need thereof has an initial oxygen saturation of 20% or less and is stored for less than 28 days. In another aspect, oxygen reduced stored blood has an initial oxygen saturation of 20% or less and is stored for less than 35 days. In another aspect, oxygen reduced stored blood has an initial oxygen saturation of 20% or less and is stored for less than 42 days. In another aspect, oxygen reduced stored blood has an initial oxygen saturation of 20% or less and is stored for less than 45 days. In an aspect of the present disclosure, OR and OCR stored blood has an oxygen saturation of 20% or less during storage.

Suitable blood for use in transfusion therapy of a patient in need thereof comprise oxygen reduced stored blood having an anticoagulant. In an aspect of the present disclosure, oxygen reduced red blood cells is stored for up to 3 weeks to produce oxygen reduced stored blood. In another aspect, oxygen reduced stored blood usually further comprises an additive solution. Suitable additive solutions according to the present disclosure include AS-1, AS-3 (Nutricel®), AS-5, SAGM, PAGG-SM, PAGG-GM, MAP, AS-7, ESOL-5, EAS61, OFAS1, OFAS3, and combinations thereof. In an aspect, the additive solution is added at the time of component separation. In an aspect, the additive solution is AS-1. In another aspect, the additive solution is AS-3. In other aspects, the additive solution is SAGM.

Methods of the present disclosure provide for, and include, increasing the mean arterial pressure (MAP) in a hemorrhagic trauma patient in need of transfusion therapy comprising providing a trauma patient with oxygen reduced stored blood that has an oxygen saturation of 20% or less prior to and during storage. In an aspect, the mean arterial pressure is increased by between 20 and 60%. In another aspect, the mean arterial pressure is increased by between 30 and 60%. In another aspect, the mean arterial pressure of a trauma patient receiving transfusion therapy of OR or OCR blood is increased by between 30 and 50%. In yet another aspect, the mean arterial pressure is increased by between 30 and 60%. In a further aspect, the mean arterial pressure of a trauma patient receiving transfusion therapy of OR or OCR blood is increased by between 30 and 40%. In an aspect, the mean arterial pressure is increased by at least 10, 20, 30, 40, 50, 60, 70, 80, or 90% more than the mean arterial pressure of a patient transfused with conventionally stored blood.

In an aspect of the present disclosure, the mean arterial pressure of a patient receiving transfusion therapy of OR or OCR blood is increased by at least 1.5 fold. In another aspect, the mean arterial pressure of a trauma patient receiving transfusion therapy of OR or OCR blood is increased by at least 2 fold. In a further aspect, the mean arterial pressure of a patient receiving transfusion therapy of OR or OCR blood is increased by between 1 and 2 fold. In an aspect of the present disclosure, the mean arterial pressure of a trauma patient receiving transfusion therapy of OR or OCR blood is increased by at least 10 mmHg, at least 20 mmHg, at least 30 mmHg, at least 40 mmHg, at least 50 mmHg, or at least 60 mmHg. In another aspect, the mean arterial pressure of a trauma patient receiving transfusion therapy of OR or OCR blood is increased by between 20 and 50 mmHg. In a further aspect, the mean arterial pressure of a patient receiving transfusion therapy of OR or OCR blood is increased by between 30 and 50 mmHg.

Methods of the present disclosure provide for, and include, increasing the mean arterial pressure in a trauma patient in need of transfusion therapy to between 70 and 110 mmHg comprising providing a trauma patient with oxygen reduced stored blood that has an oxygen saturation of 20% or less prior to, and during storage. In another aspect, the mean arterial pressure of a trauma patient receiving transfusion therapy of OR or OCR blood is increased to at least 70 mmHg. In another aspect, the mean arterial pressure of a trauma patient receiving transfusion therapy of OR or OCR blood is increased to at least 80 mmHg. In yet another aspect, the mean arterial pressure is increased to at least 90 mmHg. In a further aspect, the mean arterial pressure is increased to at least 100 mmHg. In an aspect of the present disclosure, the mean arterial pressure in a subject in need thereof remains between 70 and 110 mmHg for at least 1 hour after transfusion. In another aspect, the mean arterial pressure remains between 70 and 110 mmHg for at least 2 hours after transfusion. In yet another aspect, the mean arterial pressure remains between 70 and 105 mmHg for at least 3 hours after transfusion. In another aspect, the mean arterial pressure remains between 70 and 110 mmHg for at least 4 hours after transfusion. In another aspect, the mean arterial pressure remains between 70 and 110 mmHg for at least 5 hours after transfusion.

Methods of the present disclosure provide for, and include, increasing the mean arterial pressure in a trauma patient in need of transfusion therapy at a rate faster than the mean arterial pressure of a patient transfused with conventionally stored blood comprising providing a trauma patient with oxygen reduced stored blood that has an oxygen saturation of 20% or less prior to and during storage. In an aspect, the mean arterial pressure of a patient transfused with OR or OCR blood is restored to within normal physiologic parameters in half the time when compared to conventionally stored blood.

Methods of the present disclosure provide for, and include, reducing the amount of stored blood needed for transfusion in a hemorrhagic trauma patient in need of transfusion therapy comprising providing a trauma patient with oxygen reduced stored blood that has an oxygen saturation of 20% or less prior to and during storage. In an aspect, the amount of OR stored blood needed for transfusion is between 10 and 90% less than the amount of conventionally stored blood needed. In another aspect, the amount of OR stored blood needed for transfusion is between 10 and 30% less than the amount of conventionally stored blood needed. In another aspect, the amount of OR stored blood needed for transfusion is between 20 and 50% less than the amount of conventionally stored blood needed. In another aspect, the amount of OR stored blood needed for transfusion is between 20 and 80% less than the amount of conventionally stored blood needed. In another aspect, the amount of OR stored blood needed for transfusion is between 30 and 80% less than the amount of conventionally stored blood needed. In yet another aspect, the amount of OR stored blood needed for transfusion is between 40 and 85% less than the amount of conventionally stored blood needed. In a further aspect, the amount of OR stored blood needed for transfusion is between 50 and 90% less than the amount of conventionally stored blood needed.

Methods of the present disclosure provide for, and include, reducing the amount of stored blood needed for transfusion in a hemorrhagic trauma patient in need of transfusion therapy by at least 10% less comprising providing a trauma patient with oxygen reduced stored blood that has an oxygen saturation of 20% or less prior to and during storage. In an aspect, the amount of OR stored blood needed for transfusion is at least 20% less than the amount of conventionally stored blood needed. In another aspect, the amount of OR stored blood needed for transfusion is at least 30% less than the amount of conventionally stored blood needed. In another aspect, the amount of OR stored blood needed for transfusion is at least 40% less than the amount of conventionally stored blood needed. In another aspect, the amount of OR stored blood needed for transfusion is at least 50% less than the amount of conventionally stored blood needed. In yet another aspect, the amount of OR stored blood needed for transfusion is at least 60% less than the amount of conventionally stored blood needed. In another aspect, the amount of OR stored blood needed for transfusion is at least 70% less than the amount of conventionally stored blood needed. In a further aspect, the amount of OR stored blood needed for transfusion is between about 10 and 20%, about 20 and 30%, about 30 and 40%, about 40 and 50%, about 50 and 60%, about 60 and 70%, about 70 and 80%, about 80 and 90%, or about 90 and 95% less than the amount of conventionally stored blood needed. In another aspect, the amount of OR stored blood needed for transfusion in a patient in need of transfusion therapy is between 10 and 20%, 20 and 30%, 30 and 40%, 40 and 50%, 50 and 60%, 60 and 70%, 70 and 80%, 80 and 90%, or 90 and 95% less than the amount of conventionally stored blood needed.

Figure 7A:
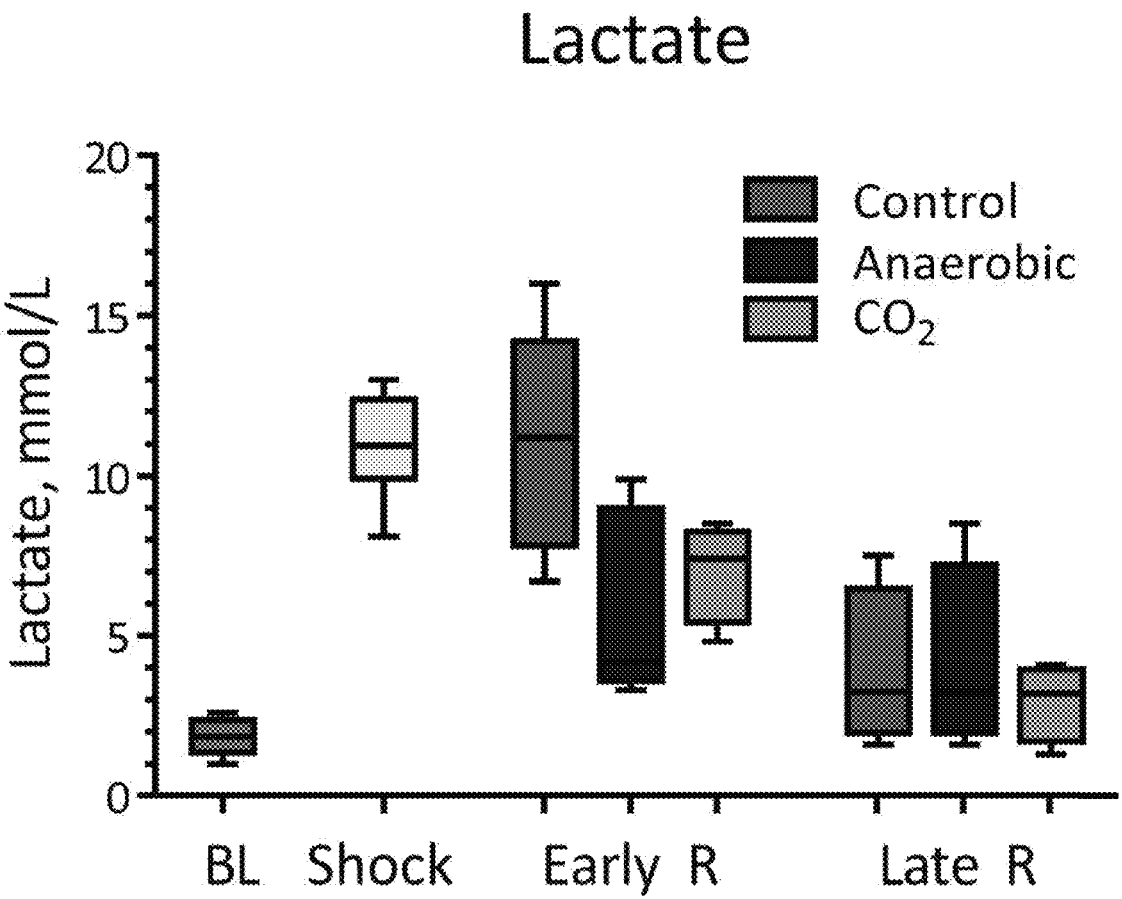
FIGS. 7A and 7B are graphs presenting the results of an exemplary embodiment according to the present disclosure, providing a comparison of the amount of lactate in animals resuscitated with control, OR-RBCs, and OCR-RBCs stored for 1 week (FIG. 7A) or 3 weeks (FIG. 7B). BL (baseline) identifies animals not under shock conditions. Shock identifies animals under hemorrhagic shock. Early R identifies a resuscitation period of 10 mins. Late R identifies a resuscitation period of 60 mins.
Figure 7B:
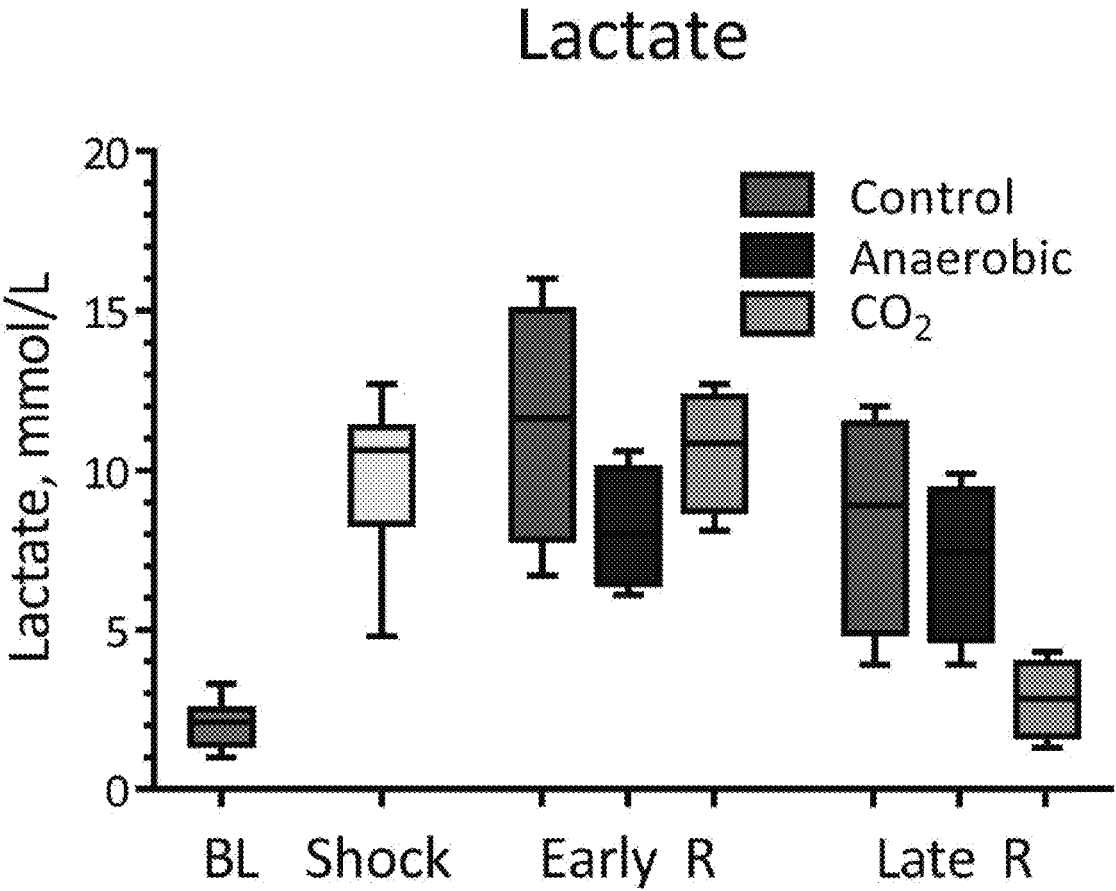

Lactate clearance is a biomarker for resuscitation from hemorrhagic shock. See Hashmi et al., "Predictors of mortality in geriatric trauma patients: a systematic review and meta-analysis," *The journal of trauma and acute care surgery*, 76:894-901 (2014); Regnier et al., "Prognostic significance of blood lactate and lactate clearance in trauma patients," *Anesthesiology*, 117:1276-88 (2012); and Zhang et al., "Lactate clearance is a useful biomarker for the prediction of all-cause mortality in critically ill patients: a systematic review and meta-analysis," *Critical care medicine*, 42:2118-25 (2014) ("Zhang 2014") (hereby incorporated by reference in their entireties). The clinical value of lactate clearance is useful in predicting the outcome of patients with septic shock and critically ill patients without evident circulatory shock. Elevated lactate is an indicator of adverse clinical outcome, and its rapid clearance is universally associated with improved outcome in heterogeneous ICU or ED patient population. See Zhang 2014. Decreased lactate levels in animals resuscitated with OR-RBCs compared to conventionally RBCs support the notion that resuscitation with OR RBCs can significantly improve patients' clinical outcome. See FIGS. 7A and 7B.

Methods of the present disclosure provide for, and include, reducing the lactate level in a patient in need of transfusion therapy comprising providing a patient with oxygen reduced (OR) stored blood that has an oxygen saturation of 20% or less prior to and during storage. In an aspect, the lactate level is reduced by between 10 and 90%. In an aspect, transfusion with OR stored blood reduces the lactate level in a patient in need of transfusion therapy by between 10 and 50%. In another aspect, transfusion with OR stored blood reduces the lactate level in a patient in need of transfusion therapy by between 20 and 40%. In another aspect, transfusion with OR stored blood reduces the lactate level in a patient in need of transfusion therapy by between 50 and 90%. In yet another aspect, transfusion with OR stored blood reduces the lactate level in a patient in need of transfusion therapy by between 60 and 90%. In another aspect, transfusion with OR stored blood reduces the lactate level in a patient in need of transfusion therapy by between 10 and 20%, 20 and 30%, 30 and 40%, 40 and 50%, 50 and 60%, 60 and 70%, 70 and 80%, or 80 and 90%. In another aspect, transfusion with OR stored blood reduces the lactate level in a trauma patient in need of transfusion therapy by at least 10%. In another aspect, transfusion with OR stored blood reduces the lactate level in a patient in need of transfusion therapy by at least 20%. In a further aspect, transfusion with OR stored blood reduces the lactate level in a patient in need of transfusion therapy by at least 30, at least 40, at least 50, at least 60, at least 70, at least 80, or at least 90%.

Methods of the present disclosure provide for, and include, reducing elevated lactate levels in a patient in need of transfusion therapy to between about 0.5 and about 2.5 mmol/L comprising providing a patient with oxygen reduced stored blood that has an oxygen saturation of 20% or less prior to and during storage. In an aspect, the lactate level in a patient in need of transfusion therapy is reduced to between about 0.9 and about 2 mmol/L. In an aspect, the lactate level in a patient in need of transfusion therapy is reduced to between about 0.9 and about 1.7 mmol/L. In another aspect, the lactate level in a patient in need of transfusion therapy is reduced to between about 1.4 and about 2.4 mmol/L. In another aspect, the lactate level in a trauma patient in need of transfusion therapy is reduced to between about 1.7 and about 2.5 mmol/L. In yet another aspect, the lactate level in a trauma patient in need of transfusion therapy is reduced to less than about 2.5 mmol/L. In a further aspect, the lactate level in a trauma patient in need of transfusion therapy is reduced to less than about 2.0 mmol/L. In another aspect, the lactate level in a trauma patient in need of transfusion therapy is reduced to less than about 1.5 mmol/L. In another aspect, the lactate level in a trauma patient in need of transfusion therapy is reduced to less than about 1.0 mmol/L. In yet another aspect, the lactate level in a trauma patient in need of transfusion therapy is reduced to between about 0.5 and about 1.0 mmol/L.

Methods of the present disclosure provide for, and include, reducing elevated lactate levels in a trauma patient in need of transfusion therapy to between 0.5 and 2.5 mmol/L comprising providing a trauma patient with oxygen reduced stored blood that has an oxygen saturation of 20% or less prior to and during storage. In an aspect, the lactate level in a patient in need of transfusion therapy is reduced to between 0.9 and 2 mmol/L. In an aspect, the lactate level in a trauma patient in need of transfusion therapy is reduced to between 0.9 and 1.7 mmol/L. In another aspect, the lactate level in a trauma patient in need of transfusion therapy is reduced to between 1.4 and 2.4 mmol/L. In another aspect, the lactate level in a trauma patient in need of transfusion therapy is reduced to between 1.7 and 2.5 mmol/L. In another aspect, the lactate level in a trauma patient in need of transfusion therapy is reduced to between 0.5 and 1 mmol/L.

Methods of the present disclosure provide for, and include, reducing elevated lactate levels in a hemorrhagic trauma patient in need of transfusion therapy to less than 4 mmol/L comprising providing a trauma patient with oxygen reduced stored blood that has an oxygen saturation of 20% or less prior to and during storage. In an aspect, the lactate level in a trauma patient in need of transfusion therapy is reduced to less than 3 mmol/L. In yet another aspect, the lactate level in a trauma patient in need of transfusion therapy is reduced to less than 2.5 mmol/L. In another aspect, the lactate level in a patient is reduced to less than 2.3 mmol/L. In another aspect, the lactate level in a trauma patient in need of transfusion therapy is reduced to less than 2 mmol/L. In another aspect, the lactate level in a trauma patient in need of transfusion therapy is reduced to less than 2 mmol/L. In another aspect, the lactate level in a trauma patient in need of transfusion therapy is reduced to less than 1.5 mmol/L. In another aspect, the lactate level in a trauma patient in need of transfusion therapy is reduced to less than 1 mmol/L.

Figure 8A:
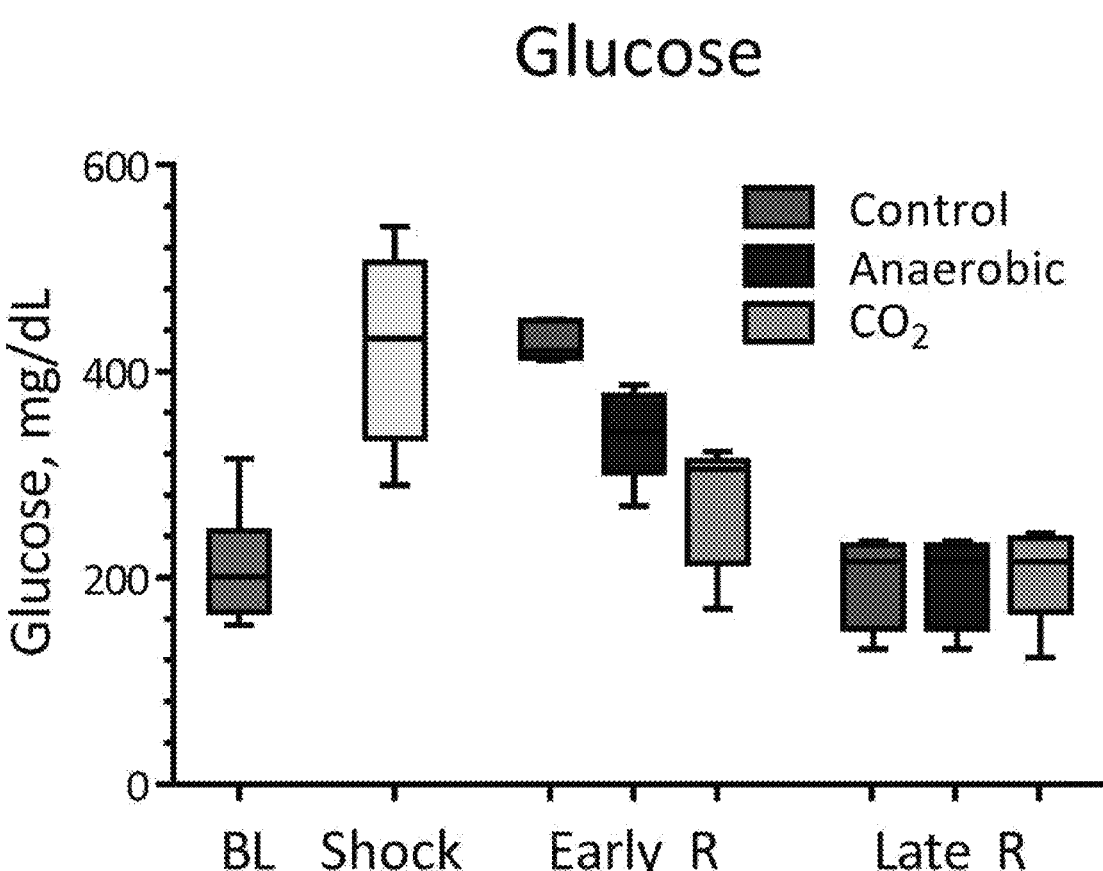
FIGS. 8A and 8B are graphs presenting the results of an exemplary embodiment according to the present disclosure, providing a comparison of the amount of glucose in animals resuscitated with control, OR-RBCs, and OCR-RBCs stored for 1 week (FIG. 8A) or 3 weeks (FIG. 8B). BL (baseline) identifies animals not under shock conditions. Shock identifies animals under hemorrhagic shock. Early R identifies a resuscitation period of 10 mins. Late R identifies a resuscitation period of 60 mins.

Blood glucose level is also known to be a predictor for outcome in several disease patterns and particularly in trauma patients. Trauma patients are more prone to poor outcome due to hyperglycemia than other critically ill patients. See Kreutziger et al., "Admission blood glucose predicted hemorrhagic shock in multiple trauma patients," *Injury,* 46:15-20 (2015) (hereby incorporated by reference in its entirety). Studies evaluating the relationship of early hyperglycemia and trauma patients examined early hyperglycemia at three possible cutoffs: glucose ≥110 mg/dL, glucose ≥150 mg/dL, and glucose ≥200 mg/dL. See Laird et al., "Relationship of early hyperglycemia to mortality in trauma patients," *J Trauma,* 56:1058-62 (2004) (hereby incorporated by reference in its entirety). A glucose level ≥200 mg/dL, is associated with significantly higher infection and mortality rates in trauma patients independent of injury characteristics. This was not true at the cutoffs of ≥110 mg/dL or ≥150 mg/dL. Decreased glucose levels in animals resuscitated with OR- and OCR-RBCs compared to conventionally RBCs support the notion that resuscitation with OR-RBCs can significantly improve patients' clinical outcome. See FIGS. 8A and 8B.

Methods of the present disclosure provide for, and include, reducing glucose in a trauma patient in need of transfusion therapy comprising providing a trauma patient with oxygen reduced (OR) stored blood that has an oxygen saturation of 20% or less prior to and during storage. In an aspect, glucose is reduced by between 10 and 90% as compared to transfusion of blood stored under conventional conditions. In an aspect, transfusion with OR stored blood reduces glucose by between 10 and 50% as compared to transfusion of blood stored under conventional conditions. In another aspect, transfusion with OR stored blood reduces glucose by between 20 and 40% as compared to transfusion of blood stored under conventional conditions. In another aspect, transfusion with OR stored blood reduces glucose by between 50 and 90% as compared to transfusion of blood stored under conventional conditions. In yet another aspect, transfusion with OR stored blood reduces glucose by between 60 and 90%. In another aspect, transfusion with OR stored blood reduces glucose by between 10 and 20%, 20 and 30%, 30 and 40%, 40 and 50%, 50 and 60%, 60 and 70%, 70 and 80%, or 80 and 90% as compared to transfusion of blood stored under conventional conditions. In another aspect, transfusion with OR stored blood reduces glucose by at least 10% as compared to transfusion of blood stored under conventional conditions. In another aspect, transfusion with OR stored blood reduces glucose by at least 20%. In a further aspect, transfusion with OR stored blood reduces glucose by at least 30, at least 40, at least 50, at least 60, at least 70, at least 80, or at least 90%.

Methods of the present disclosure provide for, and include, reducing glucose levels in a trauma patient in need of transfusion therapy to between about 70 and about 120 mg/dL comprising providing a trauma patient with oxygen reduced stored blood that has an oxygen saturation of 20% or less prior to and during storage. In an aspect, glucose in a patient after transfusion therapy with OR or OCR blood is between about 70 and about 110 mg/dL. In another aspect, glucose in a patient after transfusion therapy with OR or OCR blood is between about 70 and about 100 mg/dL. In another aspect, glucose in a trauma patient after transfusion therapy with OR or OCR blood is between about 90 and about 120 mg/dL. In another aspect, glucose in a trauma patient after transfusion therapy with OR or OCR blood is between about 90 and about 100 mg/dL.

Methods of the present disclosure provide for, and include, reducing glucose levels in a trauma patient in need of transfusion therapy to between 70 and 120 mg/dL comprising providing a trauma patient with oxygen reduced stored blood that has an oxygen saturation of 20% or less prior to and during storage. In an aspect, glucose in a patient after transfusion therapy with OR or OCR blood is between 70 and 110 mg/dL. In another aspect, glucose in a patient is between 70 and 100 mg/dL. In another aspect, glucose in a patient is between 90 and 120 mg/dL. In another aspect, glucose in a patient after transfusion therapy with OR or OCR blood is between 90 and 100 mg/dL.

Methods of the present disclosure provide for, and include, reducing glucose levels in a trauma patient in need of transfusion therapy to less than 120 mg/dL comprising providing a trauma patient with oxygen reduced stored blood that has an oxygen saturation of 20% or less prior to and during storage. In a further aspect, glucose in a patient after transfusion therapy with OR or OCR blood is less than 110 mmol/L. In yet another aspect, glucose in a patient after transfusion therapy with OR or OCR blood is less than 100 mg/dL. In another aspect, glucose in a patient after transfusion therapy with OR or OCR blood is less than 200 mg/dL. In another aspect, glucose in a patient after transfusion therapy with OR or OCR blood is less than 90 mg/dL. In another aspect, glucose in a patient after transfusion therapy with OR or OCR blood is less than 80 mg/dL.

In an aspect of the present disclosure, a patient is at increased risk of complications from transfusion therapies based on a pre-existing or underlying condition. In an aspect, a patient has a pre-existing or underlying condition selected from the group consisting of a diabetes, ischemic heart disease, systemic inflammatory syndrome brought on by trauma or infection, multiple organ failure brought on by trauma or infection, smoke inhalation, chronic pulmonary obstructive disease such as systemic inflammation due to infection, a coagulopathy disorder, and autoimmune diseases. In another aspect, a patient has one or more pre-existing or underlying conditions selected from the group consisting of a diabetes, ischemic heart disease, systemic inflammatory syndrome brought on by trauma or infection, multiple organ failure brought on by trauma or infection, smoke inhalation, and chronic pulmonary obstructive disease such as systemic inflammation due to infection, a coagulopathy disorder, and autoimmune diseases. In another aspect, a patient has two or more pre-existing or underlying conditions selected from the group consisting of a diabetes, ischemic heart disease, systemic inflammatory syndrome brought on by trauma or infection, multiple organ failure brought on by trauma or infection, smoke inhalation, chronic pulmonary obstructive disease such as systemic inflammation due to infection, a coagulopathy disorder, and autoimmune diseases. In another aspect, a patient has three or more pre-existing or underlying conditions selected from the group consisting of a diabetes, ischemic heart disease, systemic inflammatory syndrome brought on by trauma or infection, multiple organ failure brought on by trauma or infection, smoke inhalation, chronic pulmonary obstructive disease such as systemic inflammation due to infection, a coagulopathy disorder, and autoimmune diseases.

During hemorrhagic shock, patients experience an adverse event including liver damage or failure, kidney damage or failure, lung damage or failure, or a combination thereof. The present disclosure provides for, and includes, a patient in need of transfusion therapy with OR or OCR RBCs exhibits one or more adverse event selected from the group consisting of liver damage or failure, kidney damage or failure, or lung damage or failure. The present disclosure provides for, and includes, a patient in need thereof that exhibits two or more adverse events selected from the group consisting of liver damage or failure, kidney damage or failure, or lung damage or failure.

Methods of the present disclosure provide for, and include, reducing an adverse event in a trauma patient comprising providing a trauma patient in need of transfusion therapy with oxygen reduced stored blood that has an oxygen saturation of 20% or less prior to and during storage. In an aspect, the adverse event after transfusion therapy with OR or OCR blood is reduced by at least 5%. In another aspect, the adverse event after transfusion therapy with OR or OCR blood is reduced by at least 10%. In another aspect, the adverse event after transfusion therapy with OR or OCR blood is reduced by at least 20%. In another aspect, the adverse event after transfusion therapy with OR or OCR blood is reduced by at least 30%. In another aspect, the adverse event after transfusion therapy with OR or OCR blood is reduced by at least 40%. In another aspect, the adverse event after transfusion therapy with OR or OCR blood is reduced by at least 50%. In another aspect, the adverse event after transfusion therapy with OR or OCR blood is reduced by at least 60%. In another aspect, the adverse event is reduced by at least 70%. In another aspect, the adverse event after transfusion therapy with OR or OCR blood is reduced by at least 80%. In another aspect, the adverse event is reduced by at least 90%. In a further aspect, the adverse event after transfusion therapy with OR or OCR blood is reduced by between 1 and 10%, 10 and 20%, 20 and 30%, 30 and 40%, 40 and 50%, 50 and 60%, 60 and 70%, 70 and 80%, 80 and 90%, or 90 and 95%. In an aspect, the adverse event after transfusion therapy with OR or OCR blood is liver injury or damage. In another aspect, the adverse event is lung injury or damage. In yet another aspect, the adverse event is kidney injury or damage. In a further aspect, an adverse event is liver injury, lung injury, kidney injury, or a combination thereof.

Elevated levels of liver enzymes, including but not limited to aspartate aminotransferase (AST) and alanine aminotransferase (ALT), signify some form of liver damage, shock, or injury. Methods of the present disclosure provide for, and include, reducing elevated levels of liver enzymes in a trauma patient comprising providing a trauma patient with oxygen reduced stored blood that has an oxygen saturation of 20% or less prior to and during storage.

Methods of the present disclosure provide for, and include, reducing AST levels in a trauma patient in need of transfusion therapy comprising providing a trauma patient with oxygen reduced stored blood that has an oxygen saturation of 20% or less prior to and during storage. In an aspect, the AST level is reduced by at least 5% relative to the AST level of a patient transfused with conventionally stored blood. In another aspect, the AST level is reduced by at least 10% relative to the AST level of a patient transfused with conventionally stored blood. In another aspect, the AST level is reduced by at least 20% relative to the AST level of a patient transfused with conventionally stored blood. In another aspect, the AST level is reduced by at least 30% relative to the AST level of a patient transfused with conventionally stored blood. In another aspect, the AST level is reduced by at least 40%. In another aspect, the AST level is reduced by at least 50% relative to the AST level of a patient transfused with conventionally stored blood. In another aspect, the AST level is reduced by at least 60%. In another aspect, the AST level is reduced by at least 70% relative to the AST level of a patient transfused with conventionally stored blood. In yet another aspect, the AST level is reduced by at least 80%. In a further aspect, the AST level is reduced by at least 90% relative to the AST level of a patient transfused with conventionally stored blood. In a further aspect, the AST level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the AST level of a patient transfused with conventionally stored blood.

Methods of the present disclosure provide for, and include, reducing AST levels in a trauma patient in need of transfusion therapy by between 1.5 and 10 fold comprising providing a trauma patient with oxygen reduced stored blood that has an oxygen saturation of 20% or less prior to and during storage. In an aspect, the AST level is reduced by between 2 and 3 fold relative to the AST level of a patient transfused with conventionally stored blood. In another aspect, the AST level is reduced by between 3 and 4 fold. In another aspect, the AST level is reduced by between 4 and 10 fold. In another aspect, the AST level is reduced by between 6 and 9 fold relative to the AST level of a patient transfused with conventionally stored blood. In a further aspect, the AST level is reduced by between 2 and 5 fold. In another aspect, the AST level is reduced by between 10 and 50 fold relative to the AST level of a patient transfused with conventionally stored blood.

Methods of the present disclosure provide for, and include, reducing AST levels in a trauma patient in need of transfusion therapy by at least 1.5 fold comprising providing a trauma patient with oxygen reduced stored blood that has an oxygen saturation of 20% or less prior to and during storage. In an aspect, the AST level is reduced by at least 2 fold relative to the AST level of a patient transfused with conventionally stored blood. In another aspect, the AST level is reduced by at least 3 fold relative to the AST level of a patient transfused with conventionally stored blood. In another aspect, the AST level is reduced by at least 4 fold relative to the AST level of a patient transfused with conventionally stored blood. In another aspect, the AST level is reduced by at least 5 fold relative to the AST level of a patient transfused with conventionally stored blood. In a further aspect, the AST level is reduced by at least 6 fold. In another aspect, the AST level is reduced by at least 7 fold relative to the AST level of a patient transfused with conventionally stored blood. In another aspect, the AST level is reduced by at least 8 fold. In another aspect, the AST level is reduced by at least 9 fold relative to the AST level of a patient transfused with conventionally stored blood. In another aspect, the AST level is reduced by at least 10 fold relative to the AST level of a patient transfused with conventionally stored blood. In a further aspect, the AST level is reduced by at least 50 fold relative to the AST level of a patient transfused with conventionally stored blood.

Methods of the present disclosure provide for, and include, reducing ALT levels in a trauma patient in need of transfusion therapy comprising providing a trauma patient with oxygen reduced stored blood that has an oxygen saturation of 20% or less prior to and during storage. In an aspect, the ALT level is reduced by at least 5% relative to the ALT level of a patient transfused with conventionally stored blood. In another aspect, the ALT level is reduced by at least 10% relative to the ALT level of a patient transfused with conventionally stored blood. In another aspect, the ALT level is reduced by at least 20% relative to the ALT level of a patient transfused with conventionally stored blood. In another aspect, the ALT level is reduced by at least 30% relative to the ALT level of a patient transfused with conventionally stored blood. In another aspect, the ALT level is reduced by at least 40% relative to the AS ALT T level of a patient transfused with conventionally stored blood. In another aspect, the ALT level is reduced by at least 50% relative to the ALT level of a patient transfused with conventionally stored blood. In another aspect, the ALT level is reduced by at least 60% relative to the ALT level of a patient transfused with conventionally stored blood. In another aspect, the ALT level is reduced by at least 70% relative to the ALT level of a patient transfused with conventionally stored blood. In yet another aspect, the ALT level is reduced by at least 80% relative to the ALT level of a patient transfused with conventionally stored blood. In a further aspect, the ALT level is reduced by at least 90%. In a further aspect, the ALT level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the ALT level of a patient transfused with conventionally stored blood.

Methods of the present disclosure provide for, and include, reducing ALT levels in a trauma patient in need of transfusion therapy by between 1.5 and 10 fold comprising providing a trauma patient with oxygen reduced stored blood that has an oxygen saturation of 20% or less prior to and during storage. In an aspect, the ALT level is reduced by between 2 and 3 fold relative to the ALT level of a patient transfused with conventionally stored blood. In another aspect, the ALT level is reduced by between 3 and 4 fold relative to the ALT level of a patient transfused with conventionally stored blood. In another aspect, the ALT level is reduced by between 4 and 10 fold relative to the ALT level of a patient transfused with conventionally stored blood. In another aspect, the ALT level is reduced by between 6 and 9 fold relative to the ALT level of a patient transfused with conventionally stored blood. In a further aspect, the ALT level is reduced by between 2 and 5 fold. In another aspect, the ALT level is reduced by between 10 and 50 fold relative to the ALT level of a patient transfused with conventionally stored blood.

Methods of the present disclosure provide for, and include, reducing ALT levels in a trauma patient in need of transfusion therapy by at least 1.5 fold comprising providing a trauma patient with oxygen reduced stored blood that has an oxygen saturation of 20% or less prior to and during storage. In an aspect, the ALT level is reduced by at least 2 fold relative to the ALT level of a patient transfused with conventionally stored blood. In another aspect, the ALT level is reduced by at least 3 fold relative to the ALT level of a patient transfused with conventionally stored blood. In another aspect, the ALT level is reduced by at least 4 fold relative to the ALT level of a patient transfused with conventionally stored blood. In another aspect, the ALT level is reduced by at least 5 fold relative to the ALT level of a patient transfused with conventionally stored blood. In a further aspect, the ALT level is reduced by at least 6 fold relative to the ALT level of a patient transfused with conventionally stored blood. In another aspect, the ALT level is reduced by at least 7 fold relative to the ALT level of a patient transfused with conventionally stored blood. In another aspect, the ALT level is reduced by at least 8 fold relative to the ALT level of a patient transfused with conventionally stored blood. In another aspect, the ALT level is reduced by at least 9 fold relative to the ALT level of a patient transfused with conventionally stored blood. In another aspect, the ALT level is reduced by at least 10 fold relative to the ALT level of a patient transfused with conventionally stored blood. In a further aspect, the ALT level is reduced by at least 50 fold relative to the ALT level of a patient transfused with conventionally stored blood.

Markers of kidney function during and after hemorrhagic trauma include urine neutrophil gelatinase-associated lipocalin (u-NGAL), serum creatinine, and blood urea nitrogen (BUN). See Treeprasertsuk et al., "Urine neutrophil gelatinase-associated lipocalin: a diagnostic and prognostic marker for acute kidney injury (AKI) in hospitalized cirrhotic patients with AKI-prone conditions," *BMC Gastroenterol* 15:140 (2015) (hereby incorporated by reference in its entirety). Gene expression analyses reported in greater than 150 distinct studies performed in AM models from several species ranging from rodents to humans have consistently revealed the NGAL gene to be one of the most dramatically upregulated genes in the kidney soon after an ischemic or a nephrotoxic insult. See Ciccia et al., "Pediatric acute kidney injury: prevalence, impact and management challenges," *Int J Nephrol Renovasc Dis,* 10:77-84 (2017) (hereby incorporated by reference in its entirety). Similarly serum creatinine levels can vary depending on age, race and body size, however, rising creatinine levels are indicative of kidney damage. Creatinine levels of greater than 1.2 for women and greater than 1.4 for men may be an early sign of kidney damage. Increased blood urea nitrogen (BUN) is seen associated with kidney disease or failure, as well as, congestive heart failure, shock and bleeding in the digestive tract. If the BUN level is higher than 100 mg/dL it points to severe kidney damage. Decreased levels of BUN are also a concern and can point to fluid excess, trauma, surgery, opioids, malnutrition, and anabolic steroid use. See Pagana, "Mosby's Manual of Diagnostic and Laboratory Tests," St. Louis Mosby, Inc., (1998); and Gowda, et al., "Markers of renal function tests," *N Am J Med Sci.* 2(4): 170-173(2010) (hereby incorporated by reference in their entireties). Decreased u-NGAL (FIGS. 16A and 16B) serum creatinine (FIGS. 11A and 11B), and BUN (FIGS. 12A and 12B) levels in animals resuscitated with OR- and OCR-RBCs compared to conventionally RBCs, as provided by the present disclosure, show that resuscitation with OR-RBCs can significantly improve patients' clinical outcome.

Methods of the present disclosure provide for, and include, reducing urinary neutrophil gelatinase-associated lipocalin (u-NGAL) levels in a patient in need of transfusion therapy comprising providing a patient with oxygen reduced stored blood that has an oxygen saturation of 20% or less prior to and during storage. In an aspect, the u-NGAL level is reduced by at least 5% relative to the u-NGAL level of a patient transfused with conventionally stored blood. In another aspect, the u-NGAL level is reduced by at least 10% relative to the u-NGAL level of a patient transfused with conventionally stored blood. In another aspect, the u-NGAL level is reduced by at least 20% relative to the u-NGAL level of a patient transfused with conventionally stored blood. In another aspect, the u-NGAL level is reduced by at least 30%. In another aspect, the u-NGAL level is reduced by at least 40% relative to the u-NGAL level of a patient transfused with conventionally stored blood. In another aspect, the u-NGAL level is reduced by at least 50% relative to the u-NGAL level of a patient transfused with conventionally stored blood. In another aspect, the u-NGAL level is reduced by at least 60% relative to the u-NGAL level of a patient transfused with conventionally stored blood. In another aspect, the u-NGAL level is reduced by at least 70% relative to the u-NGAL level of a patient transfused with conventionally stored blood. In yet another aspect, the u-NGAL level is reduced by at least 80% relative to the u-NGAL level of a patient transfused with conventionally stored blood. In a further aspect, the u-NGAL level is reduced by at least 90% relative to the u-NGAL level of a patient transfused with conventionally stored blood. In a further aspect, the u-NGAL level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the u-NGAL level of a patient transfused with conventionally stored blood.

Methods of the present disclosure provide for, and include, reducing urinary neutrophil gelatinase-associated lipocalin (u-NGAL) levels in a patient in need of transfusion therapy comprising providing a patient by between 1.5 and 10 fold with oxygen reduced stored blood that has an oxygen saturation of 20% or less prior to and during storage. In an aspect, the u-NGAL level is reduced by between 2 and 3 fold relative to the u-NGAL level of a patient transfused with conventionally stored blood. In another aspect, the u-NGAL level is reduced by between 3 and 4 fold relative to the u-NGAL level of a patient transfused with conventionally stored blood. In another aspect, the u-NGAL level is reduced by between 4 and 10 fold. In another aspect, the u-NGAL level is reduced by between 6 and 9 fold relative to the u-NGAL level of a patient transfused with conventionally stored blood. In a further aspect, the u-NGAL level is reduced by between 2 and 5 fold relative to the u-NGAL level of a patient transfused with conventionally stored blood. In another aspect, the u-NGAL level is reduced by between 10 and 50 fold relative to the u-NGAL level of a patient transfused with conventionally stored blood.

Methods of the present disclosure provide for, and include, reducing urinary neutrophil gelatinase-associated lipocalin (u-NGAL) levels in a patient in need of transfusion therapy comprising providing a patient by at least 1.5 fold with oxygen reduced stored blood that has an oxygen saturation of 20% or less prior to and during storage. In an aspect, the u-NGAL level is reduced by at least 2 fold relative to the u-NGAL level of a patient transfused with conventionally stored blood. In another aspect, the u-NGAL level is reduced by at least 3 fold relative to the u-NGAL level of a patient transfused with conventionally stored blood. In another aspect, the u-NGAL level is reduced by at least 4 fold relative to the u-NGAL level of a patient transfused with conventionally stored blood. In another aspect, the u-NGAL level is reduced by at least 5 fold relative to the u-NGAL level of a patient transfused with conventionally stored blood. In a further aspect, the u-NGAL level is reduced by at least 6 fold relative to the u-NGAL level of a patient transfused with conventionally stored blood. In another aspect, the u-NGAL level is reduced by at least 7 fold relative to the u-NGAL level of a patient transfused with conventionally stored blood. In another aspect, the u-NGAL level is reduced by at least 8 fold relative to the u-NGAL level of a patient transfused with conventionally stored blood. In another aspect, the u-NGAL level is reduced by at least 9 fold. In another aspect, the u-NGAL level is reduced by at least 10 fold. In a further aspect, the u-NGAL level is reduced by at least 50 fold.

Methods of the present disclosure provide for, and include, reducing serum creatinine levels in a patient in need of transfusion therapy comprising providing a patient with oxygen reduced stored blood that has an oxygen saturation of 20% or less prior to and during storage. In an aspect, the serum creatinine level is reduced by at least 5% relative to the serum creatinine level of a patient transfused with conventionally stored blood. In another aspect, the serum creatinine level is reduced by at least 10% relative to the serum creatinine level of a patient transfused with conventionally stored blood. In another aspect, the serum creatinine level is reduced by at least 20% relative to the serum creatinine level of a patient transfused with conventionally stored blood. In another aspect, the serum creatinine level is reduced by at least 30% relative to the serum creatinine level of a patient transfused with conventionally stored blood. In another aspect, the serum creatinine level is reduced by at least 40% relative to the serum creatinine level of a patient transfused with conventionally stored blood. In another aspect, the serum creatinine level is reduced by at least 50% relative to the serum creatinine level of a patient transfused with conventionally stored blood. In another aspect, the serum creatinine level is reduced by at least 60% relative to the serum creatinine level of a patient transfused with conventionally stored blood. In another aspect, the serum creatinine level is reduced by at least 70% relative to the serum creatinine level of a patient transfused with conventionally stored blood. In yet another aspect, the serum creatinine level is reduced by at least 80% relative to the serum creatinine level of a patient transfused with conventionally stored blood. In a further aspect, the serum creatinine level is reduced by at least 90% relative to the serum creatinine level of a patient transfused with conventionally stored blood. In a further aspect, the serum creatinine level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the serum creatinine level of a patient transfused with conventionally stored blood.

Methods of the present disclosure provide for, and include, reducing serum creatinine levels in a patient in need of transfusion therapy by between 1.5 and 10 fold comprising providing a patient with oxygen reduced stored blood that has an oxygen saturation of 20% or less prior to and during storage. In an aspect, the serum creatinine level is reduced by between 2 and 3 fold relative to the serum creatinine level of a patient transfused with conventionally stored blood. In another aspect, the serum creatinine level is reduced by between 3 and 4 fold relative to the serum creatinine level of a patient transfused with conventionally stored blood. In another aspect, the serum creatinine level is reduced by between 4 and 10 fold relative to the serum creatinine level of a patient transfused with conventionally stored blood. In another aspect, the serum creatinine level is reduced by between 6 and 9 fold relative to the serum creatinine level of a patient transfused with conventionally stored blood. In a further aspect, the serum creatinine level is reduced by between 2 and 5 fold relative to the serum creatinine level of a patient transfused with conventionally stored blood. In another aspect, the serum creatinine level is reduced by between 10 and 50 fold relative to the serum creatinine level of a patient transfused with conventionally stored blood.

Methods of the present disclosure provide for, and include, reducing serum creatinine levels in a patient in need of transfusion therapy by at least 1.5 fold comprising providing a patient with oxygen reduced stored blood that has an oxygen saturation of 20% or less prior to and during storage. In an aspect, the serum creatinine level is reduced by at least 2 fold relative to the serum creatinine level of a patient transfused with conventionally stored blood. In another aspect, the serum creatinine level is reduced by at least 3 fold relative to the AST level of a patient transfused with conventionally stored blood. In another aspect, the serum creatinine level is reduced by at least 4 fold relative to the serum creatinine level of a patient transfused with conventionally stored blood. In another aspect, the serum creatinine level is reduced by at least 5 fold. In a further aspect, the serum creatinine level is reduced by at least 6 fold relative to the serum creatinine level of a patient transfused with conventionally stored blood. In another aspect, the serum creatinine level is reduced by at least 7 fold relative to the serum creatinine level of a patient transfused with conventionally stored blood. In another aspect, the serum creatinine level is reduced by at least 8 fold relative to the serum creatinine level of a patient transfused with conventionally stored blood. In another aspect, the serum creatinine level is reduced by at least 9 fold relative to the serum creatinine level of a patient transfused with conventionally stored blood. In another aspect, the serum creatinine level is reduced by at least 10 fold relative to the serum creatinine level of a patient transfused with conventionally stored blood.

Methods of the present disclosure provide for, and include, reducing serum creatinine levels in a patient in need of transfusion therapy to between 0.5 and 1.5 mg/dL comprising providing a patient with oxygen reduced stored blood that has an oxygen saturation of 20% or less prior to and during storage. In an aspect, the serum creatinine level is reduced to between 0.5 and 1 mg/dL relative to the serum creatinine level of a patient transfused with conventionally stored blood. In an aspect, the serum creatinine level is reduced to between 0.8 and 1 mg/dL relative to the serum creatinine level of a patient transfused with conventionally stored blood. In another aspect, the serum creatinine level is reduced to between 0.7 and 1.5 mg/dL relative to the serum creatinine level of a patient transfused with conventionally stored blood.

Methods of the present disclosure provide for, and include, reducing serum creatinine levels in a patient in need of transfusion therapy to less than 1.5 mg/dL comprising providing a patient with oxygen reduced stored blood that has an oxygen saturation of 20% or less prior to and during storage. In an aspect, the serum creatinine level is reduced to less than 1.4 mg/dL relative to the serum creatinine level of a patient transfused with conventionally stored blood. In an aspect, the serum creatinine level is reduced to less than 1 mg/dL. In another aspect, the serum creatinine level is reduced to less than 0.8 mg/dL relative to the serum creatinine level of a patient transfused with conventionally stored blood.

Methods of the present disclosure provide for, and include, reducing BUN levels in a patient comprising providing a patient in need of transfusion therapy with oxygen reduced stored blood that has an oxygen saturation of 20% or less prior to and during storage. In an aspect, the BUN level is reduced by at least 5% relative to the BUN level of a patient transfused with conventionally stored blood. In another aspect, the BUN level is reduced by at least 10% relative to the BUN level of a patient transfused with conventionally stored blood. In another aspect, the BUN level is reduced by at least 20% relative to the BUN level of a patient transfused with conventionally stored blood. In another aspect, the BUN level is reduced by at least 30% relative to the BUN level of a patient transfused with conventionally stored blood. In another aspect, the BUN level is reduced by at least 40% relative to the BUN level of a patient transfused with conventionally stored blood. In another aspect, the BUN level is reduced by at least 50% relative to the BUN level of a patient transfused with conventionally stored blood. In another aspect, the BUN level is reduced by at least 60% relative to the BUN level of a patient transfused with conventionally stored blood. In another aspect, the BUN level is reduced by at least 70% relative to the BUN level of a patient transfused with conventionally stored blood. In yet another aspect, the BUN level is reduced by at least 80% relative to the BUN level of a patient transfused with conventionally stored blood. In a further aspect, the BUN level is reduced by at least 90% relative to the BUN level of a patient transfused with conventionally stored blood. In a further aspect, the BUN level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the BUN level of a patient transfused with conventionally stored blood.

Methods of the present disclosure provide for, and include, reducing BUN levels in a patient by between 1.5 and 10 fold comprising providing a patient with oxygen reduced stored blood that has an oxygen saturation of 20% or less prior to and during storage. In an aspect, the BUN level is reduced by between 2 and 3 fold relative to the BUN level of a patient transfused with conventionally stored blood. In another aspect, the BUN level is reduced by between 3 and 4 fold. In another aspect, the BUN level is reduced by between 4 and 10 fold relative to the BUN level of a patient transfused with conventionally stored blood. In another aspect, the BUN level is reduced by between 6 and 9 fold relative to the BUN level of a patient transfused with conventionally stored blood. In a further aspect, the BUN level is reduced by between 2 and 5 fold relative to the BUN level of a patient transfused with conventionally stored blood. In another aspect, the BUN level is reduced by between 10 and 100 fold relative to the BUN level of a patient transfused with conventionally stored blood.

Methods of the present disclosure provide for, and include, reducing BUN levels in a patient by at least 1.5 fold comprising providing a patient in need of transfusion therapy with oxygen reduced stored blood that has an oxygen saturation of 20% or less prior to and during storage. In an aspect, the BUN level is reduced by at least 2 fold relative to the BUN level of a patient transfused with conventionally stored blood. In another aspect, the BUN level is reduced by at least 3 fold relative to the BUN level of a patient transfused with conventionally stored blood. In another aspect, the BUN level is reduced by at least 4 fold relative to the BUN level of a patient transfused with conventionally stored blood. In another aspect, the BUN level is reduced by at least 5 fold relative to the BUN level of a patient transfused with conventionally stored blood. In a further aspect, the BUN level is reduced by at least 6 fold. In another aspect, the BUN level is reduced by at least 7 fold relative to the BUN level of a patient transfused with conventionally stored blood. In another aspect, the BUN level is reduced by at least 8 fold relative to the BUN level of a patient transfused with conventionally stored blood. In another aspect, the BUN level is reduced by at least 9 fold relative to the BUN level of a patient transfused with conventionally stored blood. In another aspect, the BUN level is reduced by at least 10 fold relative to the BUN level of a patient transfused with conventionally stored blood.

Methods of the present disclosure provide for, and include, reducing the percentage of CD45+ neutrophils in a patient comprising providing a patient with oxygen reduced stored blood that has an oxygen saturation of 20% or less prior to and during storage. In an aspect, the percentage of CD45+ neutrophils is reduced by at least 5% relative to the CD45+ neutrophil level of a patient transfused with conventionally stored blood. In another aspect, the percentage of CD45+ neutrophils is reduced by at least 10% relative to the CD45+ neutrophil level of a patient transfused with conventionally stored blood. In another aspect, the percentage of CD45+ neutrophils is reduced by at least 20% relative to the CD45+ neutrophil level of a patient transfused with conventionally stored blood. In another aspect, the percentage of CD45+ neutrophils is reduced by at least 30% relative to the CD45+ neutrophil level of a patient transfused with conventionally stored blood. In another aspect, the percentage of CD45+ neutrophils is reduced by at least 40% relative to the CD45+ neutrophil level of a patient transfused with conventionally stored blood. In another aspect, the percentage of CD45+ neutrophils is reduced by at least 50% relative to the CD45+ neutrophil level of a patient transfused with conventionally stored blood. In another aspect, the percentage of CD45+ neutrophils is reduced by at least 60% relative to the CD45+ neutrophil level of a patient transfused with conventionally stored blood. In another aspect, the percentage of CD45+ neutrophils is reduced by at least 70% relative to the CD45+ neutrophil level of a patient transfused with conventionally stored blood. In yet another aspect, the percentage of CD45+ neutrophils is reduced by at least 80% relative to the CD45+ neutrophil level of a patient transfused with conventionally stored blood. In a further aspect, the percentage of CD45+ neutrophils is reduced by at least 90% relative to the CD45+ neutrophil level of a patient transfused with conventionally stored blood. In a further aspect, the percentage of CD45+ neutrophils is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the CD45+ neutrophil level of a patient transfused with conventionally stored blood.

Methods of the present disclosure provide for, and include, reducing the percentage of CD45+ neutrophils in a patient in need of transfusion therapy by between 1.5 and 10 fold comprising providing a patient with oxygen reduced stored blood that has an oxygen saturation of 20% or less prior to and during storage. In an aspect, the percentage of CD45+ neutrophils is reduced by between 2 and 3 fold relative to the CD45+ neutrophil level of a patient transfused with conventionally stored blood. In another aspect, the percentage of CD45+ neutrophils is reduced by between 3 and 4 fold relative to the CD45+ neutrophil level of a patient transfused with conventionally stored blood. In another aspect, the percentage of CD45+ neutrophils is reduced by between 4 and 10 fold relative to the CD45+ neutrophil level of a patient transfused with conventionally stored blood. In another aspect, the percentage of CD45+ neutrophils is reduced by between 6 and 9 fold relative to the CD45+ neutrophil level of a patient transfused with conventionally stored blood. In a further aspect, the percentage of CD45+ neutrophils is reduced by between 2 and 5 fold relative to the CD45+ neutrophil level of a patient transfused with conventionally stored blood. In another aspect, the percentage of CD45+ neutrophils is reduced by between 10 and 50 fold relative to the CD45+ neutrophil level of a patient transfused with conventionally stored blood.

Methods of the present disclosure provide for, and include, reducing the percentage of CD45+ neutrophils in a trauma patient in need of transfusion therapy by at least 1.5 fold comprising providing a trauma patient with oxygen reduced stored blood that has an oxygen saturation of 20% or less prior to and during storage. In an aspect, the percentage of CD45+ neutrophils is reduced by at least 2 fold relative to the CD45+ neutrophil level of a patient transfused with conventionally stored blood. In another aspect, the percentage of CD45+ neutrophils is reduced by at least 3 fold relative to the CD45+ neutrophil level of a patient transfused with conventionally stored blood. In another aspect, the percentage of CD45+ neutrophils is reduced by at least 4 fold relative to the CD45+ neutrophil level of a patient transfused with conventionally stored blood. In another aspect, the percentage of CD45+ neutrophils is reduced by at least 5 fold relative to the CD45+ neutrophil level of a patient transfused with conventionally stored blood. In a further aspect, the percentage of CD45+ neutrophils is reduced by at least 6 fold relative to the CD45+ neutrophil level of a patient transfused with conventionally stored blood. In another aspect, the percentage of CD45+ neutrophils is reduced by at least 7 fold relative to the CD45+ neutrophil level of a patient transfused with conventionally stored blood. In another aspect, the percentage of CD45+ neutrophils is reduced by at least 8 fold relative to the CD45+ neutrophil level of a patient transfused with conventionally stored blood. In another aspect, the percentage of CD45+ neutrophils is reduced by at least 9 fold relative to the CD45+ neutrophil level of a patient transfused with conventionally stored blood. In another aspect, the percentage of CD45+ neutrophils is reduced by at least 10 fold relative to the CD45+ neutrophil level of a patient transfused with conventionally stored blood.

Methods of the present disclosure provide for, and include, reducing the CXCL1 levels in a patient in need of transfusion therapy comprising providing a patient with oxygen reduced stored blood that has an oxygen saturation of 20% or less prior to and during storage. In an aspect, the CXCL1 level is reduced by at least 5% relative to the CXCL1 level of a patient transfused with conventionally stored blood. In another aspect, the CXCL1 level is reduced by at least 10% relative to the CXCL1 level of a patient transfused with conventionally stored blood. In another aspect, the CXCL1 level is reduced by at least 20% relative to the CXCL1 level of a patient transfused with conventionally stored blood. In another aspect, the CXCL1 level is reduced by at least 30% relative to the CXCL1 level of a patient transfused with conventionally stored blood. In another aspect, the CXCL1 level is reduced by at least 40% relative to the CXCL1 level of a patient transfused with conventionally stored blood. In another aspect, the CXCL1 level is reduced by at least 50% relative to the CXCL1 level of a patient transfused with conventionally stored blood. In another aspect, the CXCL1 level is reduced by at least 60% relative to the CXCL1 level of a patient transfused with conventionally stored blood. In another aspect, the CXCL1 level is reduced by at least 70% relative to the CXCL1 level of a patient transfused with conventionally stored blood. In yet another aspect, the CXCL1 level is reduced by at least 80% relative to the CXCL1 level of a patient transfused with conventionally stored blood. In a further aspect, the CXCL1 level is reduced by at least 90% relative to the CXCL1 level of a patient transfused with conventionally stored blood. In a further aspect, the CXCL1 level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the CXCL1 level of a patient transfused with conventionally stored blood Methods of the present disclosure provide for, and include, reducing the CXCL1 levels in a patient by between 1.5 and 10 fold comprising providing a patient with oxygen reduced stored blood that has an oxygen saturation of 20% or less prior to and during storage. In an aspect, the CXCL1 level is reduced by between 2 and 3 fold relative to the CXCL1 level of a patient transfused with conventionally stored blood. In another aspect, the CXCL1 level is reduced by between 3 and 4 fold relative to the CXCL1 level of a patient transfused with conventionally stored blood. In another aspect, the CXCL1 level is reduced by between 4 and 10 fold relative to the CXCL1 level of a patient transfused with conventionally stored blood. In another aspect, the CXCL1 level is reduced by between 6 and 9 fold relative to the CXCL1 level of a patient transfused with conventionally stored blood. In a further aspect, the CXCL1 level is reduced by between 2 and 5 fold relative to the CXCL1 level of a patient transfused with conventionally stored blood. In another aspect, the CXCL1 level is reduced by between 10 and 100 fold relative to the CXCL1 level of a patient transfused with conventionally stored blood.

Methods of the present disclosure provide for, and include, reducing the CXCL1 levels in a patient by at least 1.5 fold comprising providing a patient with oxygen reduced stored blood that has an oxygen saturation of 20% or less prior to and during storage. In an aspect, the CXCL1 level is reduced by at least 2 fold relative to the CXCL1 level of a patient transfused with conventionally stored blood. In another aspect, the CXCL1 level is reduced by at least 3 fold relative to the CXCL1 level of a patient transfused with conventionally stored blood. In another aspect, the CXCL1 level is reduced by at least 4 fold relative to the CXCL1 level of a patient transfused with conventionally stored blood. In another aspect, the CXCL1 level is reduced by at least 5 fold relative to the CXCL1 level of a patient transfused with conventionally stored blood. In a further aspect, the CXCL1 level is reduced by at least 6 fold relative to the CXCL1 level of a patient transfused with conventionally stored blood. In another aspect, the CXCL1 level is reduced by at least 7 fold relative to the CXCL1 level of a patient transfused with conventionally stored blood. In another aspect, the CXCL1 level is reduced by at least 8 fold relative to the CXCL1 level of a patient transfused with conventionally stored blood. In another aspect, the CXCL1 level is reduced by at least 9 fold relative to the CXCL1 level of a patient transfused with conventionally stored blood. In another aspect, the CXCL1 level is reduced by at least 10 fold relative to the CXCL1 level of a patient transfused with conventionally stored blood.

Although limited by the sensitivity of the test, healthy patients typically have an IL-6 level of less than $5\times10^{-12}$ gram/liter (pictogram/liter or pg/L). In the present disclosure, a patient in need thereof has an IL-6 level of at least 5 pg/L. In another aspect, a patient has an IL-6 level of at least 10 pg/L, 20 pg/L, 40 pg/L, 60 pg/L, 80 pg/L, 100 pg/L, or 150 pg/L. In yet another aspect, a patient in need thereof has a IL-6 level of between 10 and 50 pg/L, between 50 and 100 mg/L, between 100 and 200 mg/L, or between 10 and 200 mg/L. Methods of the present disclosure provide for, and include, reducing the IL-6 levels in a patient in need of transfusion therapy comprising providing a patient with oxygen reduced stored blood that has an oxygen saturation of 20% or less prior to and during storage. In an aspect, the IL-6 level is reduced by at least 5% relative to the IL-6 level of a patient transfused with conventionally stored blood. In another aspect, the IL-6 level is reduced by at least 10% relative to the IL-6 level of a patient transfused with conventionally stored blood. In another aspect, the IL-6 level is reduced by at least 20%. In another aspect, the IL-6 level is reduced by at least 30% relative to the IL-6 level of a patient transfused with conventionally stored blood. In another aspect, the IL-6 level is reduced by at least 40% relative to the IL-6 level of a patient transfused with conventionally stored blood. In another aspect, the IL-6 level is reduced by at least 50% relative to the IL-6 level of a patient transfused with conventionally stored blood. In another aspect, the IL-6 level is reduced by at least 60% relative to the IL-6 level of a patient transfused with conventionally stored blood. In another aspect, the IL-6 level is reduced by at least 70% relative to the IL-6 level of a patient transfused with conventionally stored blood. In yet another aspect, the IL-6 level is reduced by at least 80% relative to the IL-6 level of a patient transfused with conventionally stored blood. In a further aspect, the IL-6 level is reduced by at least 90% relative to the IL-6 level of a patient transfused with conventionally stored blood. In a further aspect, the IL-6 level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the IL-6 level of a patient transfused with conventionally stored blood.

Methods of the present disclosure provide for, and include, reducing the IL-6 levels in a patient by between 1.5 and 10 fold comprising providing a patient with oxygen reduced stored blood that has an oxygen saturation of 20% or less prior to and during storage. In an aspect, the IL-6 level is reduced by between 2 and 3 fold relative to the IL-6 level of a patient transfused with conventionally stored blood. In another aspect, the IL-6 level is reduced by between 3 and 4 fold relative to the IL-6 level of a patient transfused with conventionally stored blood. In another aspect, the IL-6 level is reduced by between 4 and 10 fold. In another aspect, the IL-6 level is reduced by between 6 and 9 fold relative to the IL-6 level of a patient transfused with conventionally stored blood. In a further aspect, the IL-6 level is reduced by between 2 and 5 fold relative to the IL-6 level of a patient transfused with conventionally stored blood. In another aspect, the IL-6 level is reduced by between 10 and 100 fold relative to the IL-6 level of a patient transfused with conventionally stored blood.

Methods of the present disclosure provide for, and include, reducing the IL-6 levels in a patient by at least 1.5 fold comprising providing a patient in need of transfusion therapy with oxygen reduced stored blood that has an oxygen saturation of 20% or less prior to and during storage. In an aspect, the IL-6 level is reduced by at least 2 fold relative to the IL-6 level of a patient transfused with conventionally stored blood. In another aspect, the IL-6 level is reduced by at least 3 fold relative to the IL-6 level of a patient transfused with conventionally stored blood. In another aspect, the IL-6 level is reduced by at least 4 fold relative to the IL-6 level of a patient transfused with conventionally stored blood. In another aspect, the IL-6 level is reduced by at least 5 fold. In a further aspect, the IL-6 level is reduced by at least 6 fold relative to the IL-6 level of a patient transfused with conventionally stored blood. In another aspect, the IL-6 level is reduced by at least 7 fold relative to the IL-6 level of a patient transfused with conventionally stored blood. In another aspect, the IL-6 level is reduced by at least 8 fold relative to the IL-6 level of a patient transfused with conventionally stored blood. In another aspect, the IL-6 level is reduced by at least 9 fold relative to the IL-6 level of a patient transfused with conventionally stored blood. In another aspect, the IL-6 level is reduced by at least 10 fold relative to the IL-6 level of a patient transfused with conventionally stored blood.

In an aspect of the present disclosure, a patient in need thereof is a patient with sepsis.

In an aspect of the present disclosure, a patient in need thereof is a patient with inflammation. In another aspect, a patient has systemic inflammation. In another aspect, a patient has chronic inflammation. In another aspect, a patient has acute inflammation.

In an aspect of the present disclosure, a patient with inflammation is a patient with sickle cell disease. In a further aspect, a patient with sickle cell disease has sickle cell anemia. In another aspect, a patient with sickle disease has sickle cell crisis. In yet another aspect, a patient has a type of sickle cell disease selected from the group consisting of hemoglobin SS, hemoglobin SC, hemoglobin SB+ beta thalassemia, hemoglobin SB (beta-zero) thalassemia, hemoglobin SD, hemoglobin SE, and hemoglobin SO.

The present disclosure provides for methods of preventing or reducing the number of vaso-occlusive episodes in a sickle cell patient in need thereof comprising providing previously stored oxygen reduced blood to a patient having sickle cell disease, wherein the oxygen reduced blood has an oxygen saturation of 20% or less during storage. In an aspect, the vaso-occlusive episodes are decreased by at least 10%, compared to a sickle cell patient receiving conventionally stored blood. In another aspect the number vaso-occlusive episodes are decreased by at least 10% over a period of at least 2, 3, 4, 5, 6, 7, 8, 9, 10, 20, 30, 40, or 50 weeks.

The present disclosure provides for decreasing adhesion of red blood cells to endothelial cells expressing thrombospondin in a sickle cell patient in need thereof. The present disclosure also provides for decreasing adhesion of red blood cells to endothelial cells expressing Vascular Cell Adhesion Molecule-1 (VCAM-1) in a patient in need thereof. Further, the present disclosure provides for decreasing adhesion of red blood cells to endothelial cells expressing laminin in a patient in need thereof. In an aspect, the adhesion is decreased by at least 10, 20, 30, 40, 50, 60, 70, 80, or 90%, compared to the adhesion of conventionally stored blood. In another aspect, the adhesion is decreased by between 10 and 20, 20 and 30, 30 and 40, 40 and 50, 50 and 60, 60 and 70, 70 and 80, or 80 and 90%, compared to the adhesion of conventionally stored blood.

The present disclosure provides for methods of improving transfusion in a sickle cell patient in need thereof comprising providing previously stored oxygen reduced blood to a patient having sickle cell disease, wherein the oxygen reduced blood has an oxygen saturation of 20% or less during storage. In an aspect, the patient has dactylitis (hand-foot syndrome). In another aspect, the methods of the present disclosure provides for reducing the occurrences of dactylitis. In another aspect, the occurrence of dactylitis is decreased by at least 10, 20, 30, 40, 50, 60, 70, or 80% compared to a patient receiving transfusions of conventionally stored RBCs. In another aspect, the present disclosure provides for reducing the number of pain crises in a patient compared to a patient treated with conventionally stored RBCs. In yet another aspect, the present disclosure provides for reducing complications of anemia selected from the group consisting of fatigue, irritability, dizziness, difficulty breathing, pale skin color, jaundice, slow growth, and delayed puberty. In another aspect, the present disclosure provides for reducing infection. In yet another aspect, the present disclosure provides for preventing infection. In a further aspect, the present disclosure provides for reducing spleen damage. In one aspect, spleen damage is splenic sequestration. In another aspect, spleen damage is splenic enlargement. In a further aspect, the present disclosure provides for reducing or preventing stroke.

In an aspect of the present disclosure, a patient in need thereof is a patient with a fever. In another aspect, a patient in need thereof has a fever of at least 38° C. In another aspect, a patient in need thereof has a fever of about 39, 40, 41, or 42° C. In another aspect, a patient has a fever of between 38 and 42° C. In another aspect, a patient in need thereof has a fever and increased c-reactive protein (CRP) levels compared to a patient without a fever. In another aspect, a patient with a fever has increased levels of one or more inflammatory mediators selected from the group consisting of IL-6, IL-8, IL-10, and granulocyte-colony stimulating factor (G-CSF), compared to a patient without fever. In another aspect, a patient with a fever has decreased levels of one or more inflammatory mediators selected from the group consisting of CCL-5 and CXCL-10, compared to a patient without fever.

In an aspect of the present disclosure, a patient in need thereof is a patient at risk of fever. In another aspect, a patient has a fever of between 38 and 42° C. In another aspect, a patient in need thereof at risk of fever has an increased c-reactive protein (CRP) level compared to a healthy persons. In another aspect, a patient in need thereof increased levels of one or more inflammatory mediators selected from the group consisting of IL-6, IL-8, IL-10, and granulocyte-colony stimulating factor (G-CSF), compared to a healthy person. In another aspect, a patient in need thereof has decreased levels of one or more inflammatory mediators selected from the group consisting of CCL-5 and CXCL-10, compared to a healthy patient.

Although limited by the sensitivity of the test, healthy patients typically have a CRP level of less than 3 mg/L. In an aspect, a patient in need thereof has a CRP level of at least 3 mg/L. In another aspect, a patient has a CRP level of at least 4 mg/L, 5 mg/L, 6 mg/L, 7 mg/L, 8 mg/L, 9 mg/L, or 10 mg/L. In yet another aspect, a patient in need thereof has a CRP level of between 3 and 5 mg/L, between 3 and 10 mg/L, between 5 and 10 mg/L, or between 3 and 8 mg/L.

Methods of the present disclosure provide for, and include, decreasing the CRP levels in a patient in need of transfusion therapy comprising providing a patient with oxygen decreased stored blood that has an oxygen saturation of 20% or less prior to and during storage. In an aspect, the CRP level is restored to a the normal level of a healthy person. In an aspect, the CRP level is decreased by at least 5% relative to the CRP level of a patient transfused with conventionally stored blood. In another aspect, the CRP level is decreased by at least 10% relative to the CRP level of a patient transfused with conventionally stored blood. In another aspect, the CRP level is decreased by at least 20%. In another aspect, the CRP level is decreased by at least 30% relative to the CRP level of a patient transfused with conventionally stored blood. In another aspect, the CRP level is decreased by at least 40% relative to the CRP level of a patient transfused with conventionally stored blood. In another aspect, the CRP level is decreased by at least 50% relative to the CRP level of a patient transfused with conventionally stored blood. In another aspect, the CRP level is decreased by at least 60% relative to the CRP level of a patient transfused with conventionally stored blood. In another aspect, the CRP level is decreased by at least 70% relative to the CRP level of a patient transfused with conventionally stored blood. In yet another aspect, the CRP level is decreased by at least 80% relative to the CRP level of a patient transfused with conventionally stored blood. In a further aspect, the CRP level is decreased by at least 90% relative to the CRP level of a patient transfused with conventionally stored blood. In a further aspect, the CRP level is decreased by between 1 and 10%, 10 and 20%, 20 and 30%, 30 and 40%, 40 and 50%, 50 and 60%, 60 and 70%, 70 and 80%, 80 and 90%, or 90 and 95% relative to the CRP level of a patient transfused with conventionally stored blood.

Methods of the present disclosure provide for, and include, decreasing the CRP levels in a patient in need thereof by between 1.5 and 10 fold comprising providing a patient with oxygen decreased stored blood that has an oxygen saturation of 20% or less prior to and during storage. In an aspect, the CRP level is reduced by between 2 and 3 fold relative to the CRP level of a patient transfused with conventionally stored blood. In another aspect, the CRP level is decreased by between 3 and 4 fold relative to the CRP level of a patient transfused with conventionally stored blood. In another aspect, the CRP level is decreased by between 4 and 10 fold. In another aspect, the CRP level is decreased by between 6 and 9 fold relative to the CRP level of a patient transfused with conventionally stored blood. In a further aspect, the CRP level is decreased by between 2 and 5 fold relative to the CRP level of a patient transfused with conventionally stored blood. In another aspect, the CRP level is decreased by between 10 and 100 fold relative to the CRP level of a patient transfused with conventionally stored blood.

Methods of the present disclosure provide for, and include, decreasing the CRP levels in a patient in need thereof by at least 1.5 fold comprising providing a patient in need of transfusion therapy with oxygen decreased stored blood that has an oxygen saturation of 20% or less prior to and during storage. In an aspect, the CRP level is decreased by at least 2 fold relative to the CRP level of a patient transfused with conventionally stored blood. In another aspect, the CRP level is decreased by at least 3 fold relative to the CRP level of a patient transfused with conventionally stored blood. In another aspect, the CRP level is decreased by at least 4 fold relative to the CRP level of a patient transfused with conventionally stored blood. In another aspect, the CRP level is decreased by at least 5 fold. In a further aspect, the CRP level is decreased by at least 6 fold relative to the CRP level of a patient transfused with conventionally stored blood. In another aspect, the CRP level is decreased by at least 7 fold relative to the CRP level of a patient transfused with conventionally stored blood. In another aspect, the CRP level is decreased by at least 8 fold relative to the CRP level of a patient transfused with conventionally stored blood. In another aspect, the CRP level is decreased by at least 9 fold relative to the CRP level of a patient transfused with conventionally stored blood. In another aspect, the CRP level is decreased by at least 10 fold relative to the CRP level of a patient transfused with conventionally stored blood.

Although limited by the sensitivity of the test, healthy patients typically have an IL-8 level of less than 40 picograms/liter (pg/L). In an aspect, a patient in need thereof has an IL-8 level of at least 40 pg/L. In another aspect, a patient has an IL-8 level of at least 50 pg/L, 5 pg/L, 6 pg/L, 7 pg/L, 8 pg/L, 9 pg/L, or 10 pg/L. In yet another aspect, a patient in need thereof has a CRP level of between 30 and 50 pg/L, between 40 and 100 pg/L, between 50 and 100 pg/L, or between 60 and 200 pg/L.

Methods of the present disclosure provide for, and include, reducing the IL-8 levels in a patient in need of transfusion therapy comprising providing a patient with oxygen reduced stored blood that has an oxygen saturation of 20% or less prior to and during storage. In an aspect, the IL-8 level is restored to a the normal level of a healthy person. In an aspect, the IL-8 level is reduced by at least 5% relative to the IL-8 level of a patient transfused with conventionally stored blood. In another aspect, the IL-8 level is reduced by at least 10% relative to the IL-8 level of a patient transfused with conventionally stored blood. In another aspect, the IL-8 level is reduced by at least 20%. In another aspect, the IL-8 level is reduced by at least 30% relative to the IL-8 level of a patient transfused with conventionally stored blood. In another aspect, the IL-8 level is reduced by at least 40% relative to the IL-8 level of a patient transfused with conventionally stored blood. In another aspect, the IL-8 level is reduced by at least 50% relative to the IL-8 level of a patient transfused with conventionally stored blood. In another aspect, the IL-8 level is reduced by at least 60% relative to the IL-8 level of a patient transfused with conventionally stored blood. In another aspect, the IL-8 level is reduced by at least 70% relative to the IL-8 level of a patient transfused with conventionally stored blood. In yet another aspect, the IL-8 level is reduced by at least 80% relative to the IL-8 level of a patient transfused with conventionally stored blood. In a further aspect, the IL-8 level is reduced by at least 90% relative to the IL-8 level of a patient transfused with conventionally stored blood. In a further aspect, the IL-8 level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the IL-8 level of a patient transfused with conventionally stored blood.

Methods of the present disclosure provide for, and include, reducing the IL-8 levels in a patient in need thereof by between 1.5 and 10 fold comprising providing a patient with oxygen reduced stored blood that has an oxygen saturation of 20% or less prior to and during storage. In an aspect, the IL-8 level is reduced by between 2 and 3 fold relative to the IL-8 level of a patient transfused with conventionally stored blood. In another aspect, the IL-8 level is reduced by between 3 and 4 fold relative to the IL-8 level of a patient transfused with conventionally stored blood. In another aspect, the IL-8 level is reduced by between 4 and 10 fold. In another aspect, the IL-8 level is reduced by between 6 and 9 fold relative to the IL-8 level of a patient transfused with conventionally stored blood. In a further aspect, the IL-8 level is reduced by between 2 and 5 fold relative to the IL-8 level of a patient transfused with conventionally stored blood. In another aspect, the IL-8 level is reduced by between 10 and 100 fold relative to the IL-8 level of a patient transfused with conventionally stored blood.

Methods of the present disclosure provide for, and include, reducing the IL-8 levels in a patient in need thereof by at least 1.5 fold comprising providing a patient in need of transfusion therapy with oxygen reduced stored blood that has an oxygen saturation of 20% or less prior to and during storage. In an aspect, the IL-8 level is reduced by at least 2 fold relative to the IL-8 level of a patient transfused with conventionally stored blood. In another aspect, the IL-8 level is reduced by at least 3 fold relative to the IL-8 level of a patient transfused with conventionally stored blood. In another aspect, the IL-8 level is reduced by at least 4 fold relative to the IL-8 level of a patient transfused with conventionally stored blood. In another aspect, the IL-8 level is reduced by at least 5 fold. In a further aspect, the IL-8 level is reduced by at least 6 fold relative to the IL-8 level of a patient transfused with conventionally stored blood. In another aspect, the IL-8 level is reduced by at least 7 fold relative to the IL-8 level of a patient transfused with conventionally stored blood. In another aspect, the IL-8 level is reduced by at least 8 fold relative to the IL-8 level of a patient transfused with conventionally stored blood. In another aspect, the IL-8 level is reduced by at least 9 fold relative to the IL-8 level of a patient transfused with conventionally stored blood. In another aspect, the IL-8 level is reduced by at least 10 fold relative to the IL-8 level of a patient transfused with conventionally stored blood.

A healthy person has an IL-10 level of less than about 20 pg/L. See Kleiner, G., et al., "Cytokine Levels in the Serum of Healthy Subjects" *Mediators of Inflammation,* 1-6 (2013). In the present disclosure, a patient in need thereof has an IL-10 level of at least 15 pg/L. In another aspect, a patient has an IL-10 level of at least 20 pg/L, 40 pg/L, 50 pg/L, 60 pg/L, 80 pg/L, 100 pg/L, or 150 pg/L. In yet another aspect, a patient in need thereof has a IL-10 level of between 20 and 50 pg/L, between 50 and 100 mg/L, between 100 and 200 mg/L, or between 15 and 200 mg/L.

Methods of the present disclosure provide for, and include, reducing the IL-10 levels in a patient in need of transfusion therapy comprising providing a patient with oxygen reduced stored blood that has an oxygen saturation of 20% or less prior to and during storage. In an aspect, the IL-10 level is restored to a the normal level of a healthy person. In an aspect, the IL-10 level is reduced by at least 5% relative to the IL-10 level of a patient transfused with conventionally stored blood. In another aspect, the IL-10 level is reduced by at least 10% relative to the IL-10 level of a patient transfused with conventionally stored blood. In another aspect, the IL-10 level is reduced by at least 20%. In another aspect, the IL-10 level is reduced by at least 30% relative to the IL-10 level of a patient transfused with conventionally stored blood. In another aspect, the IL-10 level is reduced by at least 40% relative to the IL-10 level of a patient transfused with conventionally stored blood. In another aspect, the IL-10 level is reduced by at least 50% relative to the IL-10 level of a patient transfused with conventionally stored blood. In another aspect, the IL-10 level is reduced by at least 60% relative to the IL-10 level of a patient transfused with conventionally stored blood. In another aspect, the IL-10 level is reduced by at least 70% relative to the IL-10 level of a patient transfused with conventionally stored blood. In yet another aspect, the IL-10 level is reduced by at least 80% relative to the IL-10 level of a patient transfused with conventionally stored blood. In a further aspect, the IL-10 level is reduced by at least 90% relative to the IL-10 level of a patient transfused with conventionally stored blood. In a further aspect, the IL-10 level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the IL-10 level of a patient transfused with conventionally stored blood.

Methods of the present disclosure provide for, and include, reducing the IL-10 levels in a patient in need thereof by between 1.5 and 10 fold comprising providing a patient with oxygen reduced stored blood that has an oxygen saturation of 20% or less prior to and during storage. In an aspect, the IL-10 level is reduced by between 2 and 3 fold relative to the IL-10 level of a patient transfused with conventionally stored blood. In another aspect, the IL-10 level is reduced by between 3 and 4 fold relative to the IL-10 level of a patient transfused with conventionally stored blood. In another aspect, the IL-10 level is reduced by between 4 and 10 fold. In another aspect, the IL-10 level is reduced by between 6 and 9 fold relative to the IL-10 level of a patient transfused with conventionally stored blood. In a further aspect, the IL-10 level is reduced by between 2 and 5 fold relative to the IL-10 level of a patient transfused with conventionally stored blood. In another aspect, the IL-10 level is reduced by between 10 and 100 fold relative to the IL-10 level of a patient transfused with conventionally stored blood.

Methods of the present disclosure provide for, and include, reducing the IL-10 levels in a patient in need thereof by at least 1.5 fold comprising providing a patient in need of transfusion therapy with oxygen reduced stored blood that has an oxygen saturation of 20% or less prior to and during storage. In an aspect, the IL-10 level is reduced by at least 2 fold relative to the IL-10 level of a patient transfused with conventionally stored blood. In another aspect, the IL-10 level is reduced by at least 3 fold relative to the IL-10 level of a patient transfused with conventionally stored blood. In another aspect, the IL-10 level is reduced by at least 4 fold relative to the IL-10 level of a patient transfused with conventionally stored blood. In another aspect, the IL-10 level is reduced by at least 5 fold. In a further aspect, the IL-10 level is reduced by at least 6 fold relative to the IL-10 level of a patient transfused with conventionally stored blood. In another aspect, the IL-10 level is reduced by at least 7 fold relative to the IL-10 level of a patient transfused with conventionally stored blood. In another aspect, the IL-10 level is reduced by at least 8 fold relative to the IL-10 level of a patient transfused with conventionally stored blood. In another aspect, the IL-10 level is reduced by at least 9 fold relative to the IL-10 level of a patient transfused with conventionally stored blood. In another aspect, the IL-10 level is reduced by at least 10 fold relative to the IL-10 level of a patient transfused with conventionally stored blood.

Methods of the present disclosure provide for, and include, reducing the G-CSF levels in a patient in need of transfusion therapy comprising providing a patient with oxygen reduced stored blood that has an oxygen saturation of 20% or less prior to and during storage. In an aspect, the G-CSF level is restored to a the normal level of a healthy person. In an aspect, the G-CSF level is reduced by at least 5% relative to the G-CSF level of a patient transfused with conventionally stored blood. In another aspect, the G-CSF level is reduced by at least 10% relative to the G-CSF level of a patient transfused with conventionally stored blood. In another aspect, the G-CSF level is reduced by at least 20%. In another aspect, the G-CSF level is reduced by at least 30% relative to the G-CSF level of a patient transfused with conventionally stored blood. In another aspect, the G-CSF level is reduced by at least 40% relative to the G-CSF level of a patient transfused with conventionally stored blood. In another aspect, the G-CSF level is reduced by at least 50% relative to the G-CSF level of a patient transfused with conventionally stored blood. In another aspect, the G-CSF level is reduced by at least 60% relative to the G-CSF level of a patient transfused with conventionally stored blood. In another aspect, the G-CSF level is reduced by at least 70% relative to the G-CSF level of a patient transfused with conventionally stored blood. In yet another aspect, the G-CSF level is reduced by at least 80% relative to the G-CSF level of a patient transfused with conventionally stored blood. In a further aspect, the G-CSF level is reduced by at least 90% relative to the G-CSF level of a patient transfused with conventionally stored blood. In a further aspect, the G-CSF level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the G-CSF level of a patient transfused with conventionally stored blood.

Methods of the present disclosure provide for, and include, reducing the G-CSF levels in a patient by between 1.5 and 10 fold comprising providing a patient with oxygen reduced stored blood that has an oxygen saturation of 20% or less prior to and during storage. In an aspect, the G-CSF level is reduced by between 2 and 3 fold relative to the G-CSF level of a patient transfused with conventionally stored blood. In another aspect, the G-CSF level is reduced by between 3 and 4 fold relative to the G-CSF level of a patient transfused with conventionally stored blood. In another aspect, the G-CSF level is reduced by between 4 and 10 fold. In another aspect, the G-CSF level is reduced by between 6 and 9 fold relative to the G-CSF level of a patient transfused with conventionally stored blood. In a further aspect, the G-CSF level is reduced by between 2 and 5 fold relative to the G-CSF level of a patient transfused with conventionally stored blood. In another aspect, the G-CSF level is reduced by between 10 and 100 fold relative to the G-CSF level of a patient transfused with conventionally stored blood.

Methods of the present disclosure provide for, and include, reducing the G-CSF levels in a patient in need thereof by at least 1.5 fold comprising providing a patient in need of transfusion therapy with oxygen reduced stored blood that has an oxygen saturation of 20% or less prior to and during storage. In an aspect, the G-CSF level is reduced by at least 2 fold relative to the G-CSF level of a patient transfused with conventionally stored blood. In another aspect, the G-CSF level is reduced by at least 3 fold relative to the G-CSF level of a patient transfused with conventionally stored blood. In another aspect, the G-CSF level is reduced by at least 4 fold relative to the G-CSF level of a patient transfused with conventionally stored blood. In another aspect, the G-CSF level is reduced by at least 5 fold. In a further aspect, the G-CSF level is reduced by at least 6 fold relative to the G-CSF level of a patient transfused with conventionally stored blood. In another aspect, the G-CSF level is reduced by at least 7 fold relative to the G-CSF level of a patient transfused with conventionally stored blood. In another aspect, the G-CSF level is reduced by at least 8 fold relative to the G-CSF level of a patient transfused with conventionally stored blood. In another aspect, the G-CSF level is reduced by at least 9 fold relative to the G-CSF level of a patient transfused with conventionally stored blood. In another aspect, the G-CSF level is reduced by at least 10 fold relative to the G-CSF level of a patient transfused with conventionally stored blood.

Methods of the present disclosure provide for, and include, increasing the CCL-5 levels in a patient in need of transfusion therapy comprising providing a patient with oxygen increased stored blood that has an oxygen saturation of 20% or less prior to and during storage. In an aspect, the CCL-5 level is restored to a the normal level of a healthy person. In an aspect, the CCL-5 level is increased by at least 5% relative to the CCL-5 level of a patient transfused with conventionally stored blood. In another aspect, the CCL-5 level is increased by at least 10% relative to the CCL-5 level of a patient transfused with conventionally stored blood. In another aspect, the CCL-5 level is increased by at least 20%.

In another aspect, the CCL-5 level is increased by at least 30% relative to the CCL-5 level of a patient transfused with conventionally stored blood. In another aspect, the CCL-5 level is increased by at least 40% relative to the CCL-5 level of a patient transfused with conventionally stored blood. In another aspect, the CCL-5 level is increased by at least 50% relative to the CCL-5 level of a patient transfused with conventionally stored blood. In another aspect, the CCL-5 level is increased by at least 60% relative to the CCL-5 level of a patient transfused with conventionally stored blood. In another aspect, the CCL-5 level is increased by at least 70% relative to the CCL-5 level of a patient transfused with conventionally stored blood. In yet another aspect, the CCL-5 level is increased by at least 80% relative to the CCL-5 level of a patient transfused with conventionally stored blood. In a further aspect, the CCL-5 level is increased by at least 90% relative to the CCL-5 level of a patient transfused with conventionally stored blood. In a further aspect, the CCL-5 level is increased by between 1 and 10%, 10 and 20%, 20 and 30%, 30 and 40%, 40 and 50%, 50 and 60%, 60 and 70%, 70 and 80%, 80 and 90%, or 90 and 95% relative to the CCL-5 level of a patient transfused with conventionally stored blood.

Methods of the present disclosure provide for, and include, increasing the CCL-5 levels in a patient in need thereof by between 1.5 and 10 fold comprising providing a patient with oxygen increased stored blood that has an oxygen saturation of 20% or less prior to and during storage. In an aspect, the CCL-5 level is reduced by between 2 and 3 fold relative to the CCL-5 level of a patient transfused with conventionally stored blood. In another aspect, the CCL-5 level is increased by between 3 and 4 fold relative to the CCL-5 level of a patient transfused with conventionally stored blood. In another aspect, the CCL-5 level is increased by between 4 and 10 fold. In another aspect, the CCL-5 level is increased by between 6 and 9 fold relative to the CCL-5 level of a patient transfused with conventionally stored blood. In a further aspect, the CCL-5 level is increased by between 2 and 5 fold relative to the CCL-5 level of a patient transfused with conventionally stored blood. In another aspect, the CCL-5 level is increased by between 10 and 100 fold relative to the CCL-5 level of a patient transfused with conventionally stored blood.

Methods of the present disclosure provide for, and include, increasing the CCL-5 levels in a patient in need thereof by at least 1.5 fold comprising providing a patient in need of transfusion therapy with oxygen increased stored blood that has an oxygen saturation of 20% or less prior to and during storage. In an aspect, the CCL-5 level is increased by at least 2 fold relative to the CCL-5 level of a patient transfused with conventionally stored blood. In another aspect, the CCL-5 level is increased by at least 3 fold relative to the CCL-5 level of a patient transfused with conventionally stored blood. In another aspect, the CCL-5 level is increased by at least 4 fold relative to the CCL-5 level of a patient transfused with conventionally stored blood. In another aspect, the CCL-5 level is increased by at least 5 fold. In a further aspect, the CCL-5 level is increased by at least 6 fold relative to the CCL-5 level of a patient transfused with conventionally stored blood. In another aspect, the CCL-5 level is increased by at least 7 fold relative to the CCL-5 level of a patient transfused with conventionally stored blood. In another aspect, the CCL-5 level is increased by at least 8 fold relative to the CCL-5 level of a patient transfused with conventionally stored blood. In another aspect, the CCL-5 level is increased by at least 9 fold relative to the CCL-5 level of a patient transfused with conventionally stored blood. In another aspect, the CCL-5 level is increased by at least 10 fold relative to the CCL-5 level of a patient transfused with conventionally stored blood.

Methods of the present disclosure provide for, and include, increasing the CXCL-10 levels in a patient in need of transfusion therapy comprising providing a patient with oxygen increased stored blood that has an oxygen saturation of 20% or less prior to and during storage. In an aspect, the CXCL-10 level is restored to a the normal level of a healthy person. In an aspect, the CXCL-10 level is increased by at least 5% relative to the CXCL-10 level of a patient transfused with conventionally stored blood. In another aspect, the CXCL-10 level is increased by at least 10% relative to the CXCL-10 level of a patient transfused with conventionally stored blood. In another aspect, the CXCL-10 level is increased by at least 20%. In another aspect, the CXCL-10 level is increased by at least 30% relative to the CXCL-10 level of a patient transfused with conventionally stored blood. In another aspect, the CXCL-10 level is increased by at least 40% relative to the CXCL-10 level of a patient transfused with conventionally stored blood. In another aspect, the CXCL-10 level is increased by at least 50% relative to the CXCL-10 level of a patient transfused with conventionally stored blood. In another aspect, the CXCL-10 level is increased by at least 60% relative to the CXCL-10 level of a patient transfused with conventionally stored blood. In another aspect, the CXCL-10 level is increased by at least 70% relative to the CXCL-10 level of a patient transfused with conventionally stored blood. In yet another aspect, the CXCL-10 level is increased by at least 80% relative to the CXCL-10 level of a patient transfused with conventionally stored blood. In a further aspect, the CXCL-10 level is increased by at least 90% relative to the CXCL-10 level of a patient transfused with conventionally stored blood. In a further aspect, the CXCL-10 level is increased by between 1 and 10%, 10 and 20%, 20 and 30%, 30 and 40%, 40 and 50%, 50 and 60%, 60 and 70%, 70 and 80%, 80 and 90%, or 90 and 95% relative to the CXCL-10 level of a patient transfused with conventionally stored blood.

Methods of the present disclosure provide for, and include, increasing the CXCL-10 levels in a patient in need thereof by between 1.5 and 10 fold comprising providing a patient with oxygen increased stored blood that has an oxygen saturation of 20% or less prior to and during storage. In an aspect, the CXCL-10 level is reduced by between 2 and 3 fold relative to the CXCL-10 level of a patient transfused with conventionally stored blood. In another aspect, the CXCL-10 level is increased by between 3 and 4 fold relative to the CXCL-10 level of a patient transfused with conventionally stored blood. In another aspect, the CXCL-10 level is increased by between 4 and 10 fold. In another aspect, the CXCL-10 level is increased by between 6 and 9 fold relative to the CXCL-10 level of a patient transfused with conventionally stored blood. In a further aspect, the CXCL-10 level is increased by between 2 and 5 fold relative to the CXCL-10 level of a patient transfused with conventionally stored blood. In another aspect, the CXCL-10 level is increased by between 10 and 100 fold relative to the CXCL-10 level of a patient transfused with conventionally stored blood.

Methods of the present disclosure provide for, and include, increasing the CXCL-10 levels in a patient in need thereof by at least 1.5 fold comprising providing a patient in need of transfusion therapy with oxygen increased stored blood that has an oxygen saturation of 20% or less prior to and during storage. In an aspect, the CXCL-10 level is increased by at least 2 fold relative to the CXCL-10 level of a patient transfused with conventionally stored blood. In another aspect, the CXCL-10 level is increased by at least 3 fold relative to the CXCL-10 level of a patient transfused with conventionally stored blood. In another aspect, the CXCL-10 level is increased by at least 4 fold relative to the CXCL-10 level of a patient transfused with conventionally stored blood. In another aspect, the CXCL-10 level is increased by at least 5 fold. In a further aspect, the CXCL-10 level is increased by at least 6 fold relative to the CXCL-10 level of a patient transfused with conventionally stored blood. In another aspect, the CXCL-10 level is increased by at least 7 fold relative to the CXCL-10 level of a patient transfused with conventionally stored blood. In another aspect, the CXCL-10 level is increased by at least 8 fold relative to the CXCL-10 level of a patient transfused with conventionally stored blood. In another aspect, the CXCL-10 level is increased by at least 9 fold relative to the CXCL-10 level of a patient transfused with conventionally stored blood. In another aspect, the CXCL-10 level is increased by at least 10 fold relative to the CXCL-10 level of a patient transfused with conventionally stored blood.

As used herein, the terms "higher", "greater" or "increased" means that the measured values of oxygen reduced and anaerobically stored blood, when compared to the measured values of otherwise equivalently treated conventionally stored blood, are at least 1 standard deviation greater, with a sample size of at least 2 for each compared measured condition.

As used herein, the terms "reduce", "reduced", "lower", "decreased" or "less" means that the measured values of oxygen reduced and anaerobically stored blood when compared to the measured values of otherwise equivalently treated normoxic or hyperoxic conventionally stored blood RBCs, are at least 1 standard deviation lower, with a sample size of at least 5 for each compared measured condition.

As used herein the term "about" refers to ±10%.

As used herein the term "less than" refers to a smaller amount and an amount greater than zero.

The terms "comprises," "comprising," "includes," "including," "having," and their conjugates mean "including but not limited to."

The term "consisting of" means "including and limited to."

The term "consisting essentially of" means that the composition, method or structure can include additional ingredients, steps and/or parts, but only if the additional ingredients, steps and/or parts do not materially alter the basic and novel characteristics of the claimed composition, method or structure.

As used herein, the singular forms "a," "an," and "the" include plural references unless the context clearly dictates otherwise. For example, the term "a compound" or "at least one compound" can include a plurality of compounds, including mixtures thereof.

As used herein, the term "blood" refers to whole blood, leukoreduced RBCs, platelet reduced RBCs, and leukocyte and platelet reduced RBCs. The term blood further includes packed red blood cells, platelet reduced packed red blood cells, leukocyte reduced packed red blood cells, and leukocyte and platelet reduced packed red blood cells. The temperature of blood can vary depending on the stage of the collection process, starting at the normal body temperature of 37° C. at the time and point of collection, but decreasing rapidly to about 30° C. as soon as the blood leaves the patient's body and further thereafter to room temperature in about 6 hours when untreated, and ultimately being refrigerated at between about 4° C. and 6° C. Human red blood cells in vivo are in a dynamic state. The red blood cells contain hemoglobin, the iron-containing protein that carries oxygen throughout the body and gives red blood its color. The percentage of blood volume composed of red blood cells is called the hematocrit. As used herein, unless otherwise limited, RBCs also includes packed red blood cells (pRBCs). Packed red blood cells are prepared from whole blood using centrifugation techniques commonly known in the art. As used herein, unless otherwise indicated, the hematocrit of pRBCs is about 70%. As used herein, oxygen reduced stored RBCs can include oxygen and carbon dioxide reduced stored RBCs. As used herein, oxygen reduced (OR) blood can include oxygen and carbon dioxide (OCR) reduced blood.

As used herein the terms "patient" and "subject" is used interchangeably to mean a person or animal in need of transfusion.

As used herein the term "trauma" includes exsanguination, hemorrhagic trauma.

As used herein the term "hemorrhagic shock" is shock brought on by a loss of circulating blood volume and/or oxygen carrying capacity. Hemorrhagic shock results from any condition associated with blood loss, internal (e.g., gastrointestinal bleeding) or external hemorrhage, and trauma (e.g., penetrating or blunt trauma), among others.

As used herein the term "adverse event" includes an event resulting from hemorrhagic shock in a hemorrhagic trauma patient.

As used herein the terms "injury", "damage", and "failure" refer to an organ not functioning properly or not functioning as is expected in a person or animal without disease or injury.

As used herein, a "unit" of blood is about 450-500 ml including anticoagulant. Suitable anticoagulants include Citrate Phosphate Dextrose Solution (CPD), citrate phosphate dextrose adenine (CPDA1), Acid Citrate Dextrose (ACD), and Anticoagulant Citrate Dextrose Solution Solution A (ACD-A).

Throughout this application, various aspects of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3," "from 1 to 4," "from 1 to 5," "from 2 to 4," "from 2 to 6," "from 3 to 6," etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques, and procedures for accomplishing a given task including, but not limited to, providing a human patient in need of a blood transfusion with oxygen reduced stored blood having an initial oxygen saturation of 20% or less and stored for at least 2 days.

The present disclosure provides for the following embodiments:

Embodiment 1. A method for treating low mean arterial pressure in a subject in need thereof comprising providing stored oxygen reduced blood to a subject having a low mean arterial pressure resulting from a hemorrhagic trauma, said oxygen reduced blood having an initial oxygen saturation of 20% or less and maintained at an oxygen saturation of 20% or less for a storage period.

Embodiment 2. The method of embodiment 1, wherein said mean arterial pressure in said subject in need thereof is increased relative to a patient receiving conventionally stored blood after said providing.

Embodiment 3. The method of embodiment 1 or 2, wherein said hemorrhagic trauma is selected from the group consisting of surgery, a penetrating wound, blunt force trauma, injury due to a fall, and injury due to a car accident.

Embodiment 4. The method of any one of embodiments 1 to 3, wherein said increasing mean arterial pressure in said subject in need thereof is at a rate faster than the rate of increase of mean arterial pressure in a subject not receiving said stored oxygen reduced blood.

Embodiment 5. The method of any one of embodiments 1 to 4, wherein said mean arterial pressure in said subject in need thereof is increased by at least 20% after said providing, relative to the mean arterial pressure of a patient transfused with conventionally stored blood.

Embodiment 6. The method of any one of embodiments 1 to 5, wherein said mean arterial pressure in said subject remains at said increased by at least 20% for at least 1 hour after said providing.

Embodiment 7. The method of any one of embodiments 1 to 5, wherein said blood is oxygen reduced and carbon dioxide reduced stored blood.

Embodiment 8. A method for reducing the amount of blood needed for transfusion in a trauma patient in need thereof comprising providing oxygen reduced blood having an oxygen saturation of 20% or less prior to and during storage.

Embodiment 9. The method of embodiment 8, wherein said blood is oxygen reduced and carbon dioxide reduced stored blood.

Embodiment 10. A method for reducing hemorrhagic shock in a trauma patient in need thereof comprising providing oxygen reduced blood having an oxygen saturation of 20% or less prior to and during storage, wherein said trauma patient comprises a lactate level of between 0.5 and 2.5 mmol/L prior to said providing, and wherein said hemorrhagic shock is reversed.

Embodiment 11. The method of embodiment 10, wherein said blood is oxygen reduced and carbon dioxide reduced stored blood.

Embodiment 12. A method of reducing a liver injury in a trauma patient in need of transfusion therapy comprising providing oxygen reduced blood having an oxygen saturation of 20% or less prior to and during storage.

Embodiment 13. A method of embodiment 9, wherein said trauma patient has improved aspartate aminotransferase (AST) levels, alanine aminotransferase (ALT) levels, or a combination thereof after said providing.

Embodiment 14. The method of embodiment 13, wherein said blood is oxygen reduced and carbon dioxide reduced stored blood.

Embodiment 15. A method of reducing a kidney failure in a trauma patient in need of transfusion therapy comprising providing oxygen reduced blood having an oxygen saturation of 20% or less prior to and during storage.

Embodiment 16. The method of embodiment 15, wherein said trauma patient has improved levels selected from neutrophil gelatinase-associated lipocalin (NGAL), serum creatinine, blood urea nitrogen (BUN), or a combination thereof.

Embodiment 17. The method of embodiment 15 or 16, wherein said blood is oxygen reduced and carbon dioxide reduced stored blood.

Embodiment 18. A method of reducing a lung injury in a trauma patient in need of transfusion therapy comprising providing oxygen reduced blood having an oxygen saturation of 20% or less prior to and during storage.

Embodiment 19. The method of embodiment 18, wherein said blood is oxygen reduced and carbon dioxide reduced stored blood.

Embodiment 20. A method of reducing lactate in a trauma patient in need thereof comprising providing oxygen reduced blood having an oxygen saturation of 20% or less prior to and during storage.

Embodiment 21. The method of embodiment 20, wherein said blood is oxygen reduced and carbon dioxide reduced stored blood.

Embodiment 22. A method of reducing aspartate amino-transferase (AST) in a trauma patient in need thereof comprising providing oxygen reduced blood having an oxygen saturation of 20% or less prior to and during storage.

Embodiment 23. A method of reducing alanine amino-transferase (ALT) in a trauma patient in need thereof comprising providing oxygen reduced blood having an oxygen saturation of 20% or less prior to and during storage.

Embodiment 24. A method of reducing blood urea nitro-gen (BUN) levels in a trauma patient in need thereof comprising providing oxygen reduced blood having an oxygen saturation of 20% or less prior to and during storage.

Embodiment 25. A method of reducing neutrophil gelati-nase-associated lipocalin (NGAL) in a trauma patient in need thereof comprising providing oxygen reduced blood having an oxygen saturation of 20% or less prior to and during storage.

Embodiment 26. A method of reducing serum creatinine in a trauma patient in need thereof comprising provid-ing oxygen reduced blood having an oxygen saturation of 20% or less prior to and during storage.

Embodiment 27. The method of any one of embodiments 22 to 26, wherein said blood is oxygen reduced and carbon dioxide reduced stored blood.

Embodiment 28. Use of donor blood to manufacture oxygen reduced blood having an oxygen saturation of 20% or less prior to and during storage for the thera-peutic application of low mean arterial pressure.

Embodiment 29. Use of donor blood to manufacture oxygen reduced blood having an oxygen saturation of 20% or less prior to and during storage for the thera-peutic application of reducing an adverse event in a hemorrhagic trauma patient, wherein said adverse event is selected from the group comprising liver injury, lung failure, kidney failure, and heart failure.

Embodiment 30. The use according to embodiments 28 or 29, wherein said manufacture comprises oxygen and carbon dioxide reduced blood.

Embodiment 31. A method of treating a patient in need thereof with stored oxygen reduced blood having an oxygen saturation of 20% or less during storage, wherein said patient in need thereof has inflammation.

Embodiment 32. The method of embodiment 31, wherein said inflammation is chronic or acute.

Embodiment 33. The method of embodiment 31, wherein said inflammation is systemic.

Embodiment 34. The method of any one of embodiments 31 to 33, wherein said inflammation is due to trauma, infection, cancer, coagulopathy, or autoimmunity.

Embodiment 35. The method of any one of embodiments 31 to 34, wherein said patient further has a fever or is at risk of developing a fever.

Embodiment 36. The method of embodiment 35, wherein said fever is at least 38° C.

Embodiment 37. The method of any one of embodiments 31 to 36, wherein said patient has increased C-Reactive Protein (CRP) levels.

Embodiment 38. The method of embodiment 37, wherein said patient has a CRP level of at least 2.0 mg/L.

Embodiment 39. The method of embodiment 38, wherein said patient has a CRP level of at least 3.0 mg/L.

Embodiment 40. The method of any one of embodiments 37 to 39, wherein said patient has a CRP level of between 3.0 and 10 mg/L.

Embodiment 41. The method of any one of embodiments 31 to 40, wherein said patient has increased levels of one or more inflammatory mediators selected from the group consisting of IL-6, IL-8, IL-10, and granulocyte-colony stimulating factor (G-CSF), compared to a patient without fever.

Embodiment 42. The method of embodiment 41, wherein said patient has a IL-6 level of at least 5 pg/mL.

Embodiment 43. The method of embodiment 41, wherein said patient has a IL-8 level of at least 29 pg/mL.

Embodiment 44. The method of embodiment 41, wherein said patient has a IL-10 level of at least 15 pg/mL.

Embodiment 45. The method of embodiment 41, wherein said patient has a G-CSF level of at least 35 pg/mL.

Embodiment 46. The method of any one of embodiments 31 to 45, wherein said patient has decreased levels of one or more inflammatory mediators selected from the group consisting of CCLS and CXCL10, compared to a patient without fever.

Embodiment 47. The method of embodiment 46, wherein said patient has a CCLS level of at least 380 pg/mL.

Embodiment 48. The method of embodiment 46, wherein said patient has a CXCL10 level of at least 270 pg/mL.

Embodiment 49. The method of any one of embodiments 31 to 48, wherein said patient has liver damage.

Embodiment 50. The method of any one of embodiments 31 to 49, wherein said patient has lung damage.

Embodiment 51. The method of any one of embodiments 31 to 50, wherein said patient has splenic damage.

Embodiment 52. The method of any one of embodiments 31 to 51, wherein said patient has kidney damage.

Embodiment 53. The method of any one of embodiments 31 to 52, wherein said patient has bone damage.

Embodiment 54. The method of any one of embodiments 31 to 53, wherein said treating reduces red blood cell adhesion to thrombospondin in said patient compared to a patient treated with conventionally stored blood.

Embodiment 55. The method of embodiment 54, wherein said thrombospondin is reduced by at least 10%.

Embodiment 56. The method of any one of embodiments 31 to 55, wherein said stored oxygen reduced blood is oxygen and carbon dioxide reduced blood.

Embodiment 57. A method of improving transfusion in a sickle cell patient in need thereof comprising providing stored oxygen reduced blood to a patient having sickle cell disease, wherein said oxygen reduced blood has an oxygen saturation of 20% or less during storage.

Embodiment 58. The method of embodiment 57, wherein said sickle cell disease is sickle cell anemia.

Embodiment 59. The method of embodiment 57, wherein said sickle cell disease is sickle cell crisis.

Embodiment 60. The method of embodiment 57, wherein said sickle cell disease is selected from the group consisting of hemoglobin SS (HbSS), hemoglobin SC (HbSC), hemoglobin S beta thalassemia+(HbSB+), hemoglobin S (beta-zero) thalassemia (HbSB), hemoglobin SD (HbSD), hemoglobin SE (HbSE), and hemoglobin SO (HbSO).

Embodiment 61. The method of any one of embodiments 57 to 60, wherein said improving comprises reducing the number of dactylitis (hand-foot syndrome) occurrences by at least 10% compared to a patient receiving conventionally stored blood.

Embodiment 62. The method of any one of embodiments 57 to 61, wherein said improving comprises reducing the number of pain crises by at least 10% compared to being treated with conventionally stored blood.

Embodiment 63. The method of any one of embodiments 57 to 62, wherein said improving comprises reducing complications due to anemia selected from the group consisting of fatigue, irritability, dizziness, difficulty breathing, pale skin color, jaundice, slow growth, and delayed puberty.

Embodiment 64. The method of any one of embodiments 57 to 63, wherein said improving comprises reducing the occurrence of infection.

Embodiment 65. The method of any one of embodiments 57 to 64, wherein said improving comprises reducing spleen damage.

Embodiment 66. The method of embodiment 65, wherein said spleen damage is splenic sequestration.

Embodiment 67. The method of embodiment 65, wherein said spleen damage is splenic enlargement.

Embodiment 68. The method of any one of embodiments 57 to 67, wherein said improving comprises reducing or preventing stroke.

Embodiment 69. The method of any one of embodiments 57 to 68, wherein said previously stored oxygen reduced blood has higher 24-hr recovery compared to conventionally stored blood after said transfusion.

Embodiment 70. The method of any one of embodiments 57 to 69, wherein said previously stored oxygen reduced blood has increased deformability compared to conventionally stored blood.

Embodiment 71. The method of any one of embodiments 57 to 70, wherein said oxygen reduced blood has increased deformability compared to conventionally stored blood and when in the presence of sickle cell plasma.

Embodiment 72. The method of any one of embodiments 57 to 71, further comprising reducing carbon dioxide in said oxygen reduced blood.

Embodiment 73. A method of decreasing the number of vaso-occlusion episodes in a patient in need thereof comprising providing stored oxygen reduced blood to a patient in need thereof, wherein said oxygen reduced blood has an oxygen saturation of 20% or less during storage and said decreasing vaso-occlusion episodes comprises decreasing adhesion of red blood cells to endothelial cells.

Embodiment 74. The method of embodiment 73, wherein said patient in need thereof has sickle cell disease.

Embodiment 75. The method of embodiment 73 or 74, wherein said patient in need thereof has inflammation.

Embodiment 76. The method of any one of embodiments 73 to 75, wherein said decreasing red blood cell adhesion is to endothelial cells expressing thrombospondin.

Embodiment 77. The method of any one of embodiments 73 to 76, wherein said decreasing red blood cell adhesion is to endothelial cells expressing Vascular Cell Adhesion Molecule-1 (VCAM-1).

Embodiment 78. The method of any one of embodiments 73 to 77, wherein said decreasing red blood cell adhesion is to endothelial cells expressing laminin.

Embodiment 79. The method of any one of embodiments 76 to 78, wherein said adhesion is decreased by at least 10% compared to conventionally stored blood.

Embodiment 80. The method of any one of embodiments 76 to 79, wherein said adhesion is decreased by at least 20% compared to conventionally stored blood.

Embodiment 81. The method of any one of embodiments 76 to 80, wherein said adhesion is decreased by between 10 and 50%.

Embodiment 82. The method of any one of embodiments 73 to 81, wherein said sickle cell disease is sickle cell anemia.

Embodiment 83. The method of any one of embodiments 73 to 81, wherein said sickle cell disease is sickle cell crisis.

Embodiment 84. The method of any one of embodiments 73 to 83, wherein said sickle cell disease is selected from the group consisting of hemoglobin SS (HbSS), hemoglobin SC (HbSC), hemoglobin S beta thalassemia+(HbSB+), hemoglobin S (beta-zero) thalassemia (HbSB), hemoglobin SD (HbSD), hemoglobin SE (HbSE), and hemoglobin SO (HbSO).

Embodiment 85. The method of any one of embodiments 73 to 83, further comprising reducing carbon dioxide in said oxygen reduced blood.

Embodiment 86. A method of decreasing red blood cell adhesion to endothelial cells in a patient in need thereof comprising providing stored oxygen reduced blood to a patient having sickle cell disease, wherein said oxygen reduced blood has an oxygen saturation of 20% or less during storage.

Embodiment 87. Oxygen reduced blood having an oxygen saturation of 20% or less during storage, for use in the treatment of sickle cell disease.

Embodiment 88. The oxygen reduced blood according to embodiment 87, wherein said blood is oxygen and carbon dioxide reduced blood.

Embodiment 89. Oxygen reduced blood having an oxygen saturation of 20% or less during storage, for use in the treatment of inflammation.

Embodiment 90. The oxygen reduced blood according to embodiment 89, wherein said blood is oxygen and carbon dioxide reduced blood.

Embodiment 91. Stored oxygen reduced blood comprising an oxygen saturation of 20% or less for the use in the treatment of vaso-occlusion episodes, wherein said treatment decreases the number of vaso-occlusion episodes in a patient in need thereof, and said decreasing vaso-occlusion episodes comprises decreasing adhesion of red blood cells to endothelial cells.

Embodiment 92. The stored oxygen reduced blood according to embodiment 91, wherein said blood is oxygen and carbon dioxide reduced stored blood.

Embodiment 93. Use of oxygen reduced blood having an oxygen saturation of 20% or less during storage for the treatment of inflammation in a patient in need thereof.

Embodiment 94. Use of oxygen reduced blood having an oxygen saturation of 20% or less during storage for the treatment of sickle cell in a patient in need thereof.

Embodiment 95. The use of oxygen reduced blood according to embodiment 94, wherein said blood is oxygen and carbon dioxide reduced blood.

Embodiment 96. Use of oxygen reduced blood as substantially shown and described.

Embodiment 97. Use of oxygen and carbon dioxide reduced blood as substantially shown and described.

Embodiment 98. A kit comprising an oxygen impermeable blood storage bag comprising stored oxygen reduced blood having an oxygen saturation of 20% or less during storage, a filter, and a drip chamber.

Embodiment 99. The kit of embodiment 98, further comprising a device for adding a gas to the stored oxygen reduced blood prior to transfusion.

Embodiment 100. The kit of embodiment 98 or 99, further comprising tubing for transfusing said stored oxygen reduced blood to a patient in need thereof Embodiment 101. Use of a kit of any one of embodiments 98 to 100, for the treatment of sickle cell disease or inflammation in a patient in need thereof.

While the present disclosure has been described with reference to particular embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular embodiments disclosed as the best mode contemplated for carrying out the present disclosure, but that the present disclosure will include all embodiments falling within the scope and spirit of the appended claims.

EXAMPLES

Example 1: Collection of Blood and Sample Preparation

Each pool of red blood cells are collected from a total of 12-14 rats in CP2D anticoagulant. The pooled blood is leukoreduced using neonatal leukoreduction filter, component separated and RBCs are stored in AS-3 additive solution. Total of two pools of RBCs are collected. Each pool is split four ways: Unprocessed control (C), sham control (SC), oxygen-reduced (OR) and oxygen and carbon dioxide reduced (OCR). For C, SC, OR and OCR units, RBC subunit is processed by transferring into 80 mL PVC blood transfer bag and final RBC products are made by gas exchange process. The RBC bags except for C are filled with 100% $N_2$ (for OR), or 95% $N_2$/5% $CO_2$ (for OCR) or air (SC) through sterile filter and gently rotated on its long side at 2-3 RPM (except for C). For OR and OCR units, after 10 minutes, gas is removed through the filter and fresh gas is introduced for subsequent gas exchange process. This process is repeated 5-8 times until target %502 of 5-10% as measured by ABL-90 cooximeter (Radiometer Copenhagen) is achieved. SC unit is rotated without any gas exchange for 60 minutes. OR and OCR units are stored anaerobically in a $N_2$-filled canister, while C and SC units are stored in ambient air. All units are stored for 3 weeks at 4° C. and sampled at days 0 or 1, 7, 14, 21, and 28. Two pools were prepared and stored.

Figure 2:
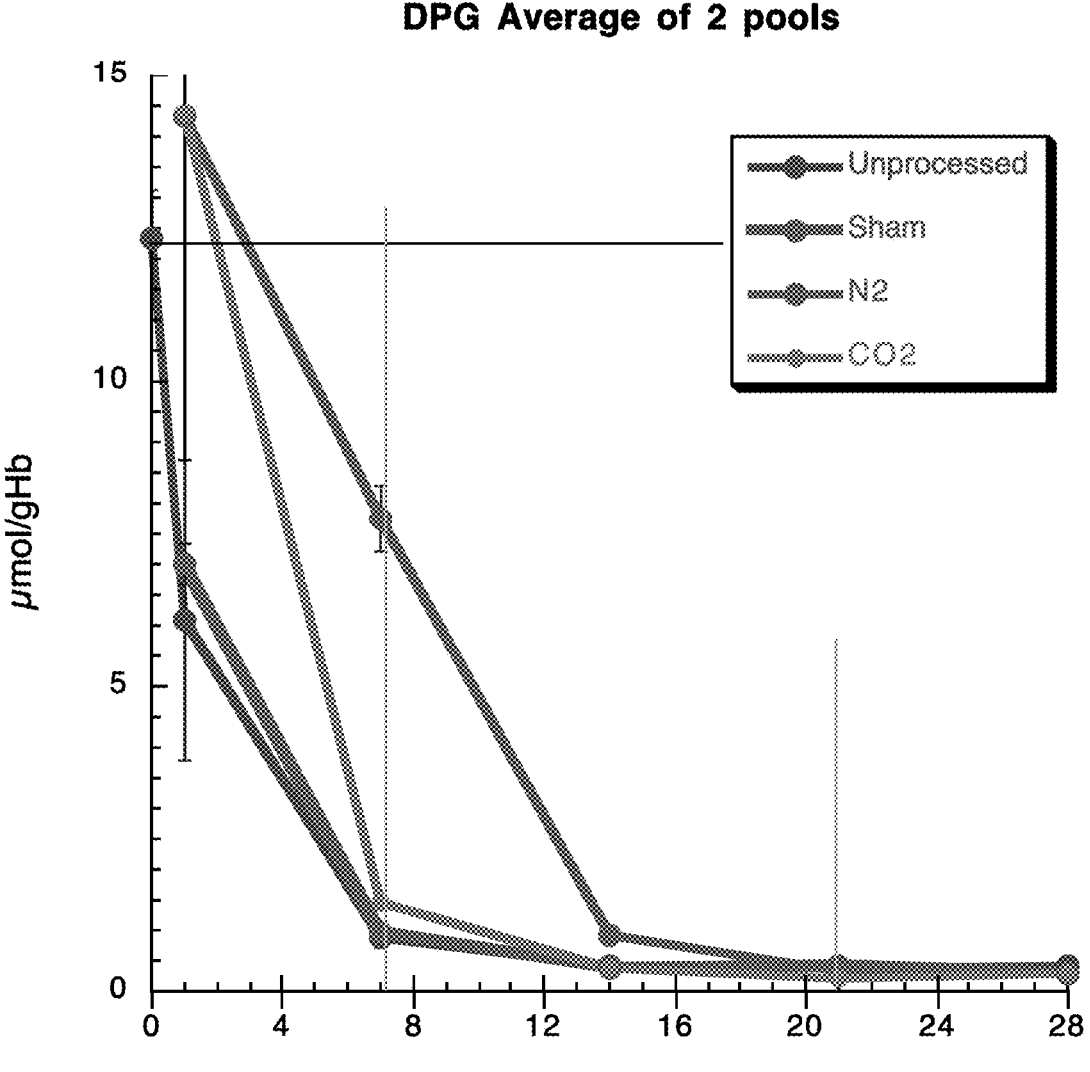
FIG. 2 is a graph presenting the results of an exemplary embodiment according to the present disclosure, comparing 2,3-DPG levels of conventionally stored RBCs (unprocessed; control), sham control (SC), oxygen reduced RBCs ($N_2$; OR), and oxygen and carbon dioxide reduced RBCs ($CO_2$; OCR).

On days 0, 1, 7, 14, 21, and 28, ATP, 2,3-DPG, and hemolysis analysis are performed. As shown in FIG. 1, ATP levels are higher in OR-blood at day 21 and OCR-blood at days 7, 14, 21, and 28 compared to conventionally stored blood (control). OR-blood also has higher levels of 2.3-DPG at days 2, 7, and 14, compared to control. OCR-blood also shows a higher level of 2,3-DPG on days 2, 7, and 14 compared to control. See FIG. 2.

Example 2: Recovery of Oxygen Reduced Blood

Figure 3:
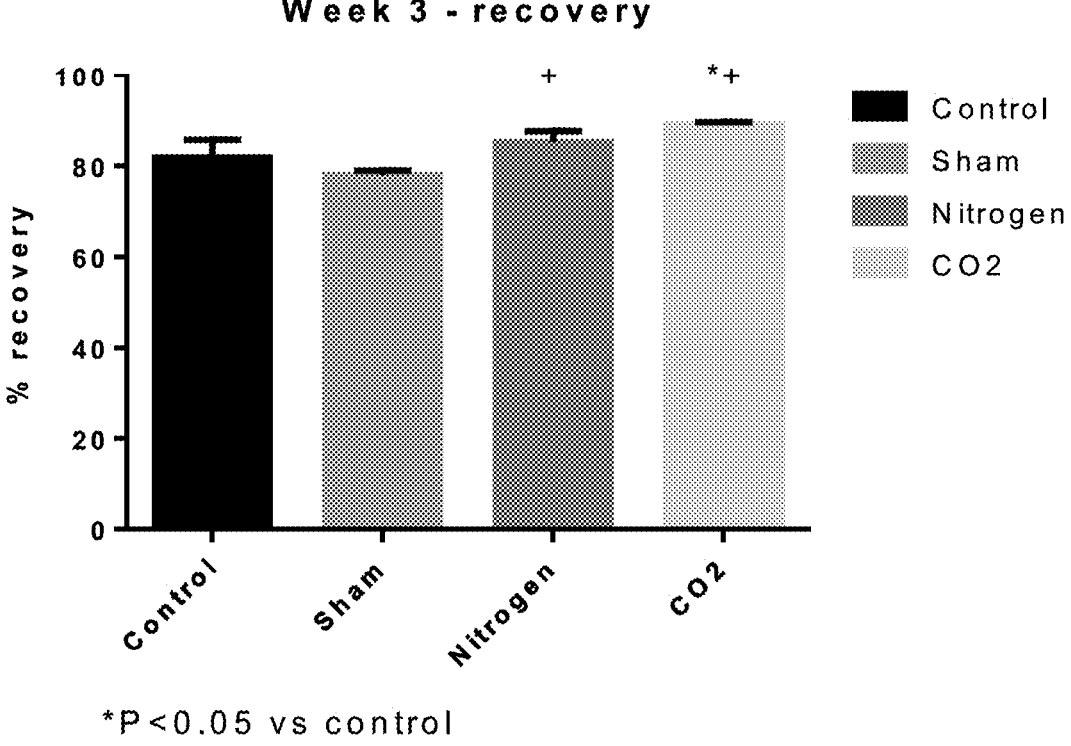
FIG. 3 is a graph presenting the results of an exemplary embodiment according to the present disclosure, presenting a comparison of the percent recovery of control, sham, OR-RBCs, and OCR-RBCs transfused into an animal.

A small volume (less than 200 µL) of Control, OR-, and OCR-blood stored for 3 weeks is labeled with techniteum-99m. Animals are transfused with labeled RBC (less than 200 uL) and circulating radioactivity is measured periodically up to 24 hours in order to estimate fraction of transfused RBC surviving 24 hours after transfusion. As shown in FIG. 3, significantly more OR- and OCR-RBCs are recovered compared to control RBCs when RBCs were stored for three weeks.

Example 3: Rat Model of Hemorrhagic Shock Resuscitation

Collection of blood and sample preparation: Each pool of red blood cells are collected from a total of 12-14 rats in CP2D anticoagulant. The pooled blood is leukoreduced using neonatal leukoreduction filter, component separated and RBCs are stored in AS-3 additive solution. Total of six pools of RBCs are collected. Two pools are prepared for conventional storage (control). Two pools are depleted of oxygen (oxygen reduced; OR), and the remaining two pools of blood are depleted of oxygen and carbon dioxide (oxygen and carbon dioxide reduced; OCR). Each of the four pools to be reduced is processed by transferring RBCs into 600 mL PVC blood transfer bag and final RBC products are made by gas exchange process. The RBC bag is filled with 100% $N_2$ (for OR), or 95% $N_2$/5% $CO_2$ (for OCR) through sterile filter and gently rotated on its long side at 60-90 RPM. After 10 minutes, gas is removed through the filter and fresh gas is introduced for subsequent gas exchange process. This process is repeated 5-8 times until target % SO2 of 5-10% as measured by ABL-90 cooximeter (Radiometer Copenhagen) is achieved. OR and OCR blood is stored anaerobically in a $N_2$-filled canister.

Studies are performed in Sprague-Dawley rats (Charles River Laboratories, Boston, MA) weighing 150-200 grams (g). Briefly, animals are anesthetized by administering 40 mg/kg of sodium pentobarbital intraperitoneally. Animals are placed in the supine position on a heating pad to maintain core body temperature at 37 C. Animals are prepared with: (i) a left jugular vein and left femoral artery catheterization, (ii) tracheotomy (polyethylene-90 tube), and (iii) left ventricle (LV) conductance catheter introduction through the right carotid artery. Animals are mechanically ventilated (TOPO ventilator, Kent Scientific, Torrington, CT) using room air, with a respiration rate of 50-70 breaths per min and a peak inspiratory pressure of 10-15 cmH2O. After instrumentation, volatile anesthesia (1.5%/vol Isoflurane, Drager-werk AG, Laubeck, Germany) is administered using a vaporizer connected to the ventilator. Depth of anesthesia is continually verified via toe pinch, as needed, isoflurane was increased by 0.1%/vol to prevent animal discomfort.

Anesthetized animals are hemorrhaged by withdrawing 50% of the animal's blood volume (BV; estimated 7% of body weight) via the femoral artery catheter within 10 min, placing the animals in a hypovolemic shock condition. The hypovolemic shock condition is maintained for 30 min. Resuscitation is implemented by infusion of previously stored RBCs at 300 microliters per min (μL/min) via the femoral artery until Mean arterial pressure (MAP) is stabilized at 90% of the baseline during 60 minutes resuscitation period. At 10, 20, 30, 45 and 60 minutes during this period, MAP and heart rate (HR) are obtained from a femoral artery catheter (PowerLab, AD Instruments, Colorado Springs, CO). After 60 mins, hematocrit (Hct) is measured via centrifugation of heparinized capillary tubes. Hemoglobin (Hb), lactate, glucose, K+, Na+, pH, arterial blood gas are determined by ABL90 cooximeter (Radiometer, Copenhagen). Indices of cardiac function and systemic values (MAP, HR, Hct, Hb, and blood gases) are monitored at baseline (BL), during shock, and 10 (Early R), 20, 30, 45, and 60 (Late R) mins post resuscitation. Animals are euthanized at the end of the experiment.

Example 4: Hematocrit Analysis in a Rat Model of Hemorrhagic Shock

Figure 4A:
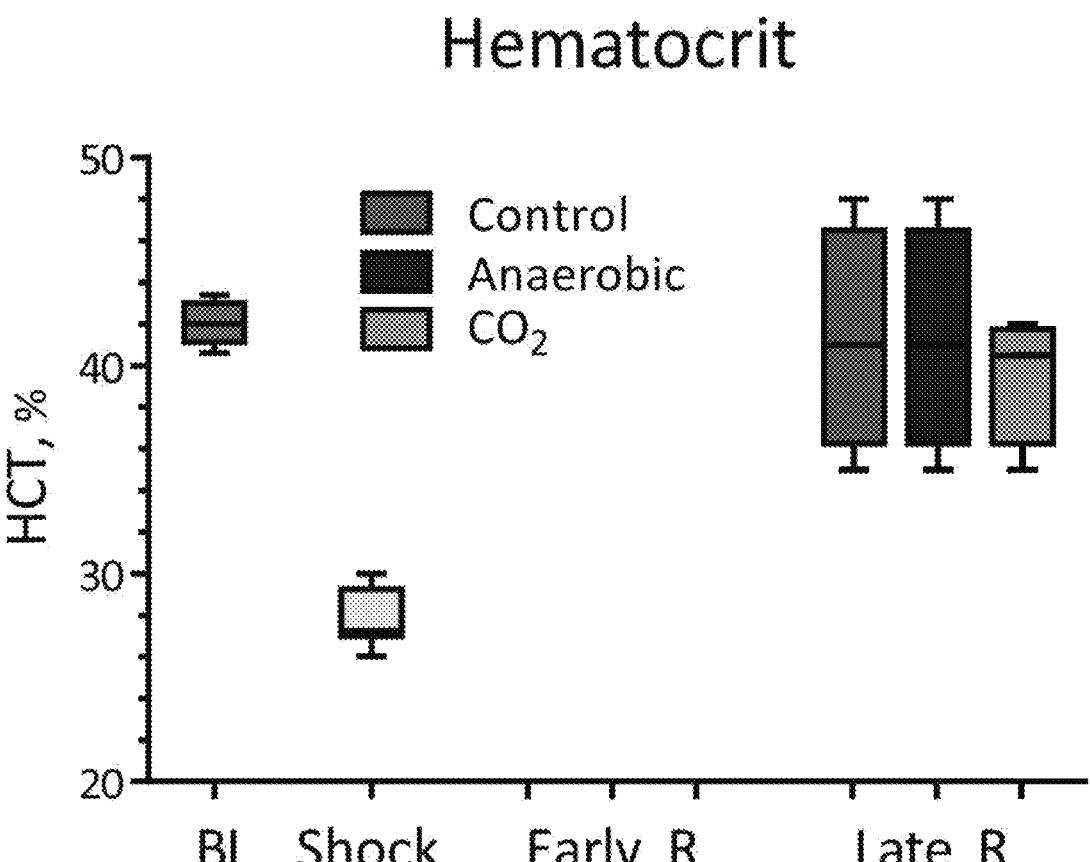
FIGS. 4A and 4B are graphs presenting the results of an exemplary embodiment according to the present disclosure, presenting a comparison of the percent hematocrit in animals resuscitated with control, OR-RBCs, and OCR-RBCs stored for 1 week (FIG. 4A) or 3 weeks (FIG. 4B). BL (baseline) identifies animals not under shock conditions. Shock identifies animals under hemorrhagic shock. Early R identifies a resuscitation period of 10 mins. Late R identifies a resuscitation period of 60 mins.
Figure 4B:
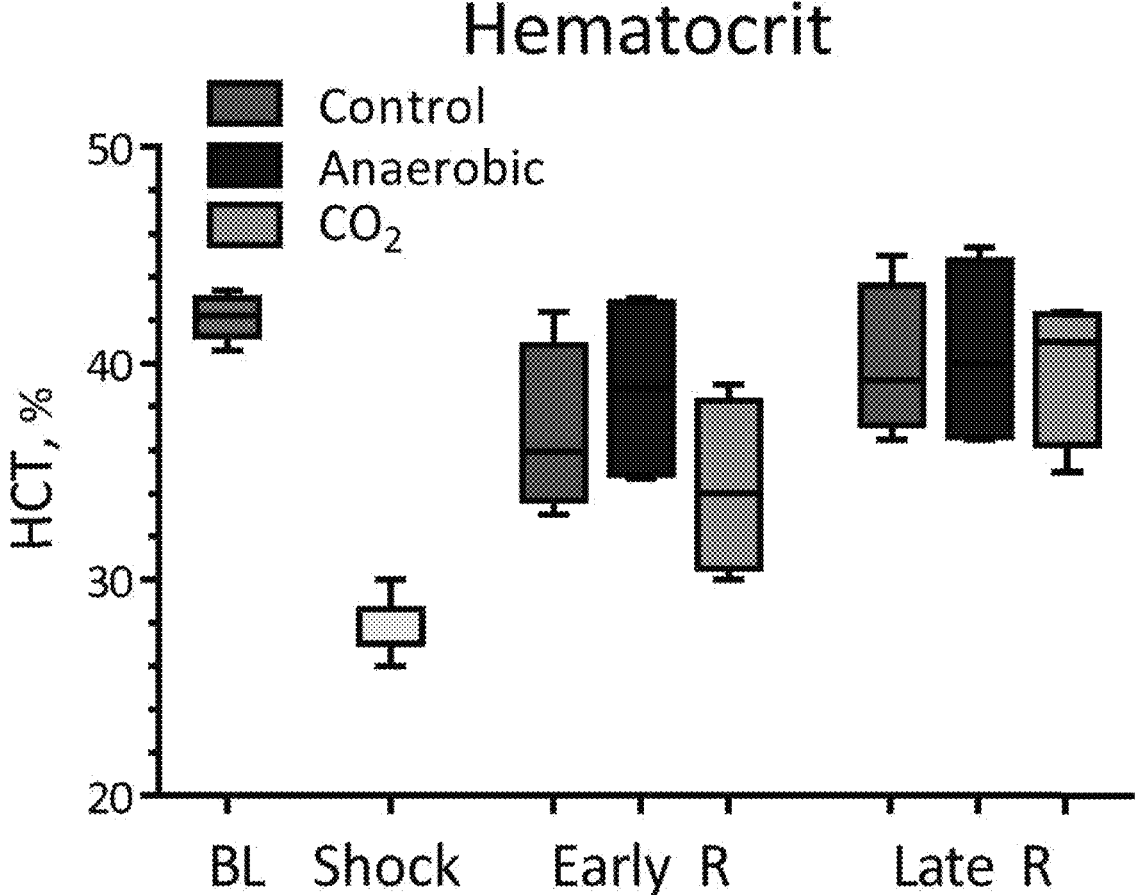

Hematocrit (Hct) is reduced by approximately 30 to 40% after hypovolemic shock is induced. Providing conventionally, OR, or OCR blood stored for 1 week is capable of restoring hematocrit to normal levels. See FIG. 4A. However, as shown in FIG. 4B, OR-blood stored for one week show an increased percent hematocrit compared to control and OCR-blood after 10 mins of resuscitation (Early R). The percent hematocrit of OR-blood remains improved compared to control after 60 mins (Late R) of resuscitation.

Example 5: Mean Arterial Pressure Changes with Oxygen Reduced Blood

Figure 5A:
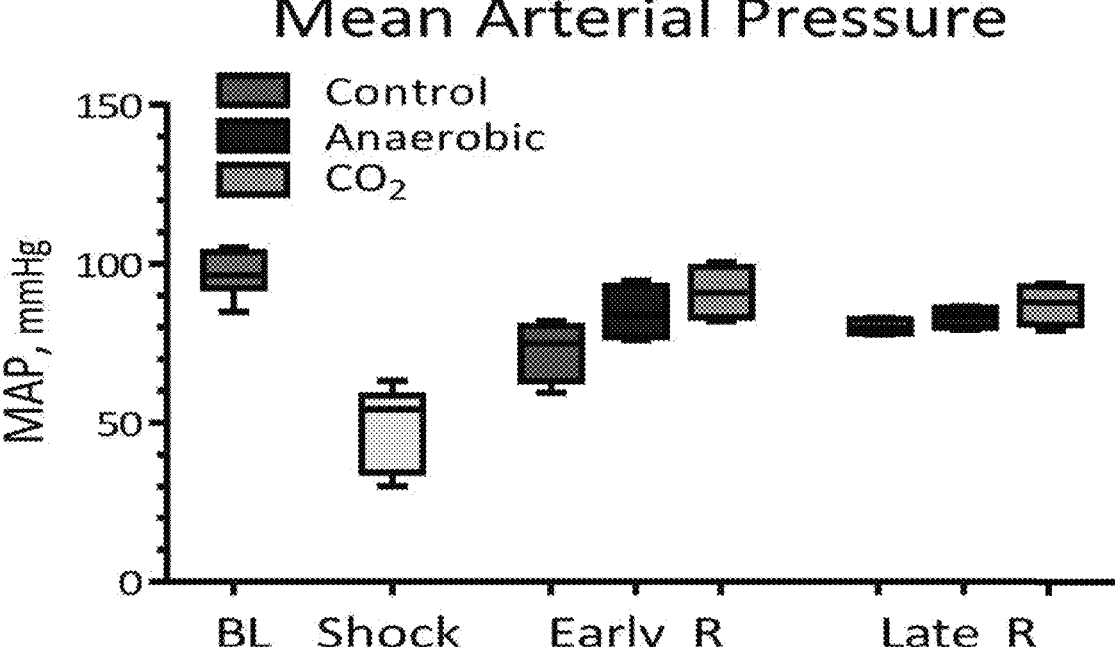
FIGS. 5A and 5B are graphs presenting the results of an exemplary embodiment according to the present disclosure, providing a comparison of the mean arterial pressure (MAP) in animals resuscitated with control, OR-RBCs, and OCR-RBCs stored for 1 week (FIG. 5A) or 3 weeks (FIG. 5B). BL (baseline) identifies animals not under shock conditions. Shock identifies animals under hemorrhagic shock. Early R identifies a resuscitation period of 10 mins. Late R identifies a resuscitation period of 60 mins.
Figure 5B:
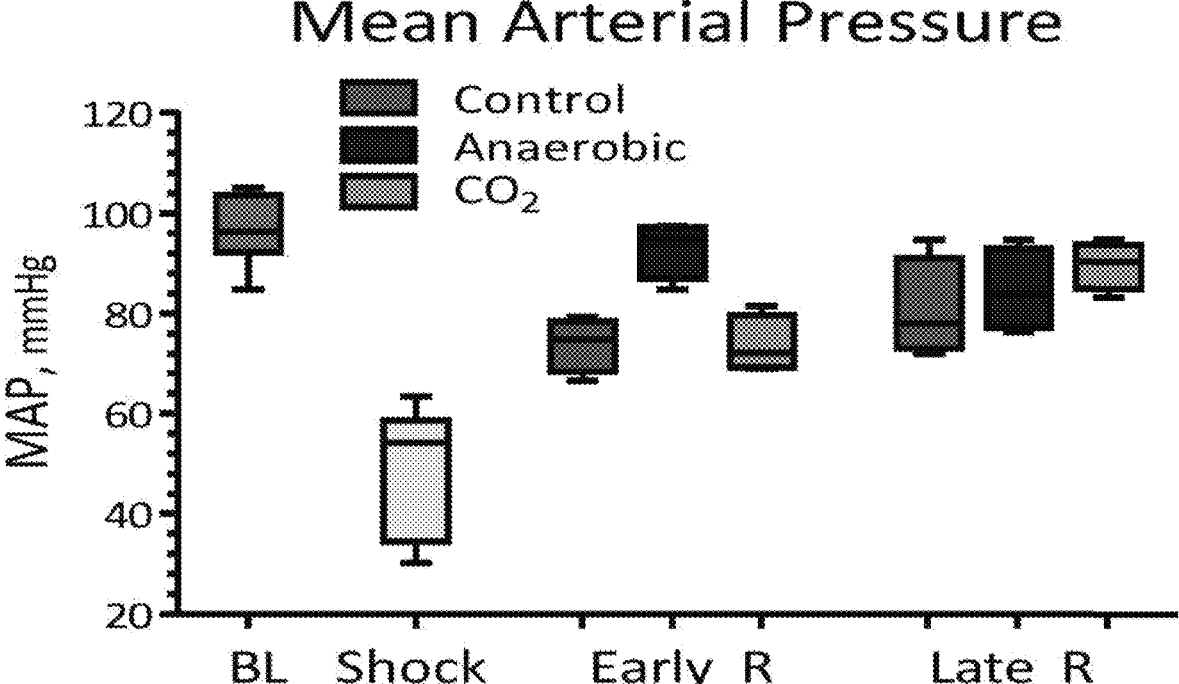
Figure 6A:
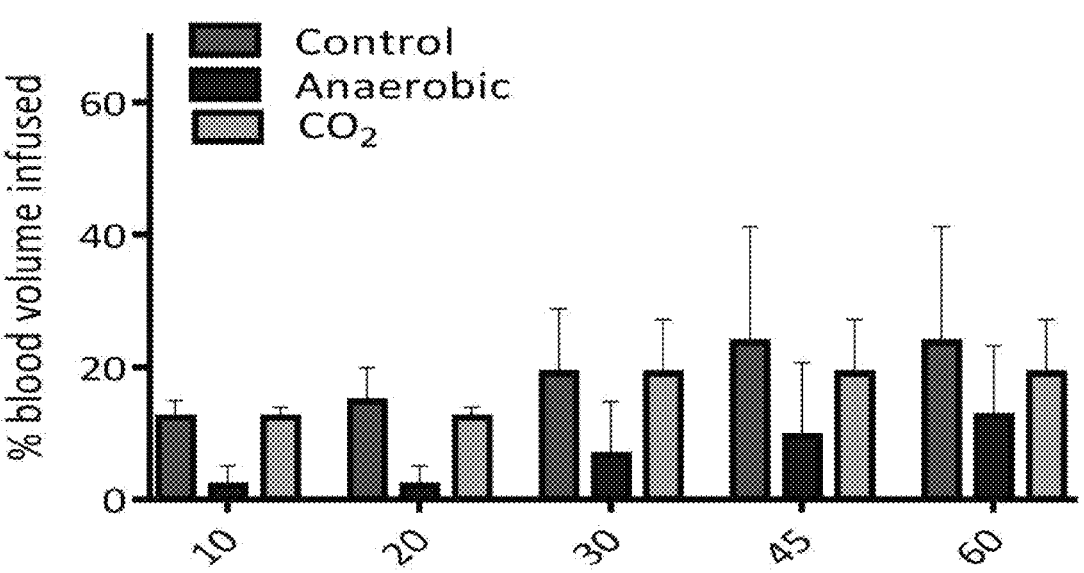
FIGS. 6A and 6B are graphs presenting the results of an exemplary embodiment according to the present disclosure, providing a comparison of the percent blood volume provided to animals during resuscitation after 10, 20, 30, 45, and 60 mins. Control, OR-RBCs, and OCR-RBCs stored for 1 week (FIG. 6A) or 3 weeks (FIG. 6B) are compared.
Figure 6B:
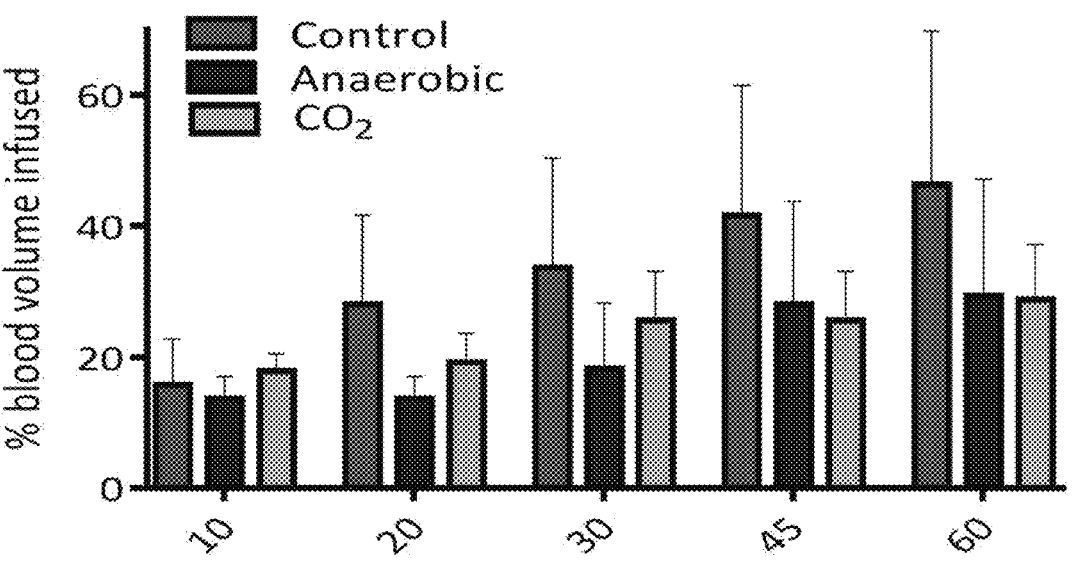

Mean arterial pressure (MAP) is obtained from the femoral artery catheter (PowerLab, AD Instruments, Colorado Springs, CO). As shown in FIG. 5A, baseline MAP is between 80 and 110 mmHg. MAP is reduced to between 20 and 60 mmHg during hemorrhagic shock. Resuscitation of animals with OR and OCR blood stored for one week increases the MAP to approximately 80 and 90 mmHg, respectively. As shown in FIG. 5B, resuscitation with OR blood, after 10 mins, is able to restore MAP to normal range compared to control. Control and OCR stored blood is able to restore MAP to a normal range after 60 mins of resuscitation. The amount of blood required to resuscitate and preserve hemodynamics with conventionally stored RBCs (control) was greater than OR and OCR RBCs required. See FIG. 6A and FIG. 6B.

Example 6: Metabolic Reaction to Hemorrhagic Shock

Figure 8B:
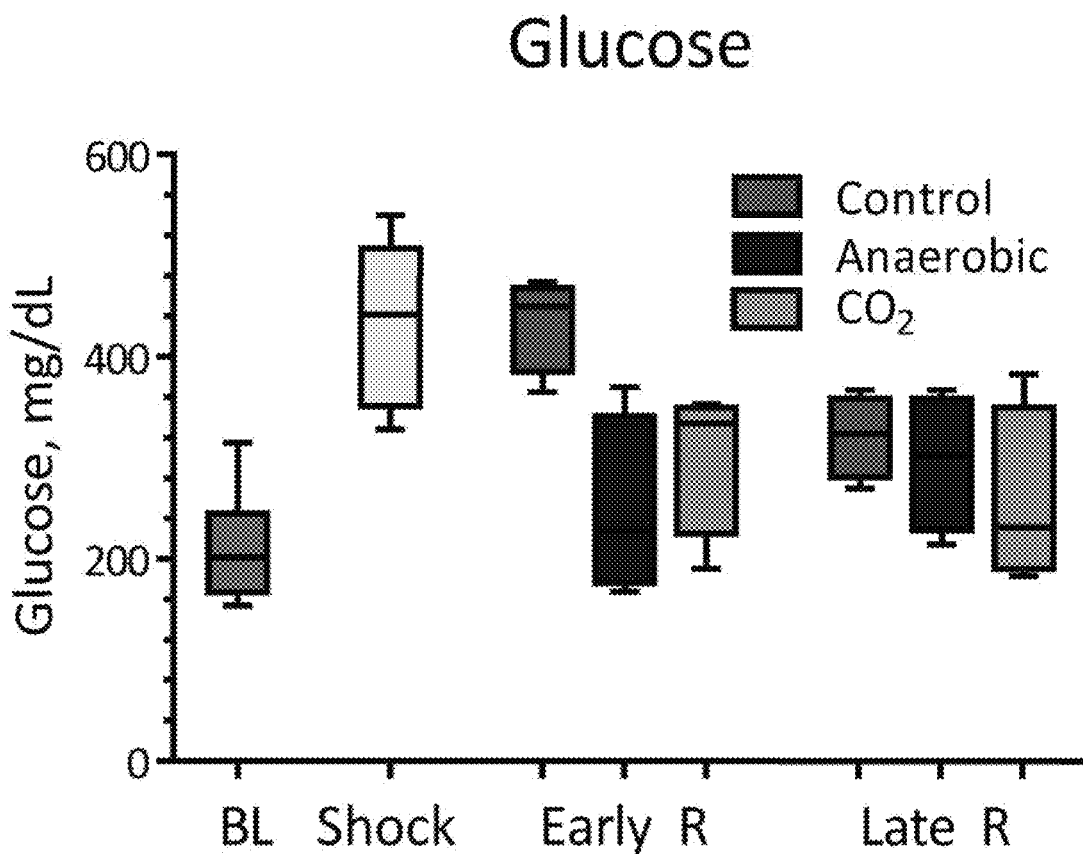

Hemorrhagic shock in animals increases the lactate level from about 2 mmol/L to between about 8 and 14 mmol/L. Resuscitation with OR and OCR RBCs stored for one week reduces lactate levels to near normal levels after just 10 mins of resuscitation. See FIG. 7A. Lactate levels of animals resuscitated with control blood are similar to lactate levels of animals in hemorrhagic shock. Animals treated with control, OR and OCR RBCs for 60 mins show similar lactate levels. As shown, in FIG. 7B, OR RBCs stored for 3 weeks are also able to reduce lactate levels compared to control after 10 mins of resuscitation. However, after 80 mins of resuscitation OCR RBCs restored lactate levels to a normal range. Control and OR RBCs were able to reduce lactate levels but not to the normal range of 1 to 3 mmol/L. Analysis of glucose levels show that the normal range of about 160 mg/dL to about 240 mg/dL glucose is increased to a range of about 320 to about 510 mg/dL in animals under hemorrhagic shock. See FIG. 8A and FIG. 8B. Both OR and OCR RBCs stored for one week decrease glucose levels compared to control after 10 mins of resuscitation. All three samples restored glucose levels to the normal range after 60 mins of resuscitation. As shown in FIG. 8B, OR and OCR RBCs stored for three weeks are also able to decrease glucose levels compared to control after 10 mins of resuscitation. Unlike the RBCs stored for one week, only OR and OCR RBCs were able to restore glucose within the normal range. Thus, both lactate and glucose levels are reduced faster in OR and OCR RBCs compared to control RBCs.

Example 7: Vital Organ Injury and Inflammation

Figure 9A:
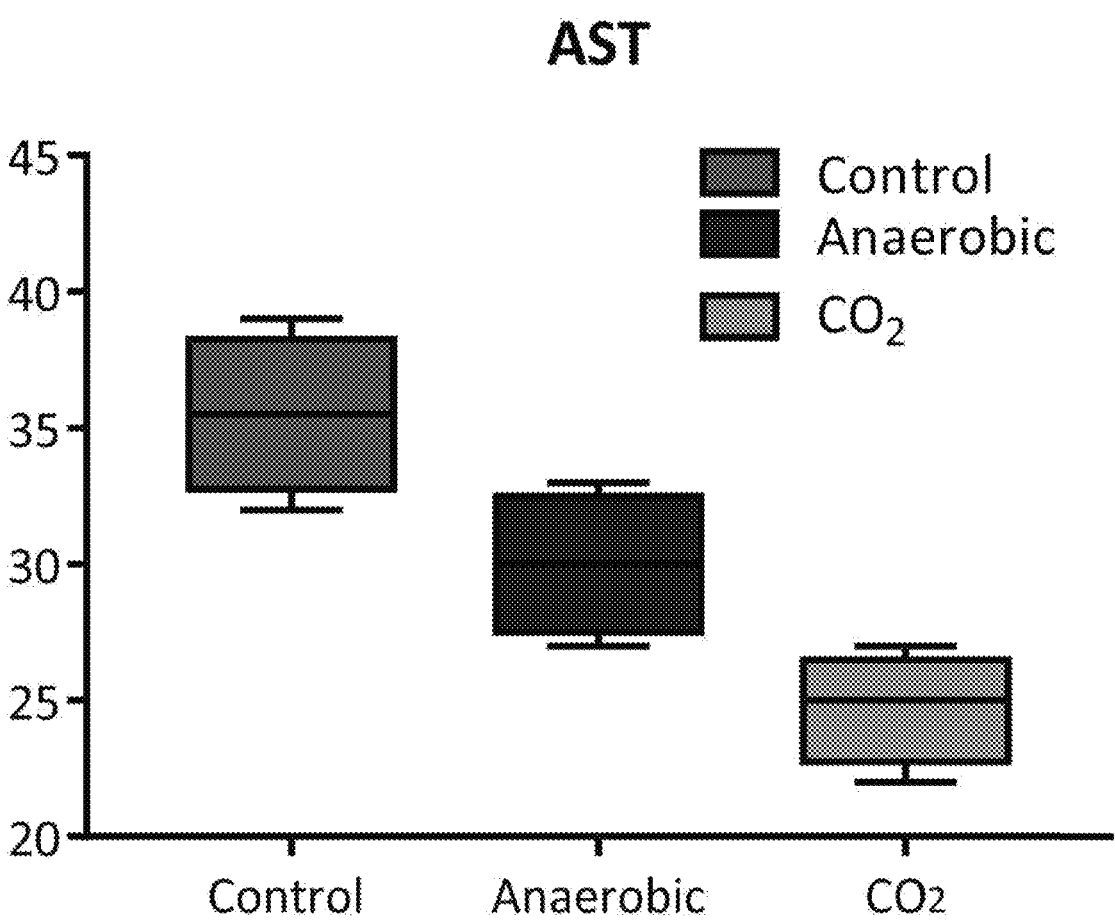
FIGS. 9A and 9B are graphs presenting the results of an exemplary embodiment according to the present disclosure, providing a comparison of the amount of AST in animals resuscitated with control, OR-RBCs, and OCR-RBCs stored for 1 week (FIG. 9A) or 3 weeks (FIG. 9B).
Figure 9B:
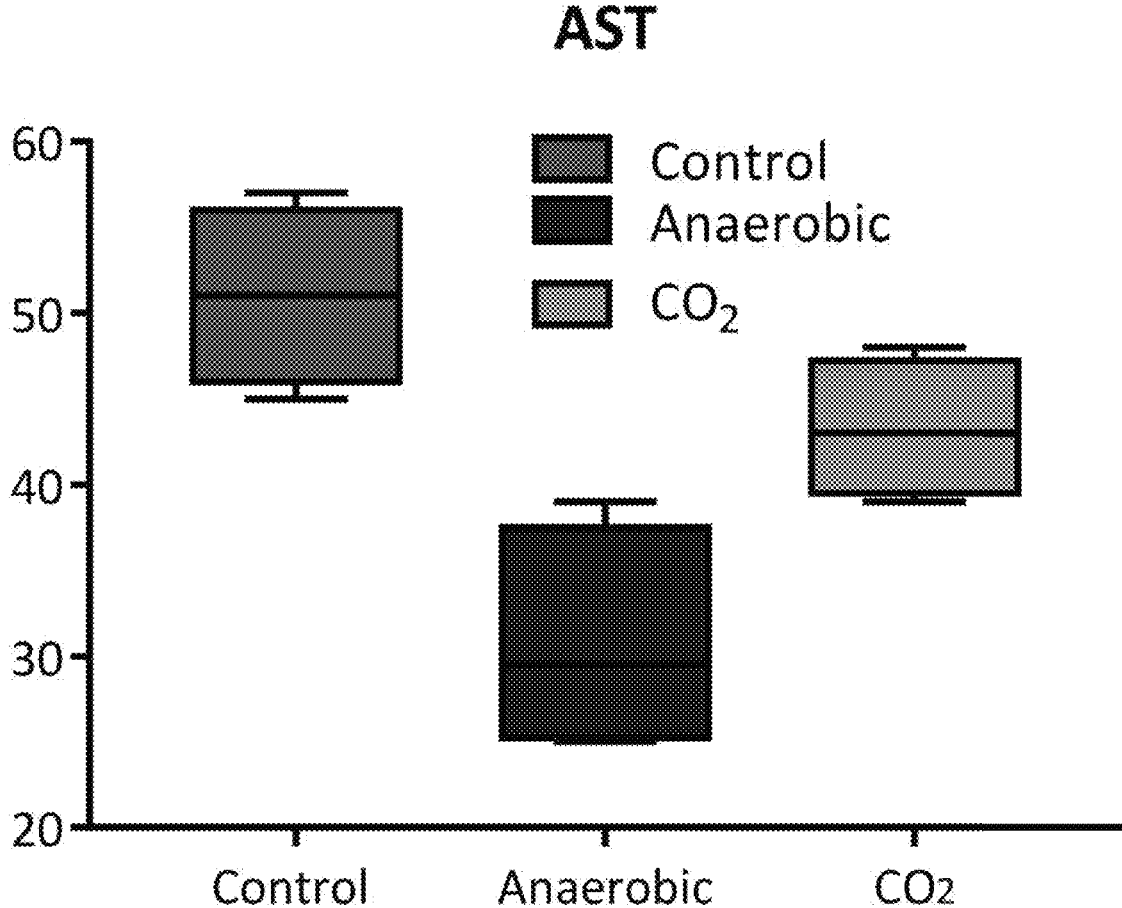
Figure 10A:
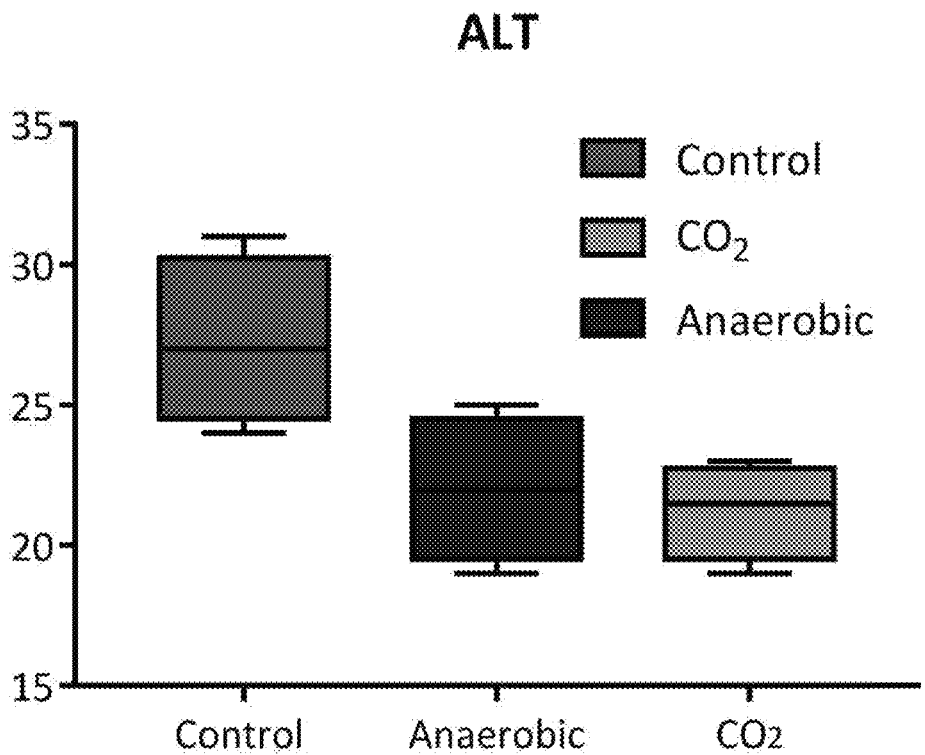
FIGS. 10A and 10B are graphs presenting the results of an exemplary embodiment according to the present disclosure, providing a comparison of the amount of ALT in animals resuscitated with control, OR-RBCs, and OCR-RBCs stored for 1 week (FIG. 10A) or 3 weeks (FIG. 10B).
Figure 10B:
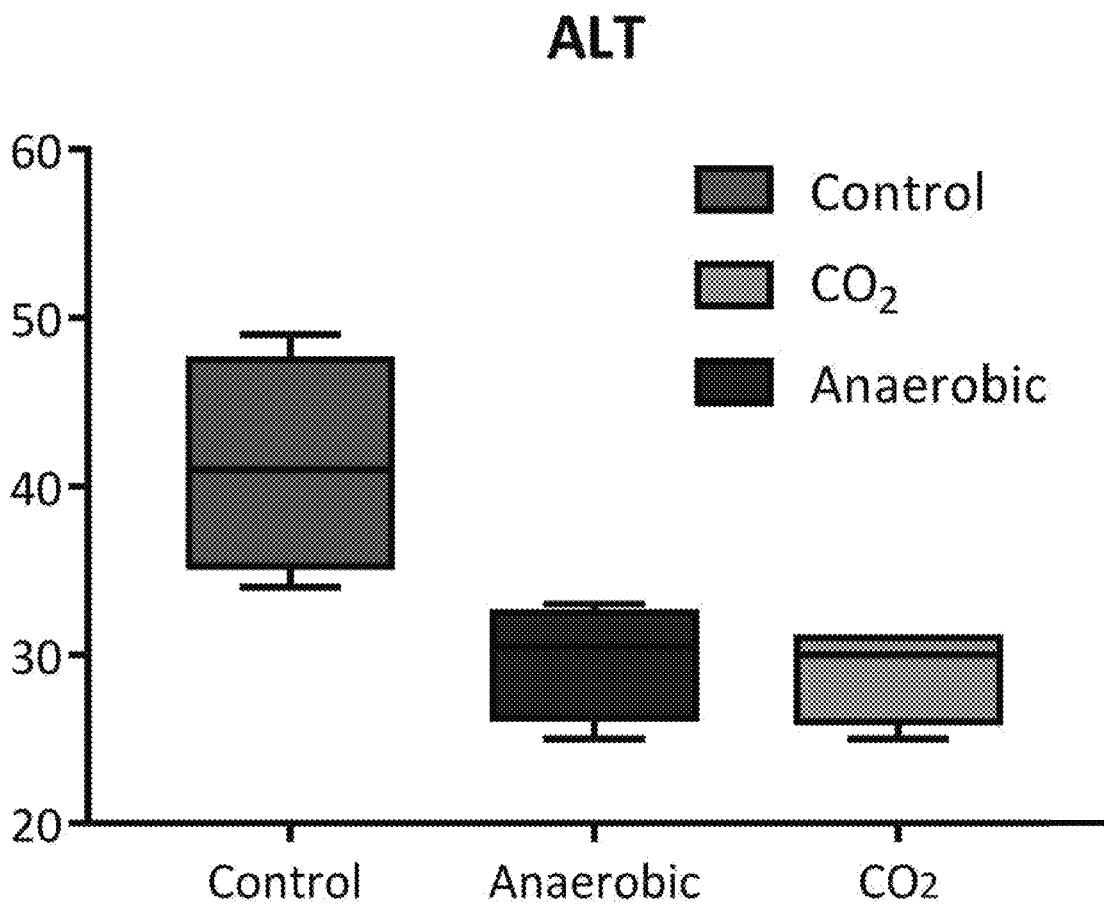
Figure 11A:
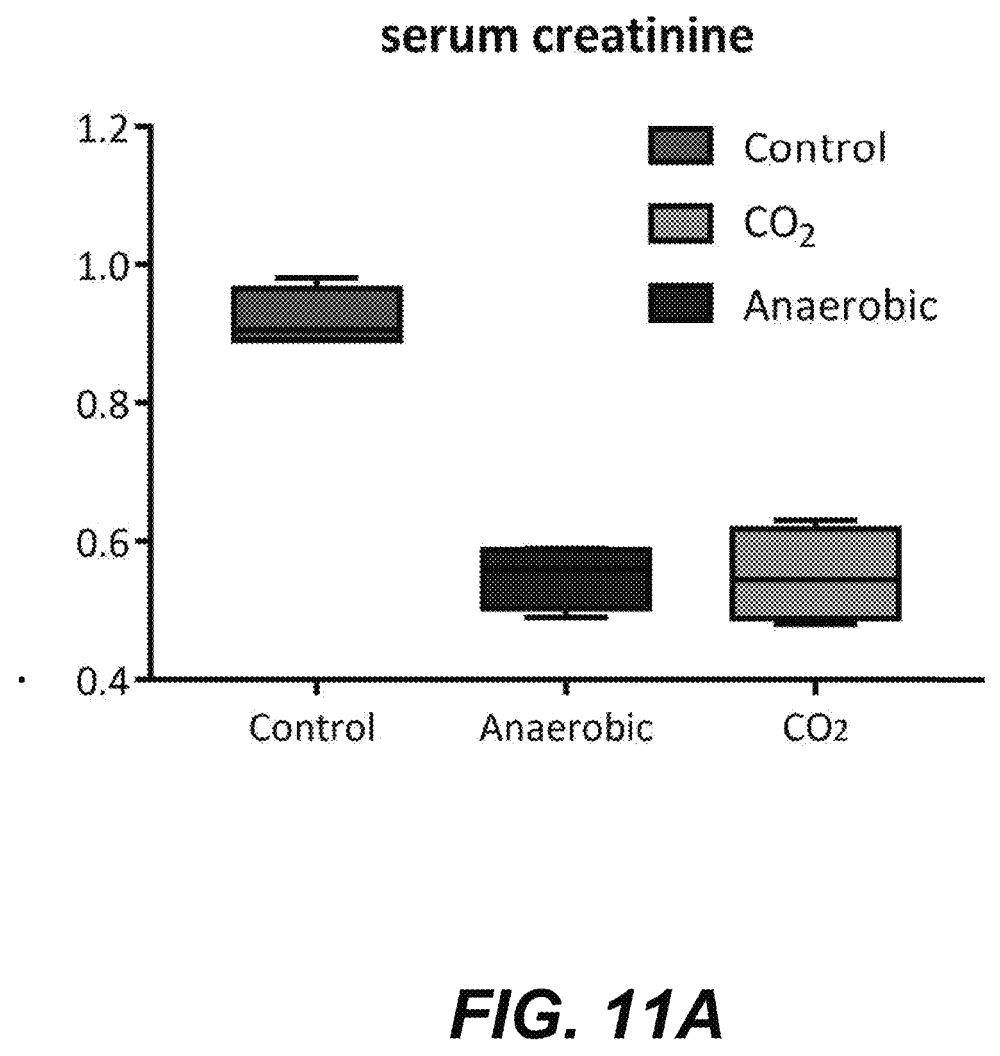
Figure 11B:
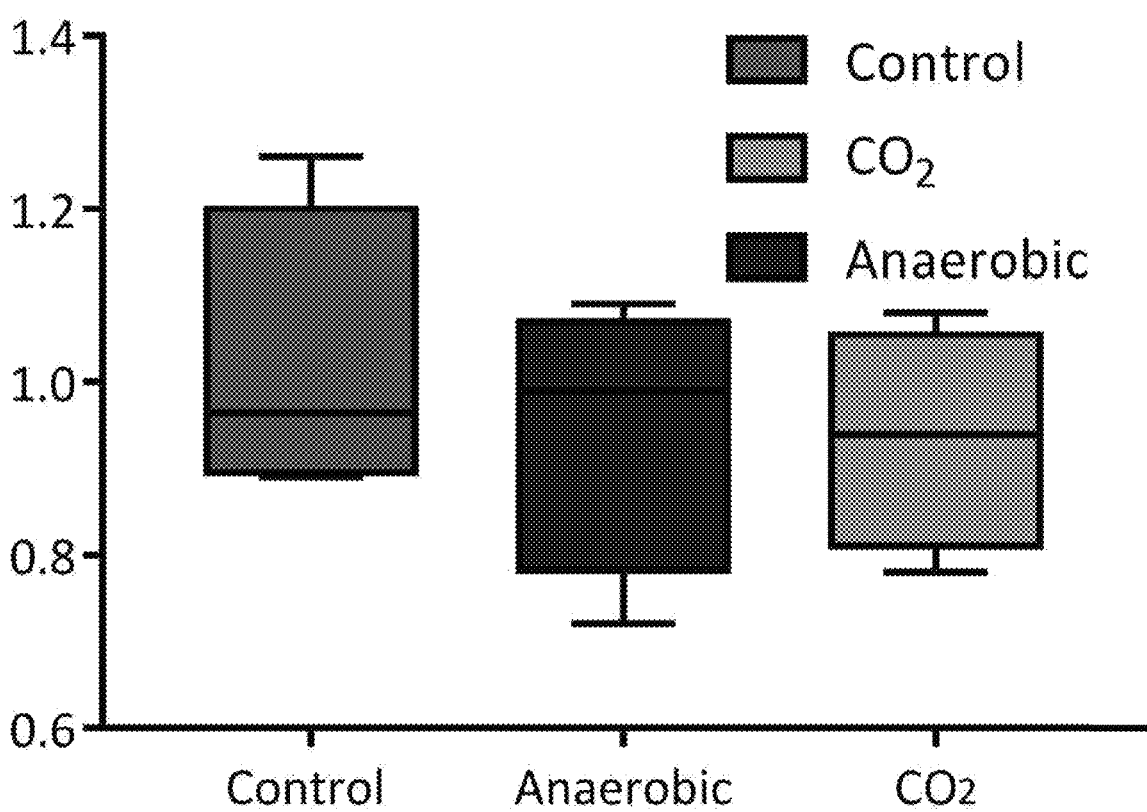
Figure 12A:
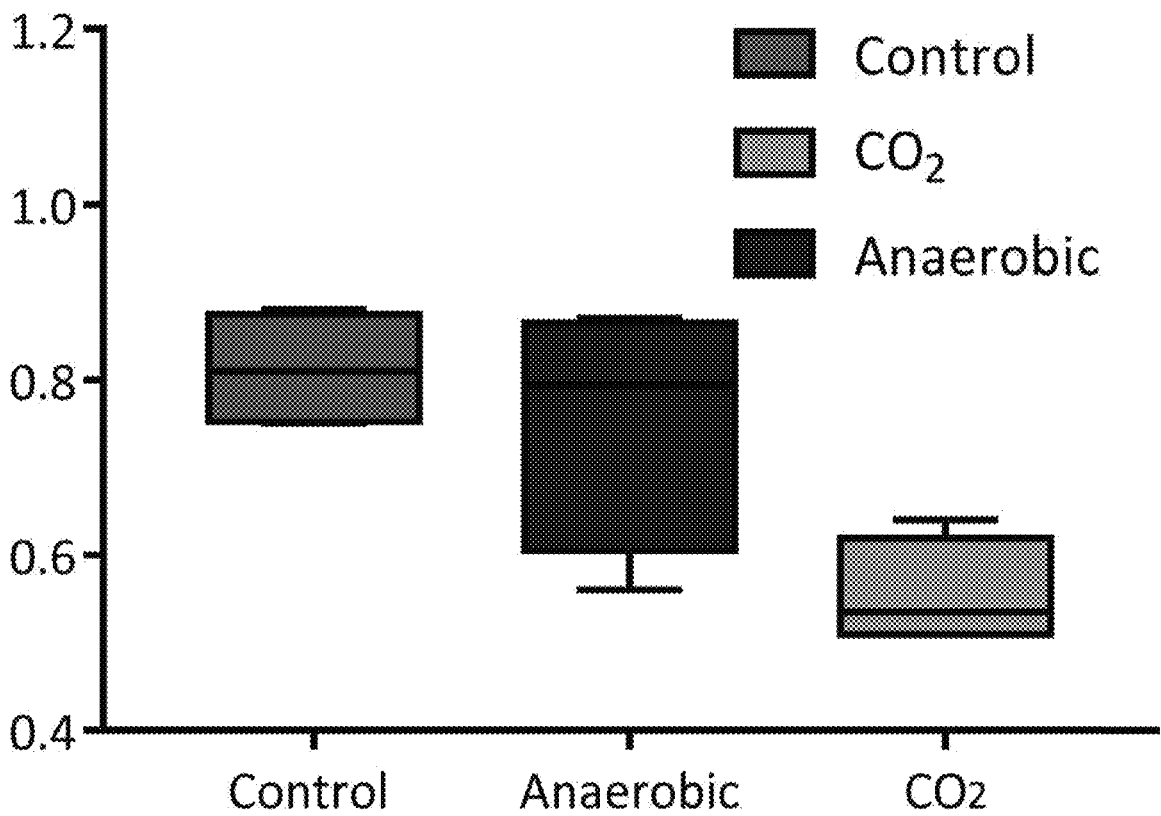
FIGS. 12A and 12B are graphs presenting the results of an exemplary embodiment according to the present disclosure, providing a comparison of the amount of blood urea nitrogen (BUN) in animals resuscitated with control, OR-RBCs, and OCR-RBCs stored for 1 week (FIG. 12A) or 3 weeks (FIG. 12B).
Figure 12B:
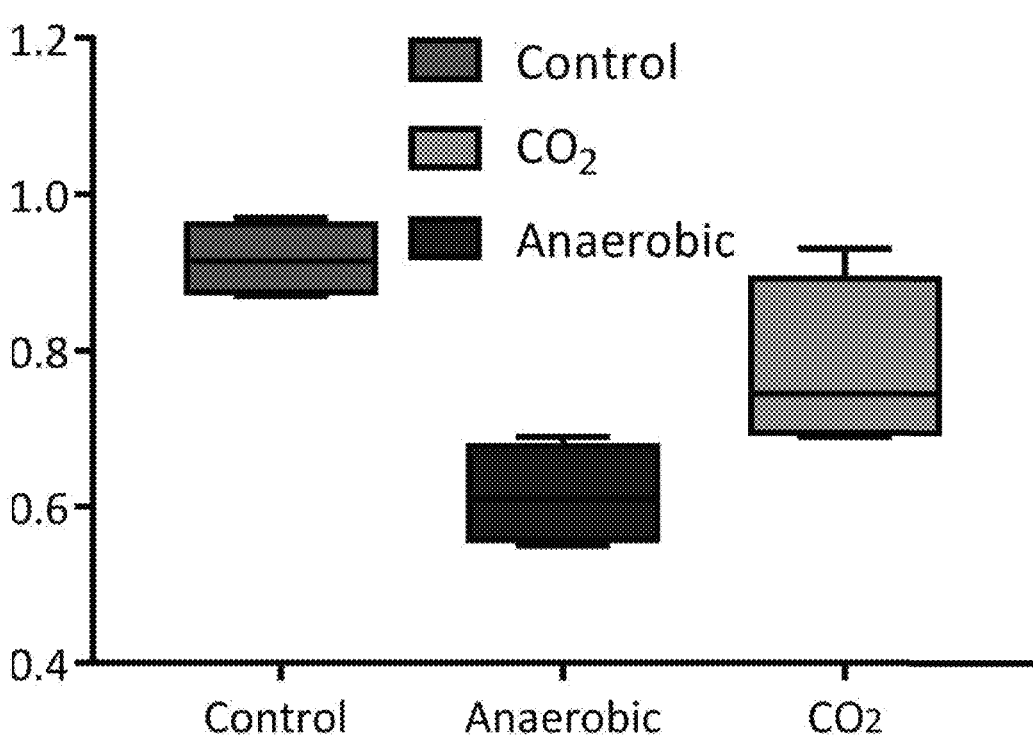

Animals are analyzed for organ injury and inflammation after experiencing hemorrhagic shock and resuscitation. Elevated levels of liver enzymes signify some form of liver damage or injury. Aspartate aminotransferase (AST) and alanine aminotransferase (ALT) levels were analyzed to determine liver damage. Resuscitation with OR and OCR RBCs previously stored for one week (FIG. 9A and FIG. 10A) and three weeks (FIG. 9B and FIG. 10B) reduced AST and ALT levels compared control RBCs stored for the same period of time. Serum creatinine and blood urea nitrogen (BUN) levels were analyzed to determine kidney function. OR and OCR RBCs stored for one week reduced serum creatinine levels greater than 30% compared to control RBCs (FIG. 11A). After three weeks of storage serum creatinine levels of animals treated with control, OR, and OCR RBCs overlap (FIG. 11B). BUN levels are decreased by greater than 30% in animals treated with OCR RBCs stored for one week compared to control (FIG. 12A). BUN levels also decreased by greater than 30% in animals treated with OR RBCs stored for three weeks compared to control (FIG. 12B). Overall, vital organ function was preserved with OR and OCR RBCs compared to control RBCs.

Figure 13A:
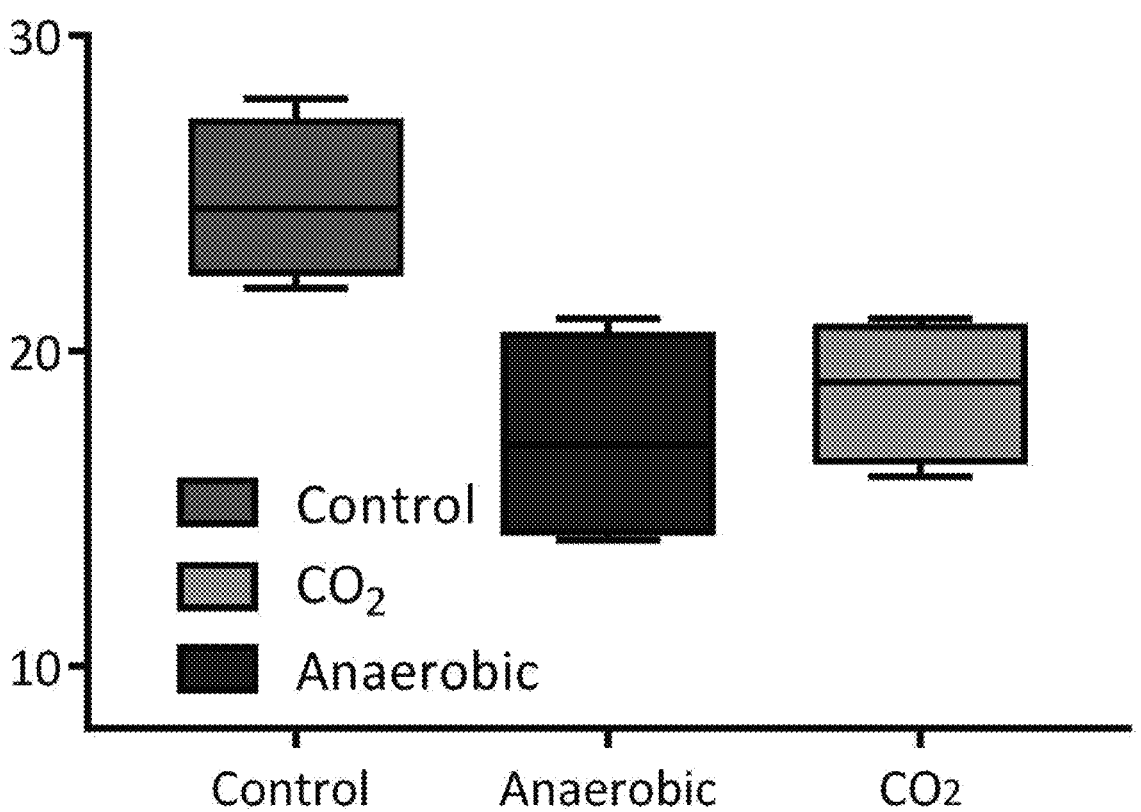
FIGS. 13A and 13B are graphs presenting the results of an exemplary embodiment according to the present disclosure, providing a comparison of the amount of CXCL1 in the liver of animals resuscitated with control, OR-RBCs, and OCR-RBCs stored for 1 week (FIG. 13A) or 3 weeks (FIG. 13B).
Figure 13B:
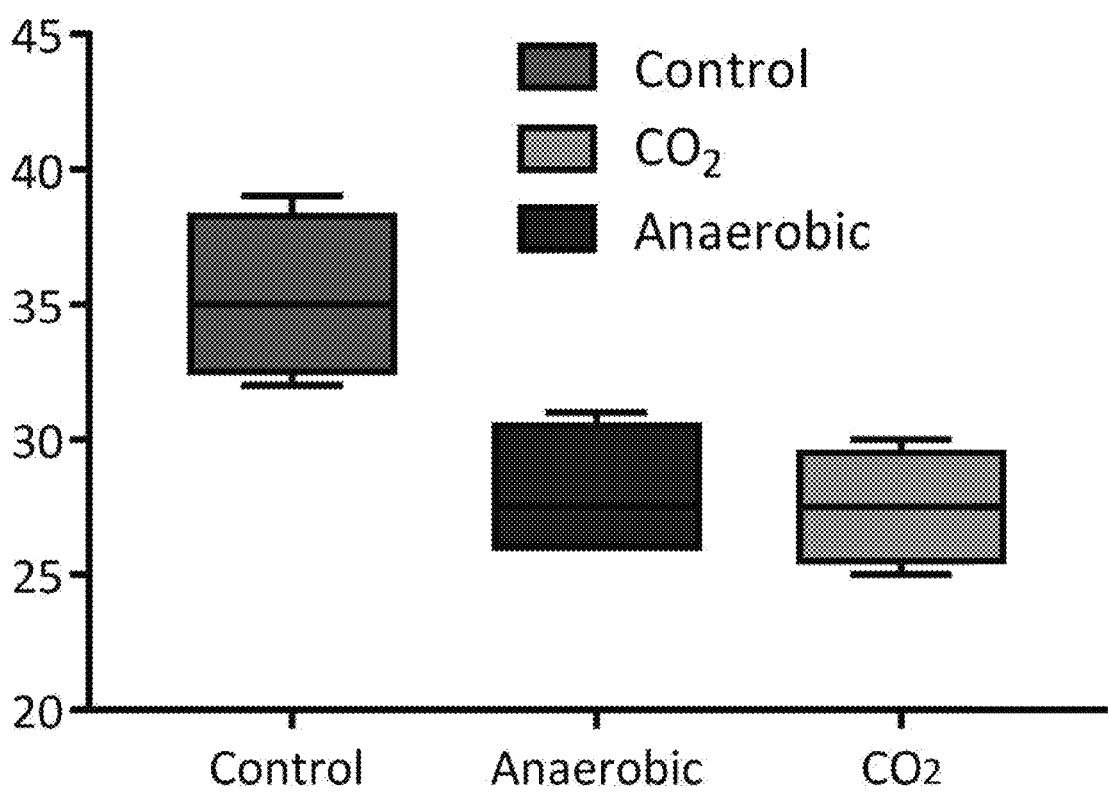
Figure 14A:
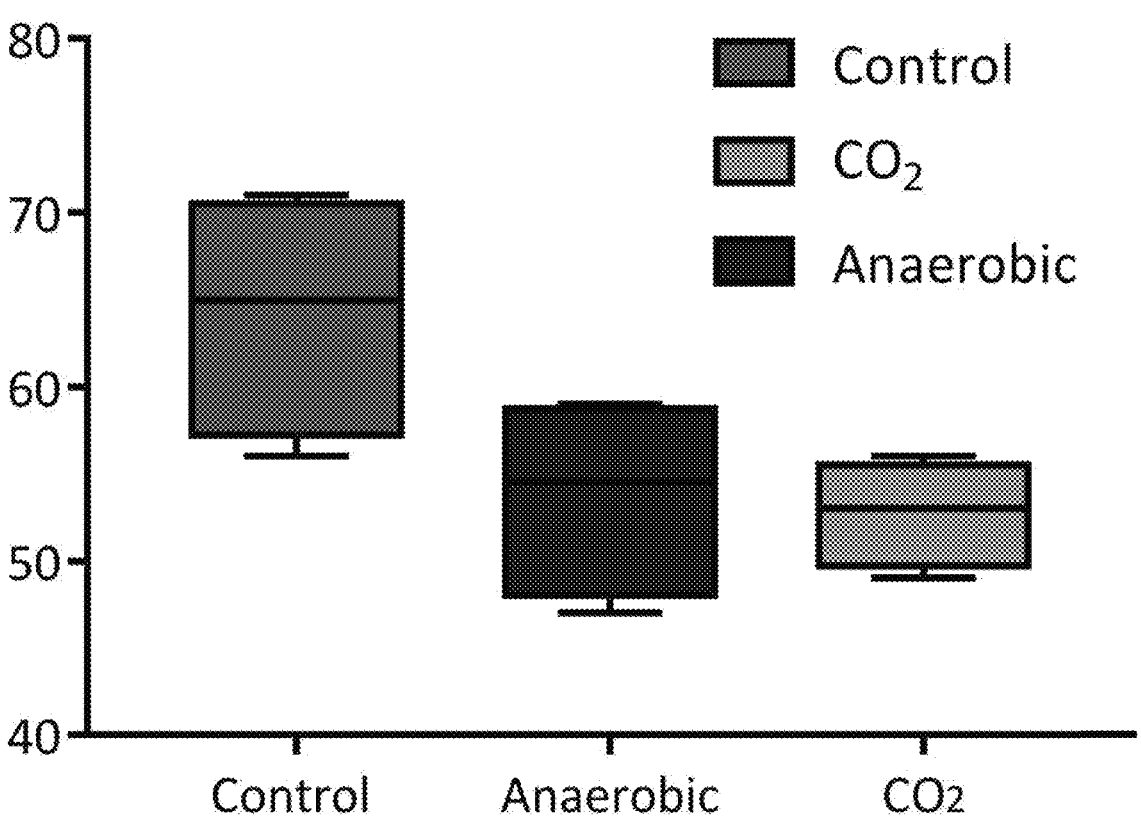
FIGS. 14A and 14B are graphs presenting the results of an exemplary embodiment according to the present disclosure, providing a comparison of the amount of CXCL1 in the spleen of animals resuscitated with control, OR-RBCs, and OCR-RBCs stored for 1 week (FIG. 14A) or 3 weeks (FIG. 14B).
Figure 14B:
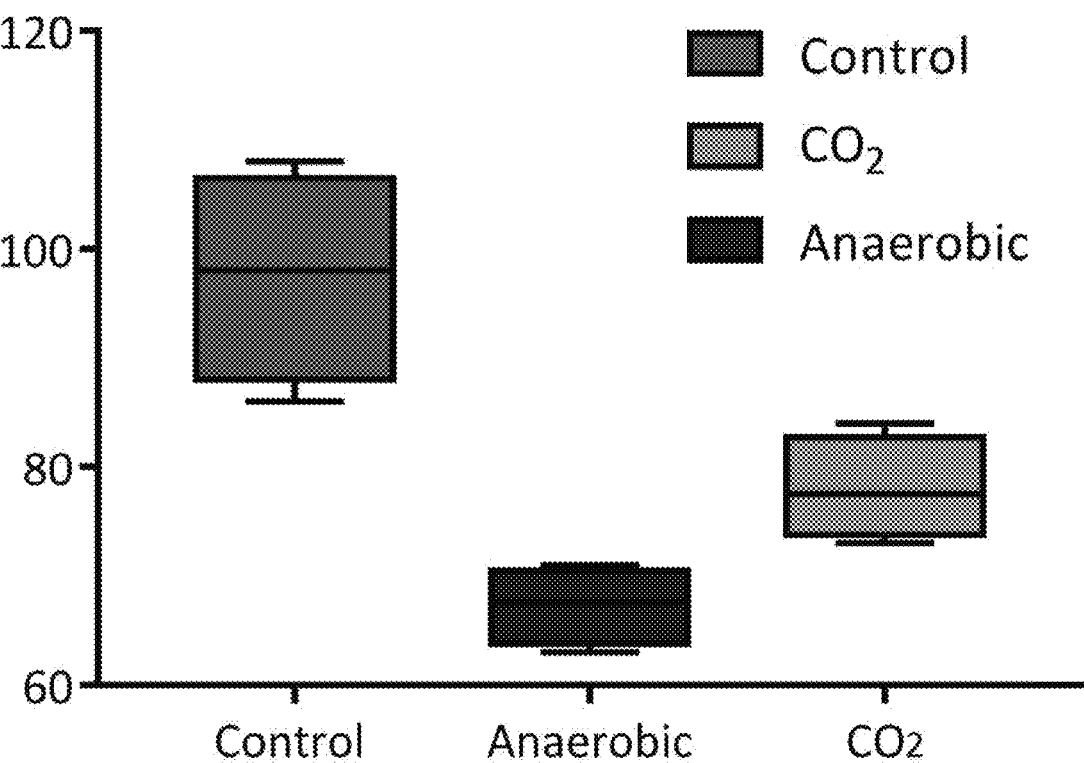
Figure 15A:
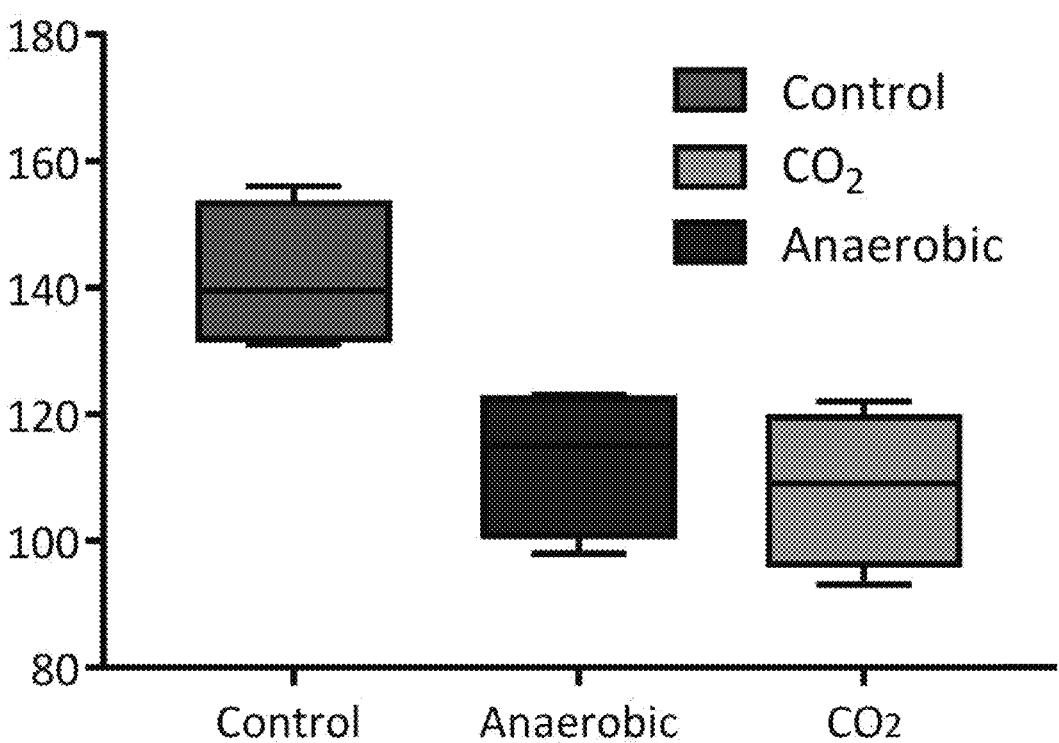
FIGS. 15A and 15B are graphs presenting the results of an exemplary embodiment according to the present disclosure, providing a comparison of the amount of CXCL1 in the lungs of animals resuscitated with control, OR-RBCs, and OCR-RBCs stored for 1 week (FIG. 15A) or 3 weeks (FIG. 15B).
Figure 15B:
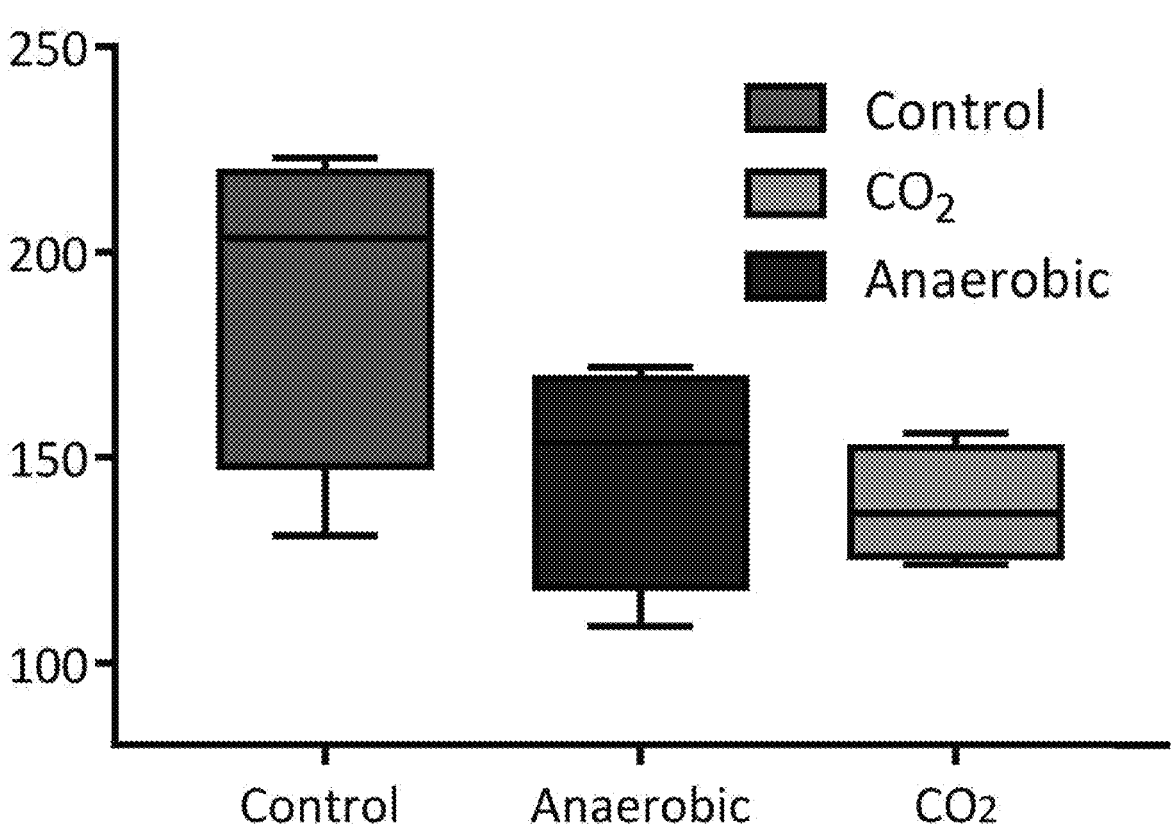
Figure 16A:
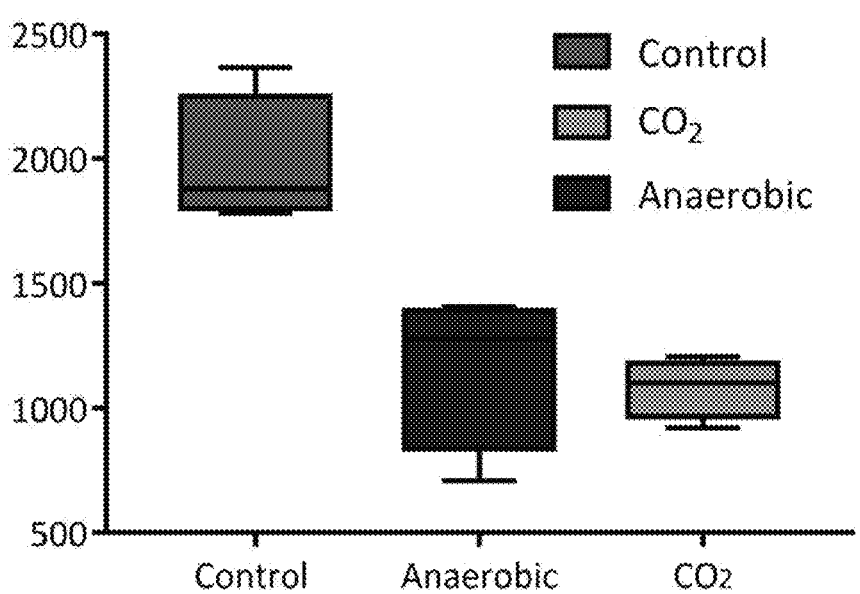
FIGS. 16A and 16B are graphs presenting the results of an exemplary embodiment according to the present disclosure, providing a comparison of the amount of urinary neutrophil gelatinase-associated lipocalin (u-NGAL) in animals resuscitated with control, OR-RBCs, and OCR-RBCs stored for 1 week (FIG. 16A) or 3 weeks (FIG. 16B).
Figure 16B:
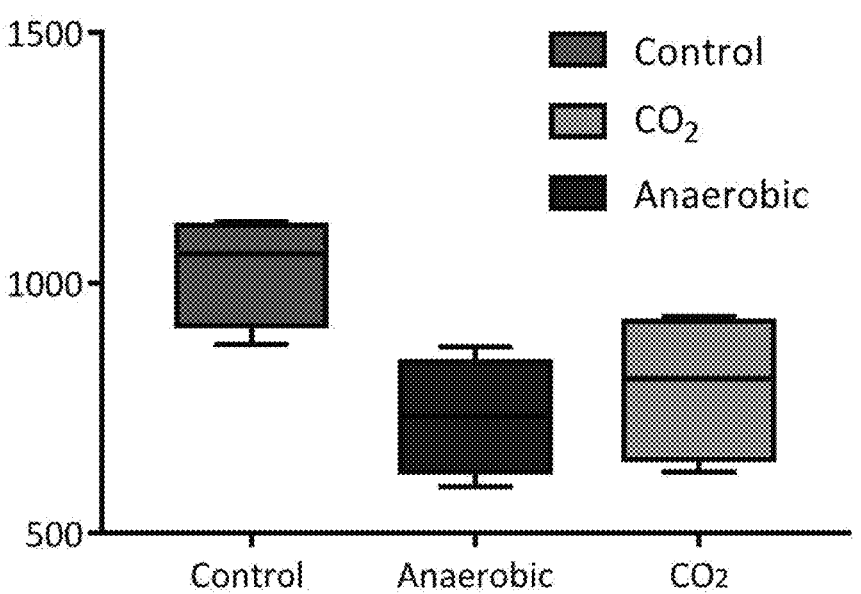
Figure 17A:
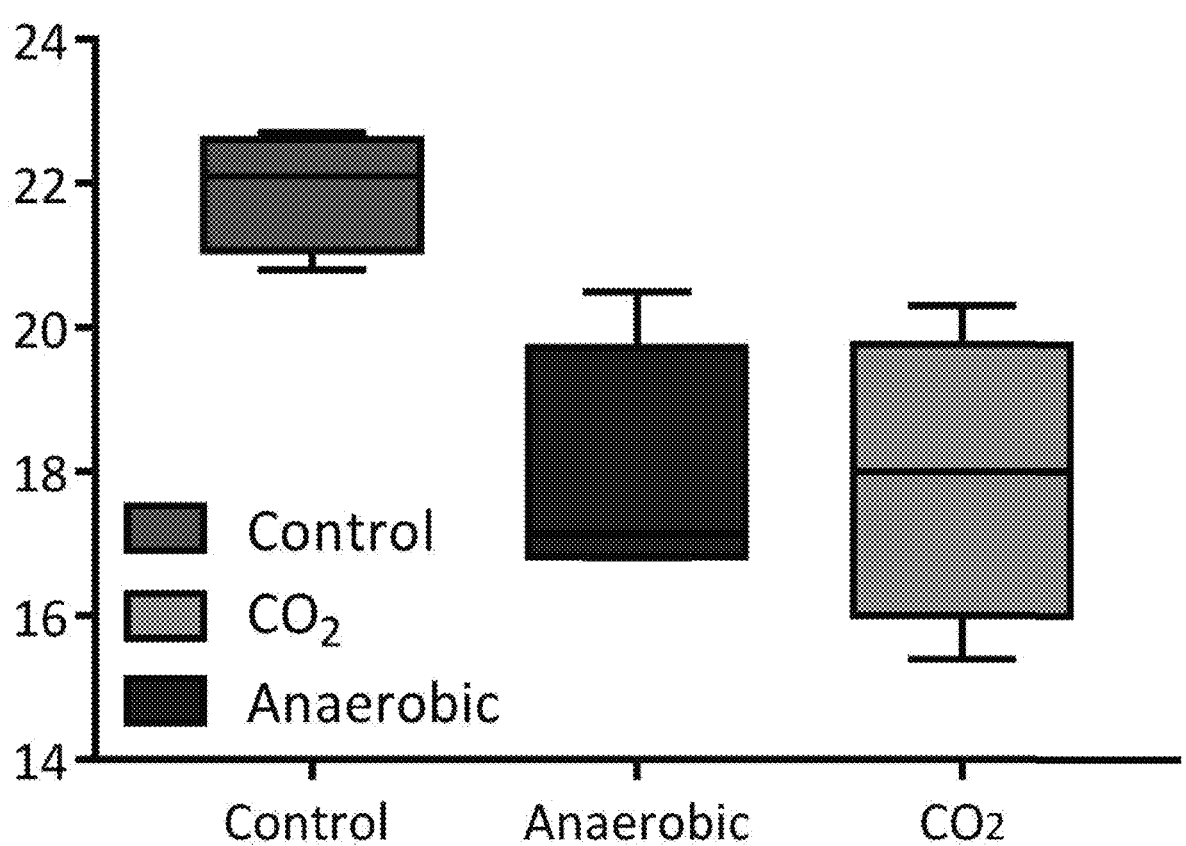
FIGS. 17A and 17B are graphs presenting the results of an exemplary embodiment according to the present disclosure, providing a comparison of the percentage of CD45+ neutrophils in animals resuscitated with control, OR-RBCs, and OCR-RBCs stored for 1 week (FIG. 17A) or 3 weeks (FIG. 17B).
Figure 17B:
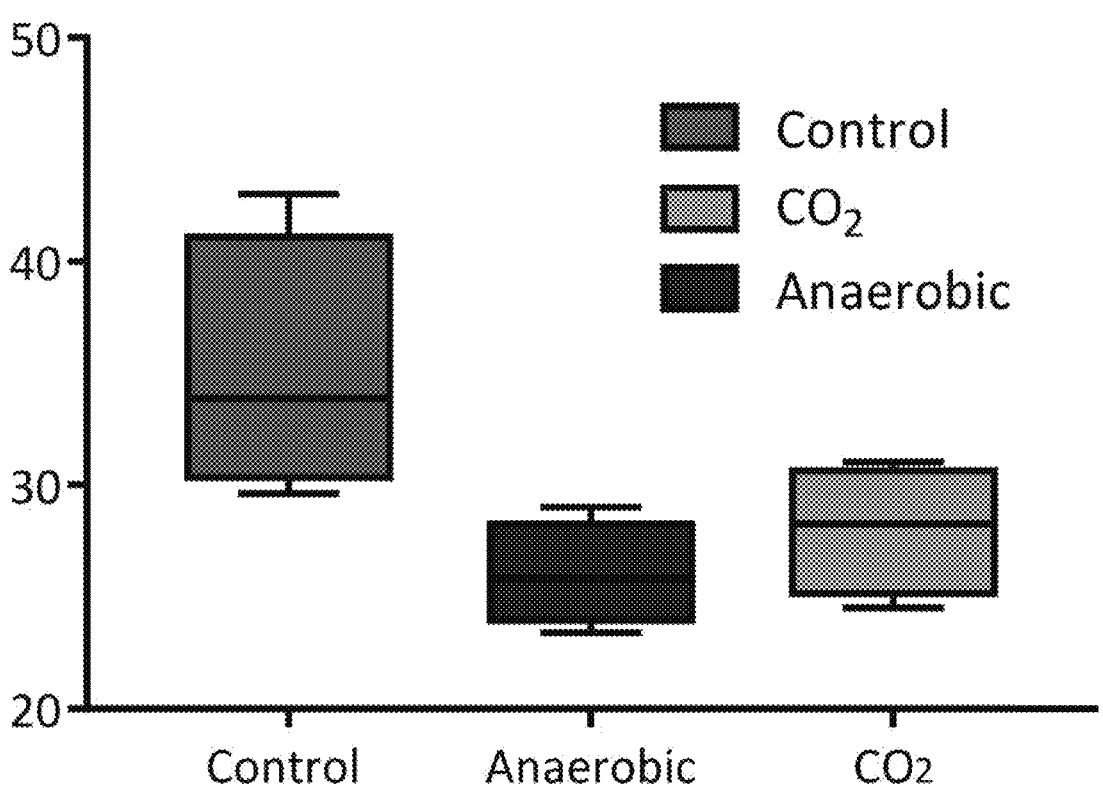
Figure 18A:
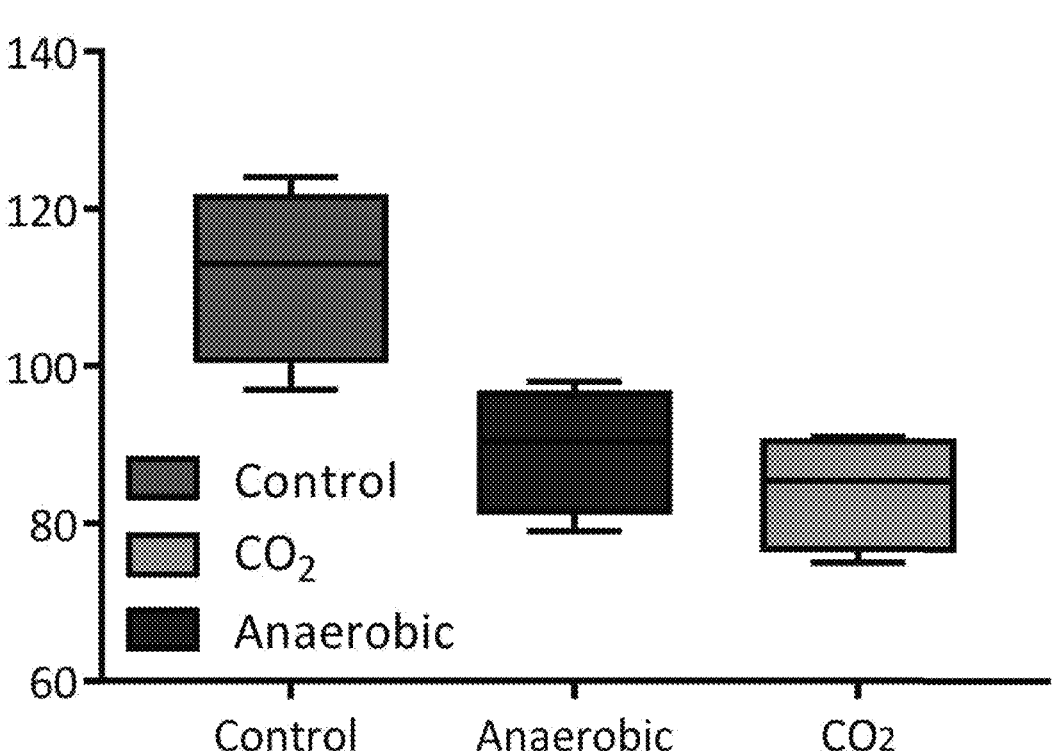
FIGS. 18A and 18B are graphs presenting the results of an exemplary embodiment according to the present disclosure, providing a comparison of the amount of IL-6 in animals resuscitated with control, OR-RBCs, and OCR-RBCs stored for 1 week (FIG. 18A) or 3 weeks (FIG. 18B).
Figure 18B:
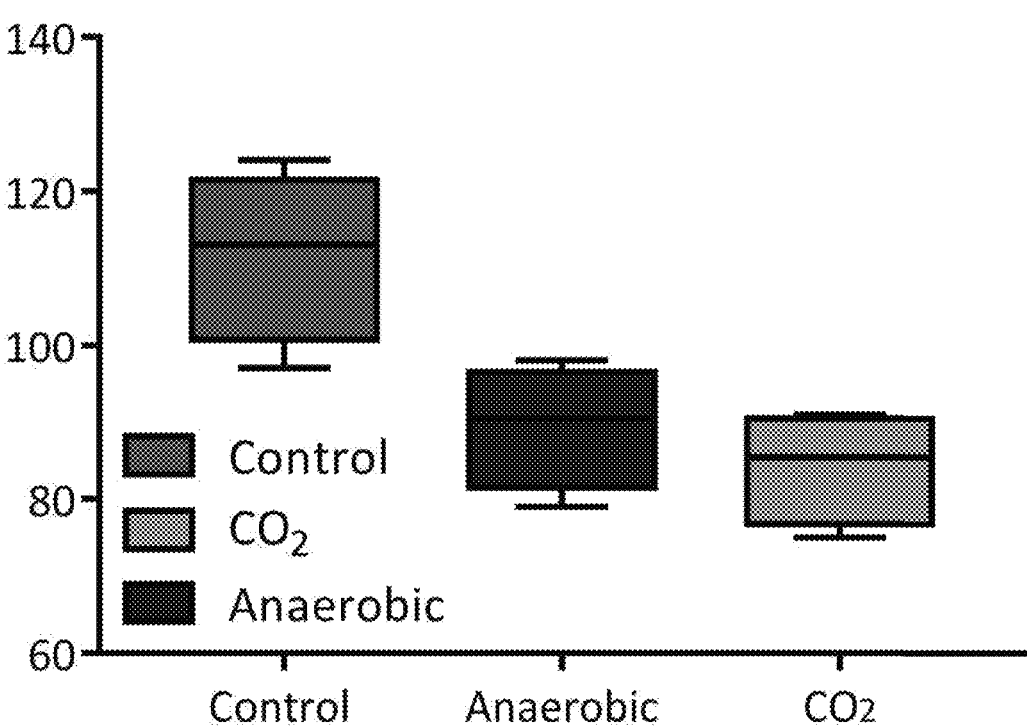

Liver, spleen and lungs are resected from animals upon completion of the in vivo studies and analyzed for various inflammatory factors including CXCL1, urinary neutrophil gelatinase-associated lipocalin (u-NGAL), IL-6, and neutrophils. CXCL1 is reduced in animals treated with OR and OCR RBCs stored for one or three weeks, compared to control stored for the same period of time (FIG. 13A, B, FIG. 14A, B, and FIG. 15A, B). As shown in FIGS. 16A and B, u-NGAL is reduced in the kidneys of animals treated with OR or OCR RBCs, stored for one or three weeks, compared to control RBCs stored for an equivalent amount of time (FIG. 16). As shown in FIGS. 17 and 18, the percentage of lungs resected from animals with CD45+ neutrophils and the level of IL-6 is significantly decreased in OR and OCR RBCs compared to control RBCs stored for the same period of time. These results show that organ injury and inflammation is decreased in animals treated with OR and OCR RBCs compared to animals treated with control RBCs.

Example 8: Thrombospondin Adhesion Assay

Figures 19A, 19B, 19C:
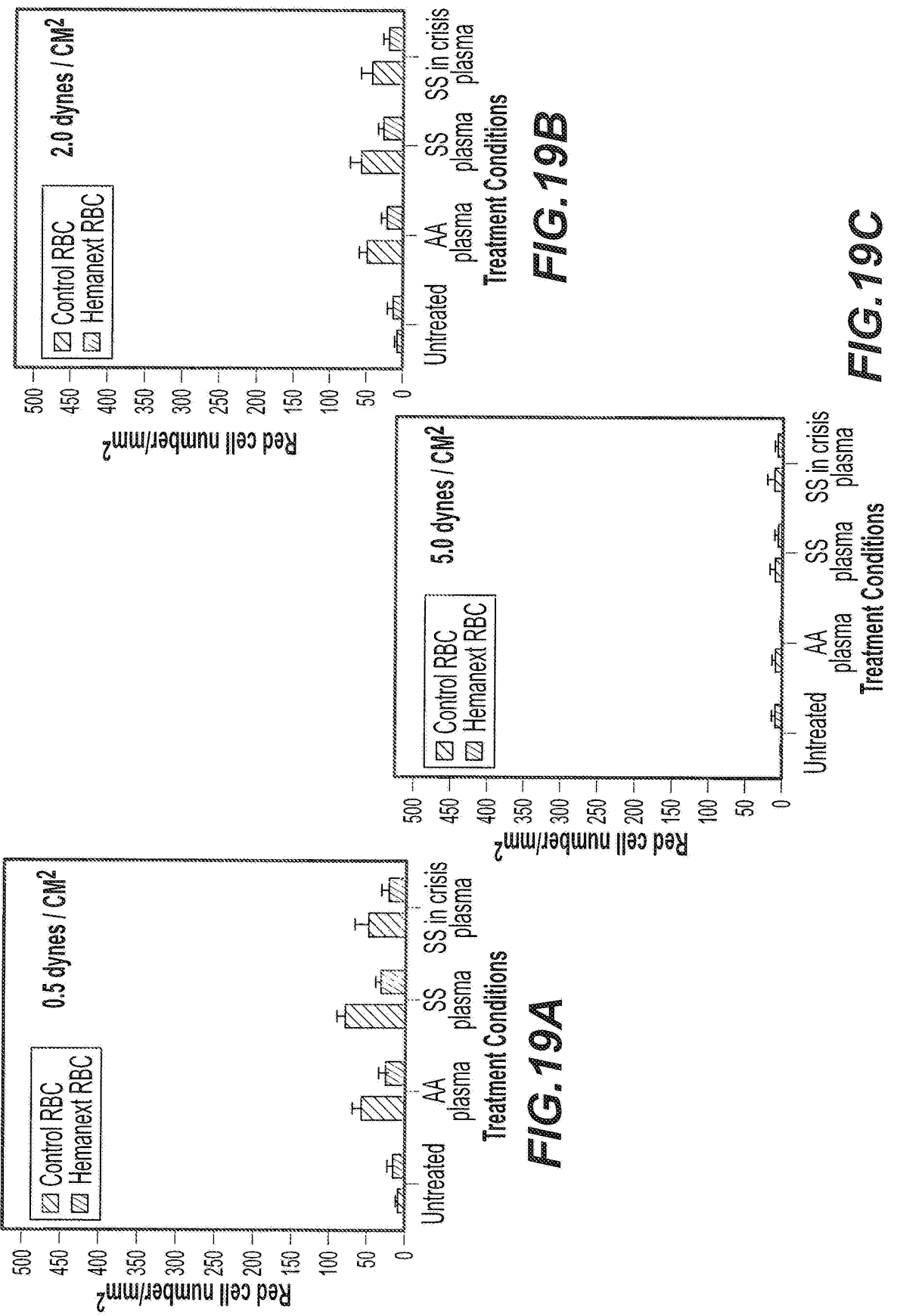
FIGS. 19A to C are graphs presenting the results of an exemplary embodiment according to the present disclosure, providing a comparison of adhesion of red blood cells to thrombospondin.

Thrombospondin is an important biomarker of disease severity in sickle cell disease. During vaso-occlusive crisis (episodes) in sickle cell disease, the level of circulating thrombospondin is significantly increased with corresponding increases in the adhesion of sickle red blood cells to vascular endothelium. Conventionally stored RBCs and oxygen reduced RBCs are compared to determine differences in adhesion to endothelial cells. Briefly, two units of O Positive whole blood is pooled in citrate-phosphate-dextrose (CPD)/SAGM. Each unit is filtered at room temperature with a leukocyte-reduction filter. The leuko-reduced whole blood (LR-WB) is transferred into a 2-liter blood collection bag. The pooled LR-WB is then divided into equal aliquots of 500 ml (Unit A and Unit B) and processed into packed red blood cells and plasma. Plasma is removed and stored at −70° C. Packed RBCs (pRBCs) in unit A are resuspended in SAGM and pRBCs in unit B are resuspended in PAGGSM. The pRBCs in unit B are deoxygenated for 3 hours at room temperature using the Hemanext Oxygen Reduction System. Units are stored for 42 days at 4° C. Samples are extracted from each unit and analyzed to determine complete blood count (CBC), gas panel analysis and adhesion to thrombospondin on a microchip after pre-incubation in normal plasma or plasma from patients with sickle cell disease. Samples collected on day 0 are incubated with 0.4% bovine serum albumin (BSA), normal plasma (AA), plasma from sickle cell patients in steady state (SS), or plasma from sickle cell patients in crisis. The incubated samples are then incubated with adhesion assay microchips. To determine the effects of different shear stresses on the adhesion of oxygen reduced RBCs and conventionally stored RBCs, cells are subjected to a increased shear stress from 0.5 to 5 dynes/cm$^2$. As shown in FIG. 19, the system is stable and responsive to changes in shear stresses. As the shear stress increases there is a gradual decrease in the number of cells that are adhered to the thrombospondin matrix. These results further demonstrate the strength of adhesion of RBCs to thrombospondin.

Figures 20A, 20B, 20C:
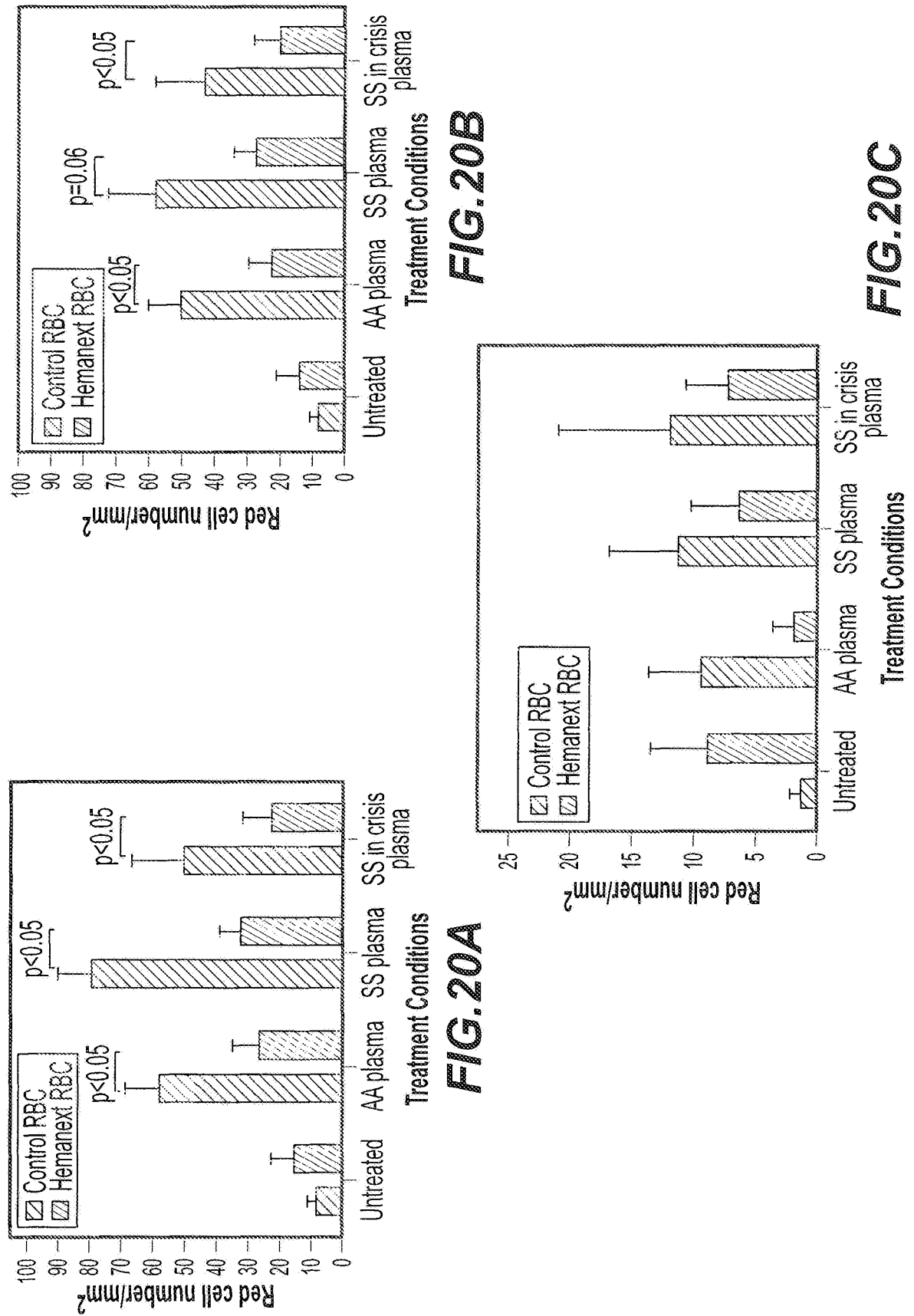
FIGS. 20A to C are graphs presenting the results of an exemplary embodiment according to the present disclosure, providing a comparison of adhesion of red blood cells to thrombospondin between conventionally stored or oxygen reduced stored red blood cells.

To test the effect of RBC storage conditions on thrombospondin adhesion, samples collected at days 0, 21, and 42 are subjected to 0.5 dynes/cm$^2$ (FIG. 20A), 2.0 dynes/cm$^2$ (FIG. 20B), or 5.0 dynes/cm$^2$ (FIG. 20C) sheer stress. As shown in FIG. 20, oxygen reduced red blood cells are significantly less adhesive to thrombospondin compared to conventionally stored red blood cells.

Example 9: Hemolysis of Oxygen-Reduced and Control RBCs

Figure 21:
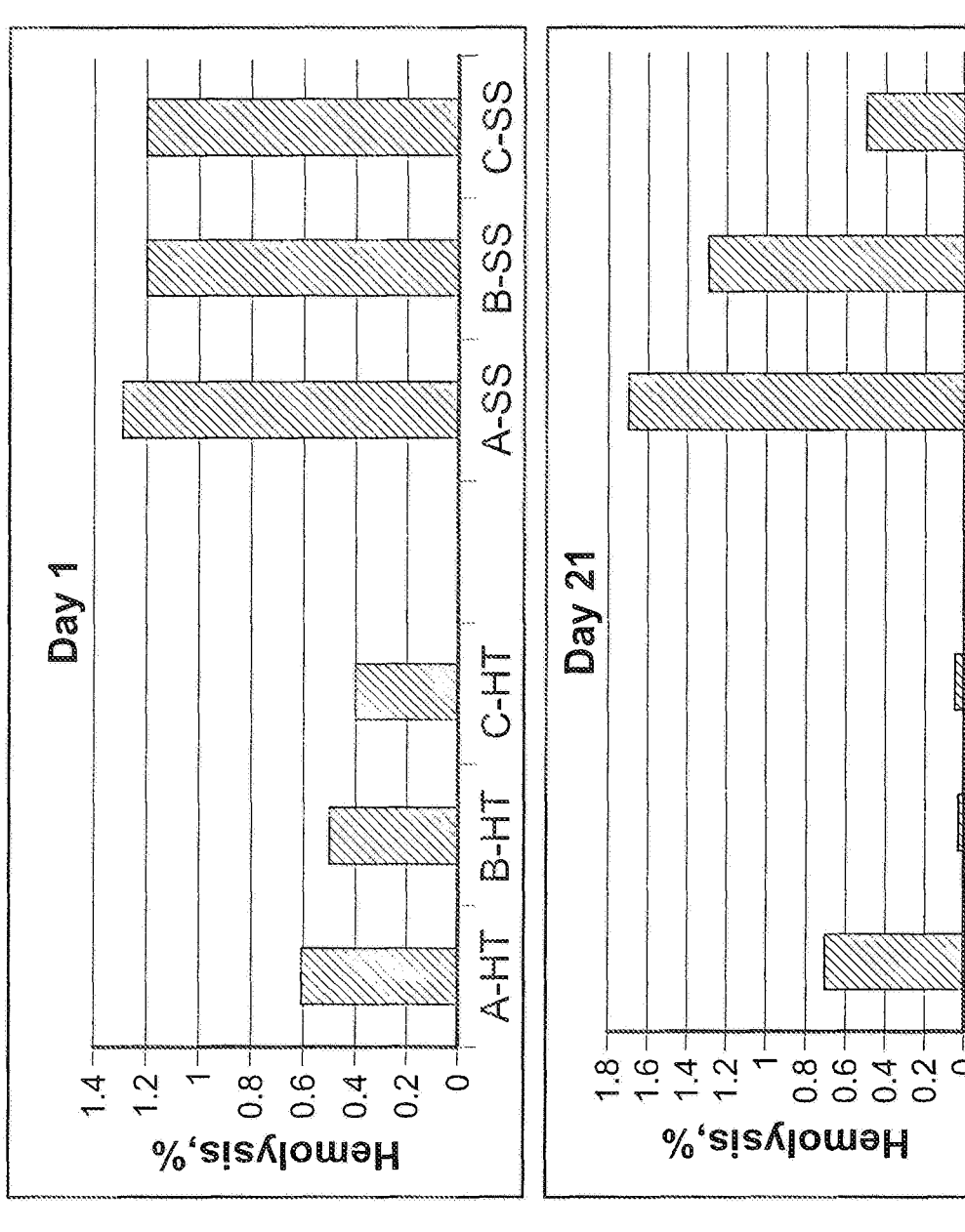
FIG. 21 shows the results of an exemplary embodiment according to the present disclosure, providing a comparison of hemolysis in conventionally stored, oxygen reduced stored, and oxygen and carbon dioxide reduced stored red blood cells incubated with healthy of sickle cell plasma.

To determine the effect of sickle plasma on hemolysis, 20 mL samples are collected from two sickle cell disease patients greater than 28 days after exchange transfusion (TF) and one healthy patient (HT). The samples are distributed into 15 mL centrifuge tubes and centrifuged for 15 mins at 1500× g at room temperature (without brake). Platelet rich plasma (PRP) from each 15 mL tube is then transferred to a new 15 mL tube and centrifuged for 15 mins at 1500× g at room temperature (without brake). A clean disposable bulb pipette is used to transfer PRP from each centrifuge tube to a 15 mL pooling tube. The platelet poor plasma (PPP) is aliquoted to the autoclaved and pre-labelled 1.5 mL tubes, 1 mL each. The PPP is stored at −40° C. until use. Flow adhesion is conducted with RBCs resuspended in two TF samples. The TF PPP sample supporting higher baseline adhesion (TF006) is selected (FIG. 21).

Three sets of pRBCs—conventionally stored (A), carbon dioxide depleted and 40% oxygen (B), and carbon dioxide and oxygen depleted (C)—are prepared and stored. Aliquots are collected from each set on days 1 and 21 of storage. The samples are transferred to 15 mL centrifuge tubes and centrifuged for 15 mins at 1500×g. The supernatant is discarded and RBC pellets are reconstituted. Eighty microliters of packed and washed RBCs from A, B, and C are resuspended in 40 microliters of prepared PPPs from sickle cell plasma (SS) and healthy plasma (HT), and incubated at 37C on a nutator (4 RPM) for 2 hours and 24 hours. The percent hemolysis is decreased in carbon dioxide and oxygen depleted RBCs compared to conventionally stored RBCs.

Example 10: Effect of Sickled Plasma on Deformability

Three RBC units are pooled, leuko-reduced (LR), and equally divided into group A (control) and group B (oxygen reduced). Group B RBCs are processed to contain approximately 5% SO and approximately 8 mmHg $CO_2$. Group A and B RBCs are stored at 4° C. for 42 days. Aliquots of RBCs from both groups A and B are incubated at 37° C. with (1) healthy donor plasma for 3 hours, (2) healthy donor plasma for 12 hours, (2) sickle cell donor plasma for 3 hours, and (4) sickle cell donor plasma for 12 hours. The matched samples from group A and group B are analyzed side-by-side on microvascular analysis chip. Deformability is measured as outlet bulk flow. Deformability is increased in oxygen reduced RBCs incubated with sickle cell plasma compared to control RBCs incubated with healthy plasma. This increase in deformability is observed after 3 and 12 hours of incubation.

The invention claimed is:

1. A method of improving a transfusion outcome in a sickle cell disease patient in need of a blood transfusion comprising administering stored oxygen reduced blood to the sickle cell disease patient, wherein the stored oxygen reduced blood comprises red blood cells having increased deformability, wherein the stored oxygen reduced blood has an oxygen saturation of 20% or less during a storage period, wherein the increased deformability is compared to conventionally stored blood stored for an identical storage period, and wherein the improved transfusion outcome comprises reduced occurrence of dactylitis, reduced occurrence of pain crises, reduced complications from anemia, reduced occurrence of infection, reduced spleen damage, reduced risk of stroke, or any combination thereof compared to a sickle cell disease patient having been administered conventionally stored blood stored for an identical storage period.

2. The method of claim 1, wherein the sickle cell disease is sickle cell anemia.

3. The method of claim 1, wherein the sickle cell disease is sickle cell crisis.

4. The method of claim 1, wherein the sickle cell disease is selected from the group consisting of hemoglobin SS (HbSS), hemoglobin SC (HbSC), hemoglobin S beta thalassemia+(HbSB+), hemoglobin S (beta-zero) thalassemia (HbSB), hemoglobin SD (HbSD), hemoglobin SE (HbSE), and hemoglobin SO (HbSO).

5. The method of claim 1, wherein the sickle cell disease patient experiences an improved recovery at 24 hours after the administration compared to a sickle cell disease patient having been administered conventionally stored blood stored for an identical time period, and wherein the improved recovery is maintenance of a normal hematocrit level.

6. The method of claim 1, wherein the increased deformability compared to conventionally stored blood is when the stored oxygen reduced blood is in the presence of sickle cell plasma.

7. The method of claim 1, further comprising reducing carbon dioxide in the stored oxygen reduced blood.

8. The method of claim 1, wherein the complications from anemia are selected from the group consisting of fatigue, irritability, dizziness, difficulty breathing, pale skin color, jaundice, slow growth, and delayed puberty.

9. The method of claim 1, wherein the spleen damage is splenic sequestration or splenic enlargement.

\* \* \* \* \*